(12) United States Patent
Takemoto

(10) Patent No.: US 10,814,069 B2
(45) Date of Patent: Oct. 27, 2020

(54) INJECTOR

(71) Applicant: TERUMO KABUSHIKI KAISHA, Tokyo (JP)

(72) Inventor: Masafumi Takemoto, Minami-Alps (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 104 days.

(21) Appl. No.: 15/940,263

(22) Filed: Mar. 29, 2018

(65) Prior Publication Data

US 2018/0214639 A1    Aug. 2, 2018

Related U.S. Application Data

(63) Continuation of application No. 14/664,205, filed on Mar. 20, 2015, now Pat. No. 9,962,497, which is a
(Continued)

(30) Foreign Application Priority Data

Aug. 14, 2013   (JP) ................. 2013-168618

(51) Int. Cl.
  *A61M 5/32*   (2006.01)
  *A61M 5/00*   (2006.01)
  *A61M 5/31*   (2006.01)

(52) U.S. Cl.
  CPC .......... *A61M 5/3202* (2013.01); *A61M 5/326* (2013.01); *A61M 5/3213* (2013.01);
(Continued)

(58) Field of Classification Search
  CPC .............. A61M 5/3202; A61M 5/3213; A61M 5/3269; A61M 5/3271; A61M 5/3272; A61M 2005/3109
  See application file for complete search history.

(56) References Cited

U.S. PATENT DOCUMENTS

| 4,932,940 A | 6/1990 | Walker et al. |
| 4,966,592 A | 10/1990 | Burns et al. |

(Continued)

FOREIGN PATENT DOCUMENTS

| CN | 101868272 A | 10/2010 |
| JP | 2008-536598 A | 9/2008 |

(Continued)

OTHER PUBLICATIONS

European search report issued in corresponding EP application No. 14836869.9 dated Mar. 10, 2017.
(Continued)

*Primary Examiner* — Bradley J Osinski
(74) *Attorney, Agent, or Firm* — Foley & Lardner LLP

(57) ABSTRACT

An injector includes a hollow needle; a main body unit including a needle holding portion that holds the needle; and a protection device configured to cover the needle before and after puncturing a puncture target with the needle. The protection device includes: an inner member attached to the needle holding portion and being freely rotatable around an outer periphery of the needle holding portion; and an outer member configured to (i) cover an order side of the needle and the inner member before puncturing, (ii) expose the needle by moving toward a proximal end side relative to the main body unit at a time of puncturing, and (iii) cover a distal end of the needle by moving toward a distal end side relative to the main body unit after puncturing.

18 Claims, 25 Drawing Sheets

Related U.S. Application Data continuation of application No. PCT/JP2014/059019, filed on Mar. 27, 2014.

(52) U.S. Cl.
CPC ........ *A61M 5/3269* (2013.01); *A61M 5/3271* (2013.01); *A61M 5/3272* (2013.01); *A61M 5/002* (2013.01); *A61M 5/3204* (2013.01); *A61M 2005/3109* (2013.01)

(56) References Cited

U.S. PATENT DOCUMENTS

| | | |
|---|---|---|
| 5,519,931 A | 5/1996 | Reich |
| 5,554,131 A | 9/1996 | Lacivita |
| 6,719,730 B2 | 4/2004 | Jansen et al. |
| 2005/0222539 A1 | 10/2005 | Gonzales et al. |
| 2009/0005742 A1 | 1/2009 | Liversidge |
| 2009/0024093 A1 | 1/2009 | Carrel et al. |
| 2010/0268170 A1 | 10/2010 | Carrel et al. |
| 2011/0077592 A1 | 3/2011 | Takemoto |
| 2013/0030365 A1 | 1/2013 | Liversidge |

FOREIGN PATENT DOCUMENTS

| | | |
|---|---|---|
| JP | 2010-540059 A | 12/2010 |
| JP | 2011-513035 A | 4/2011 |
| JP | 2013-529987 A | 7/2013 |
| WO | WO-2006/131832 A1 | 12/2006 |
| WO | WO-2009/040602 A1 | 4/2009 |
| WO | WO-2009/114542 A1 | 9/2009 |
| WO | WO-2009/119770 A1 | 10/2009 |
| WO | WO-2012/085026 A1 | 6/2012 |
| WO | WO-2013/134465 A1 | 9/2013 |

OTHER PUBLICATIONS

First Office Action issued in corresponding CN application No. 201480002330.2.

First Office Action issued in corresponding JP application No. 2015-512933 dated Jan. 8, 2016.

International Search Report and Written Opinion issued in International patent application No. PCT/JP2014/059019 dated Feb. 16, 2016.

Examination Report dated Nov. 14, 2019 in corresponding Indian Application No. 2540/DELNP/2015.

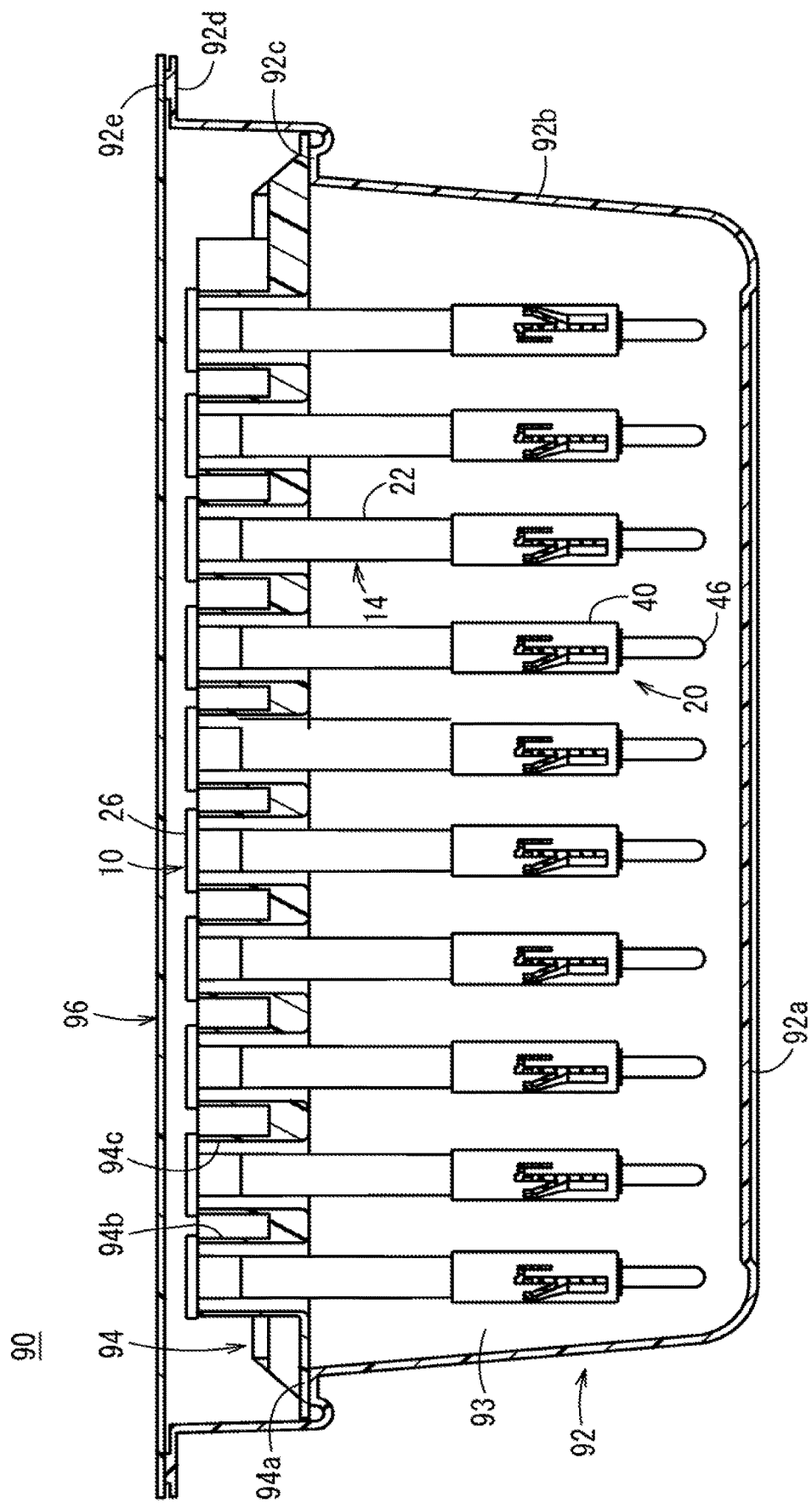

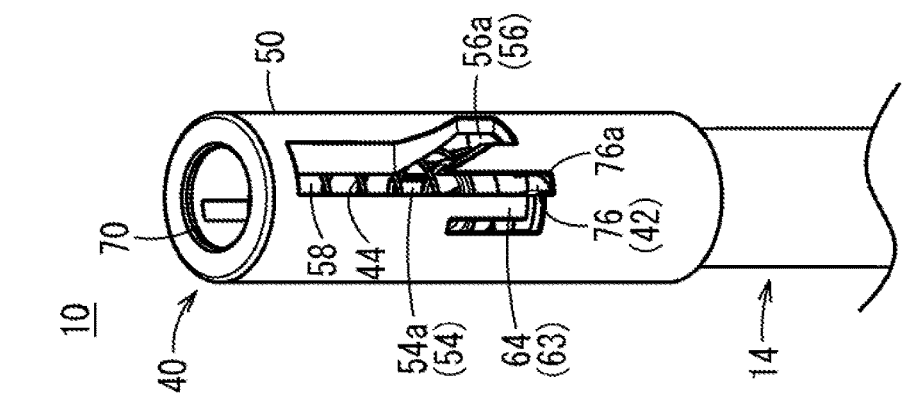
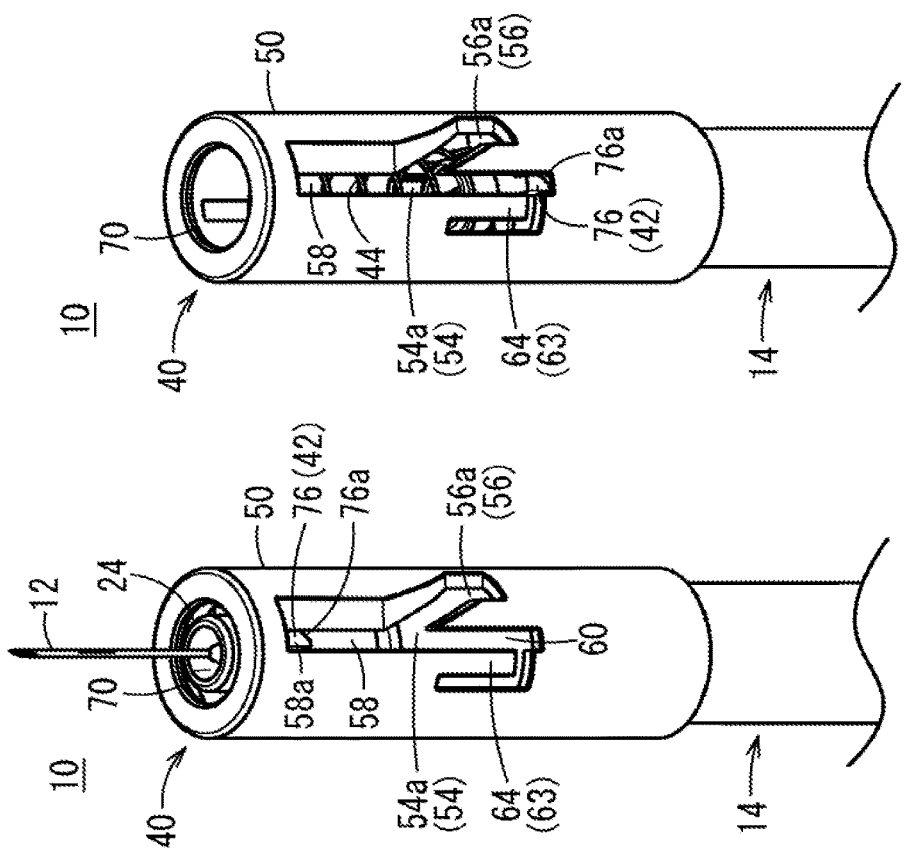
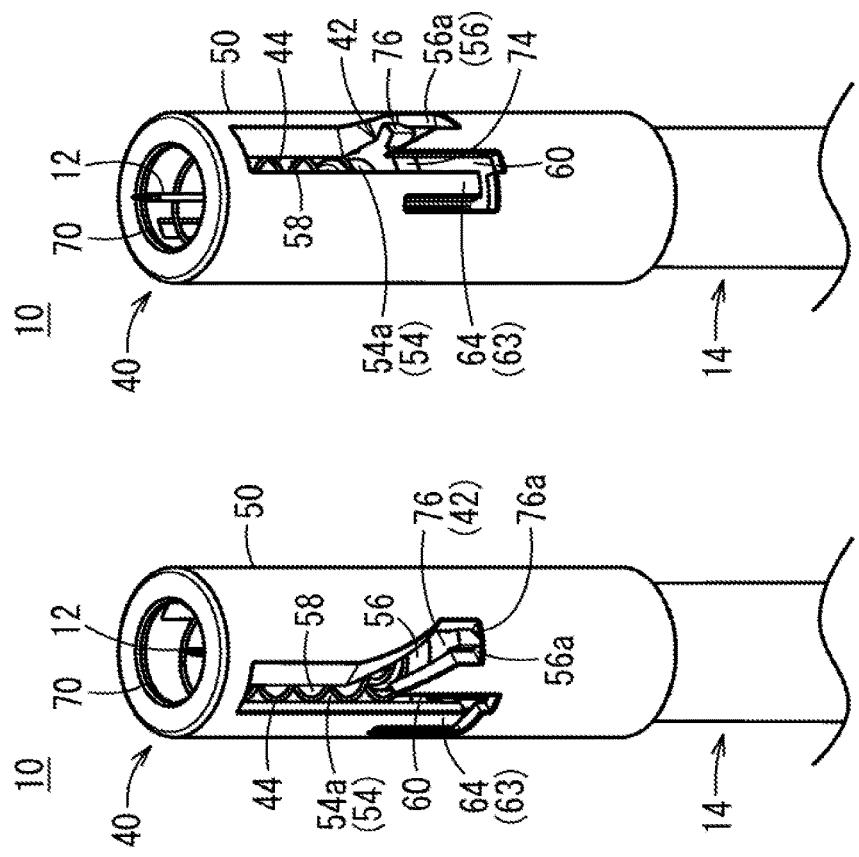

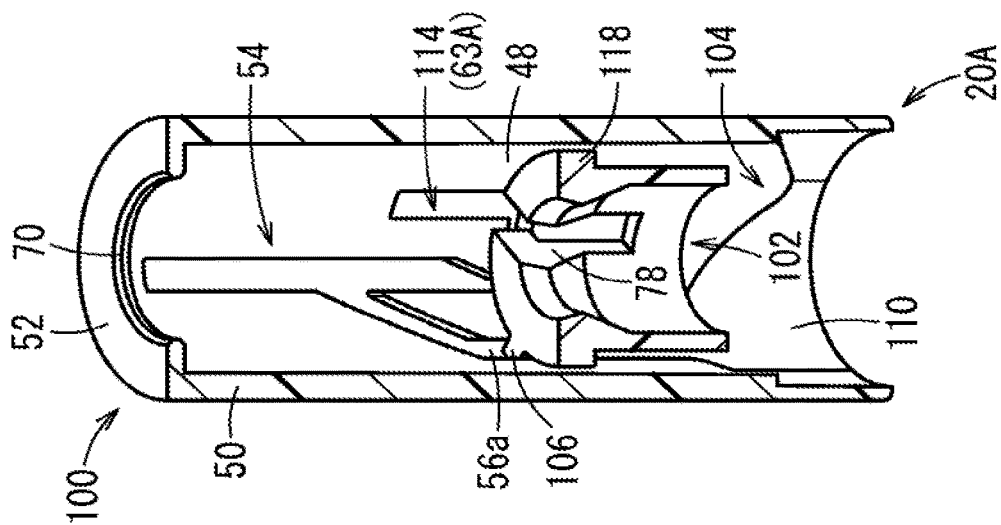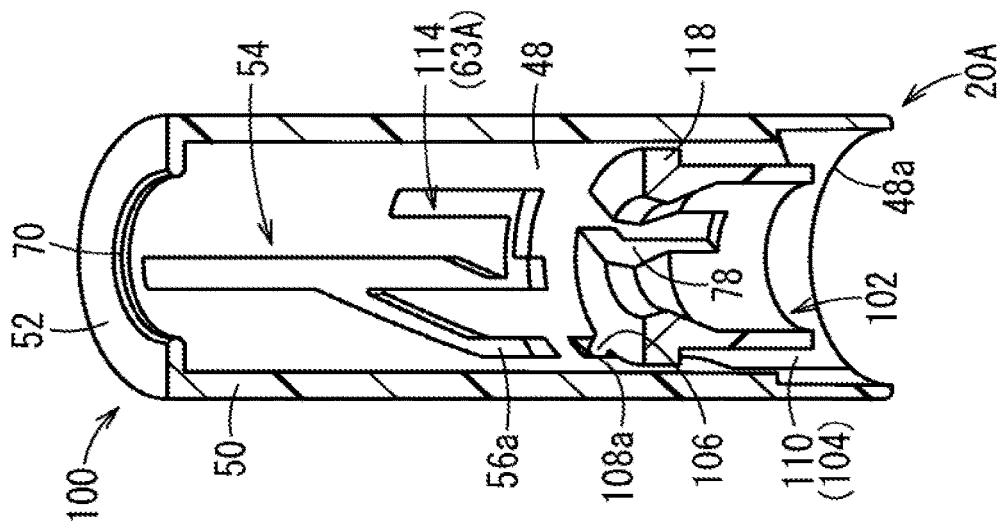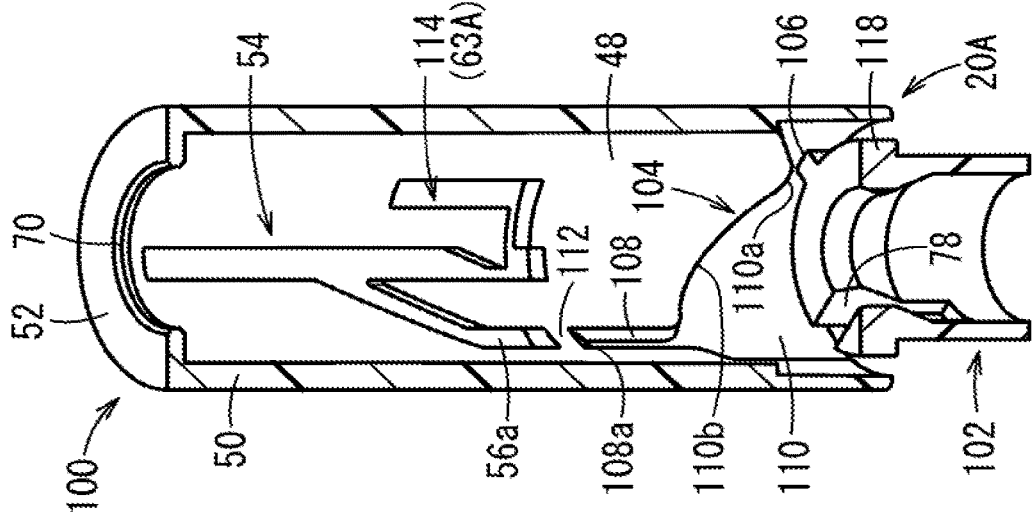

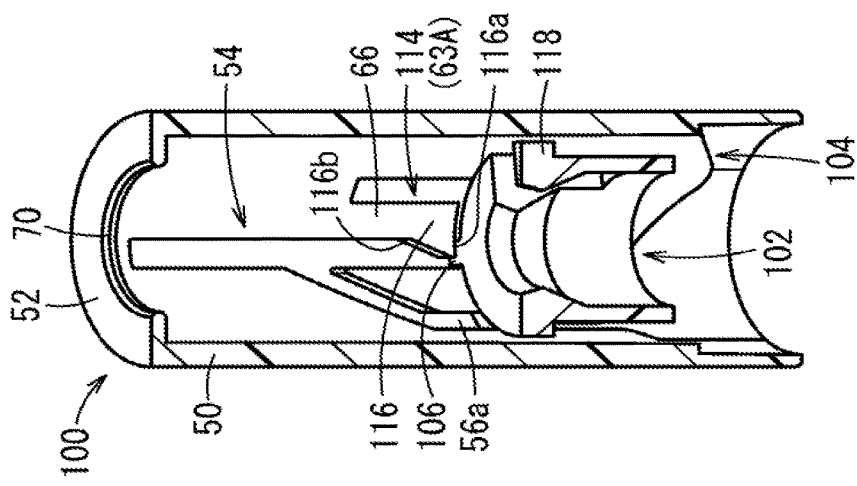
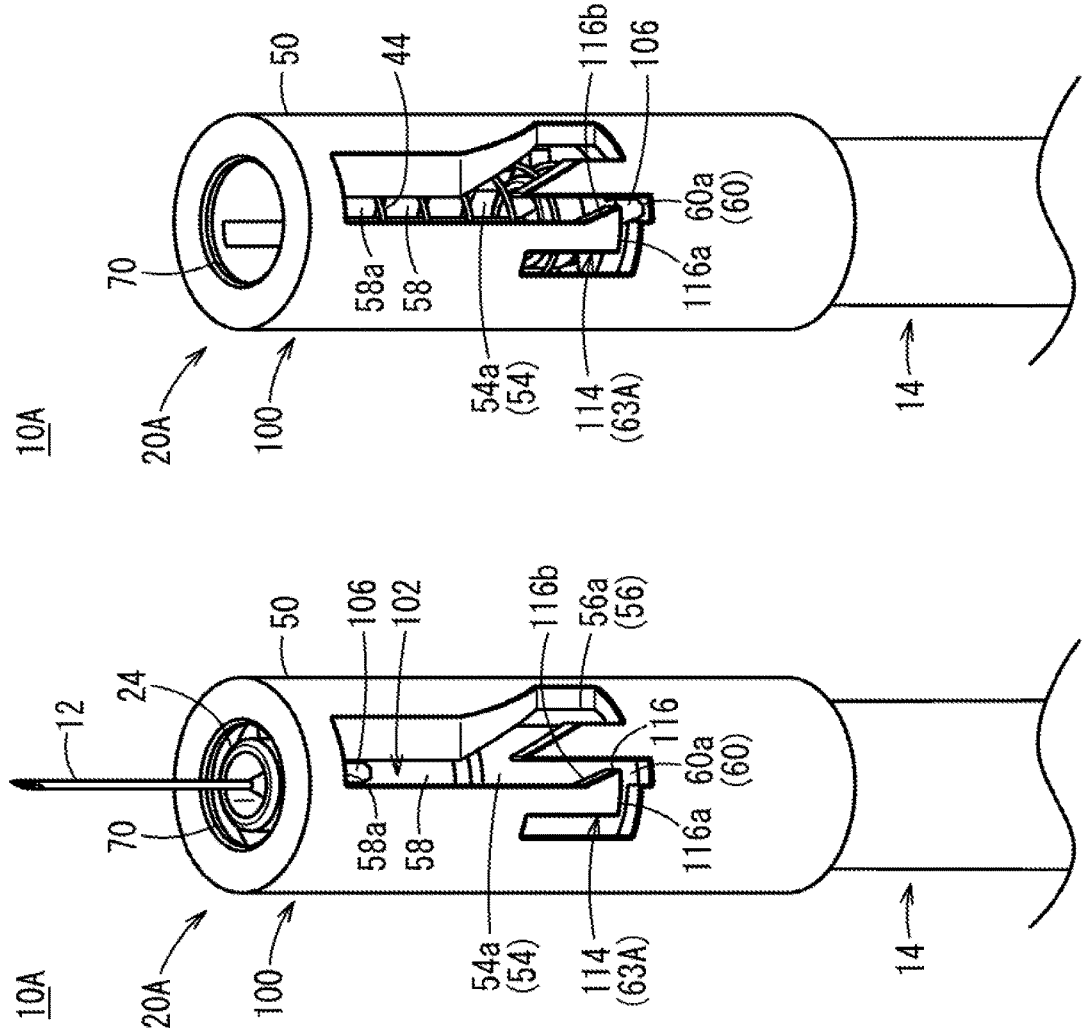

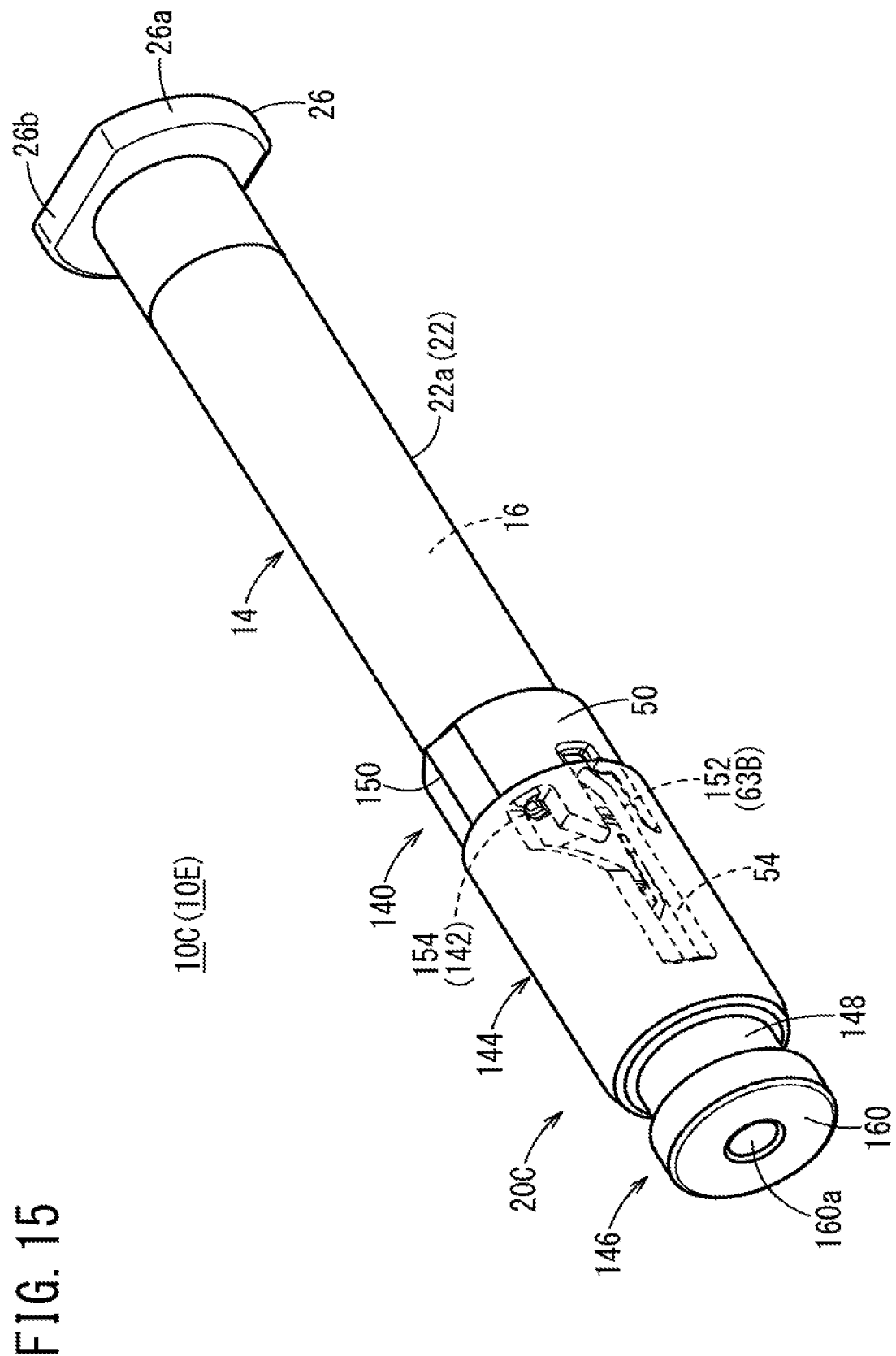

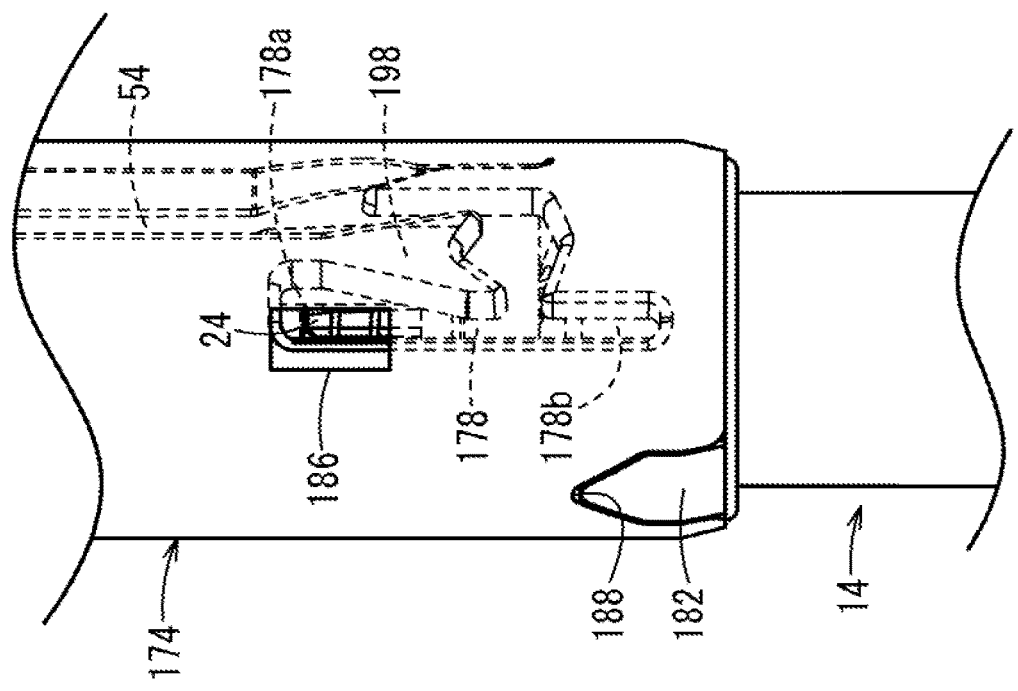
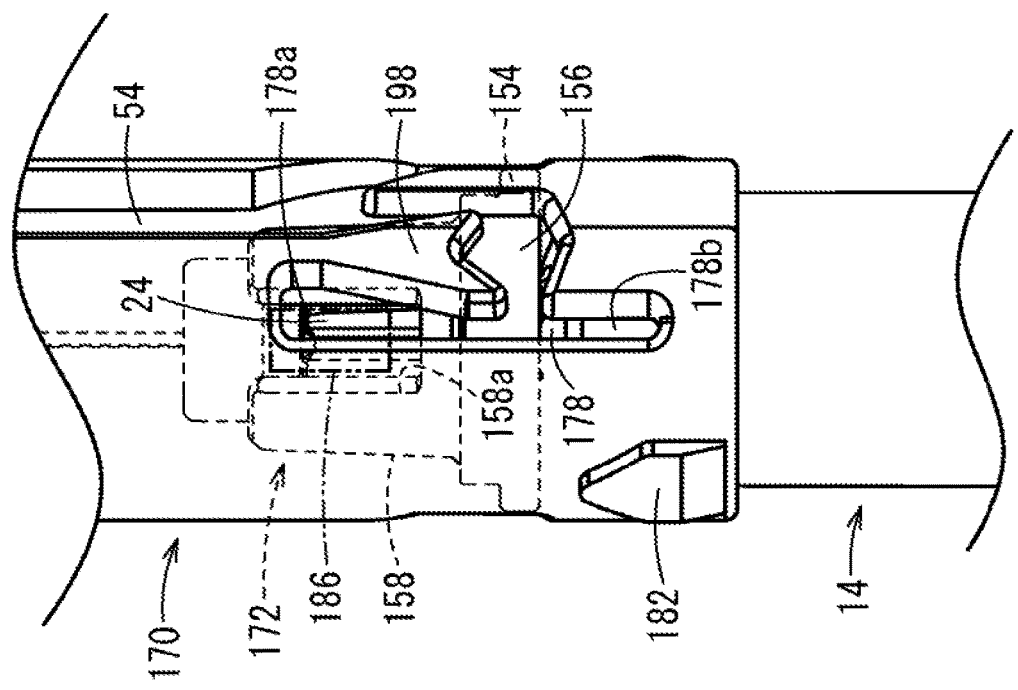

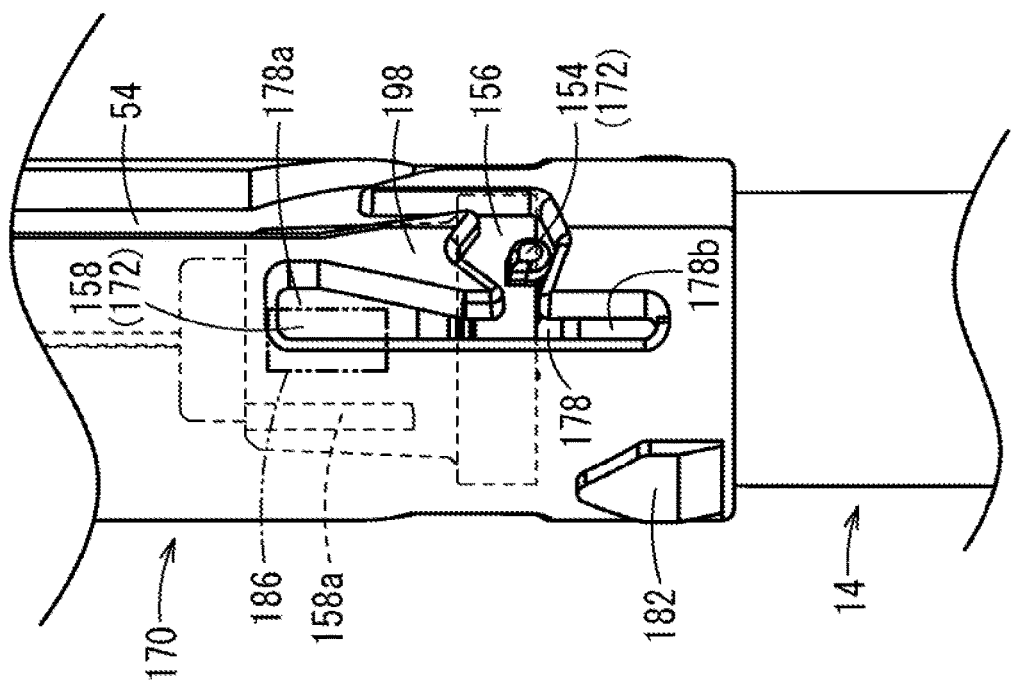
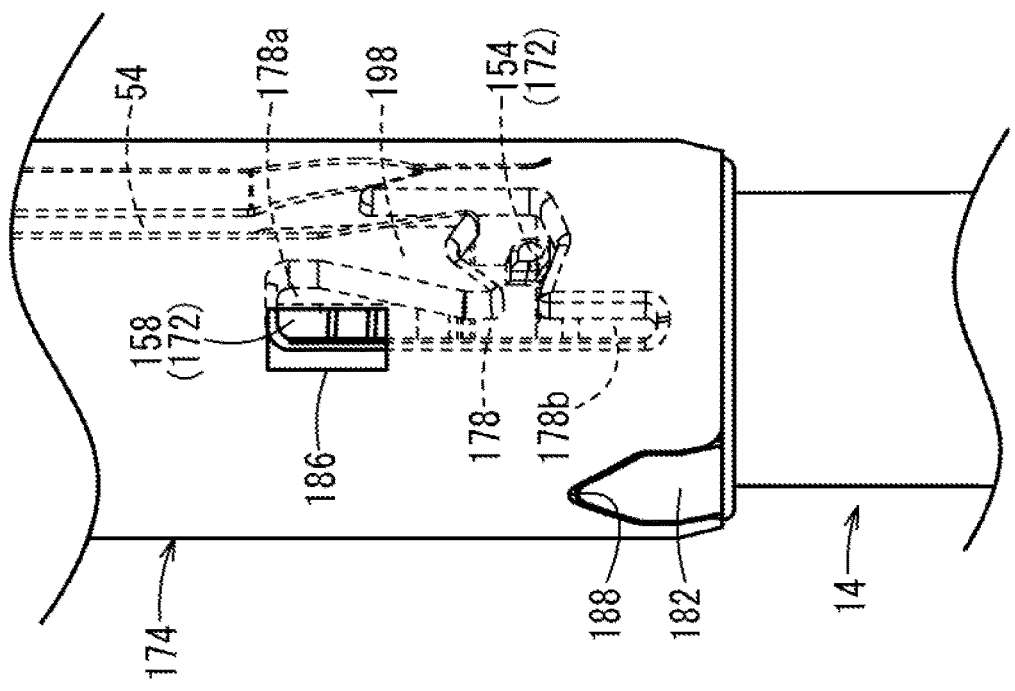

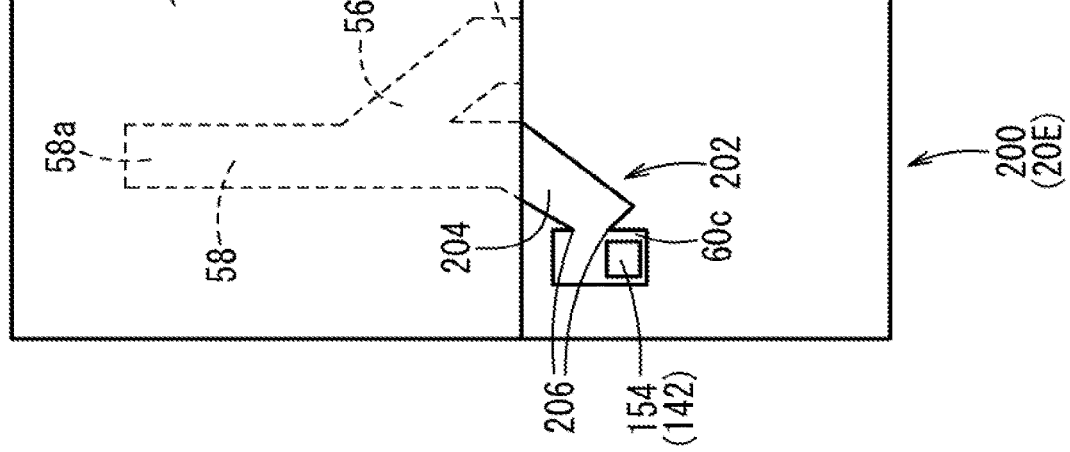
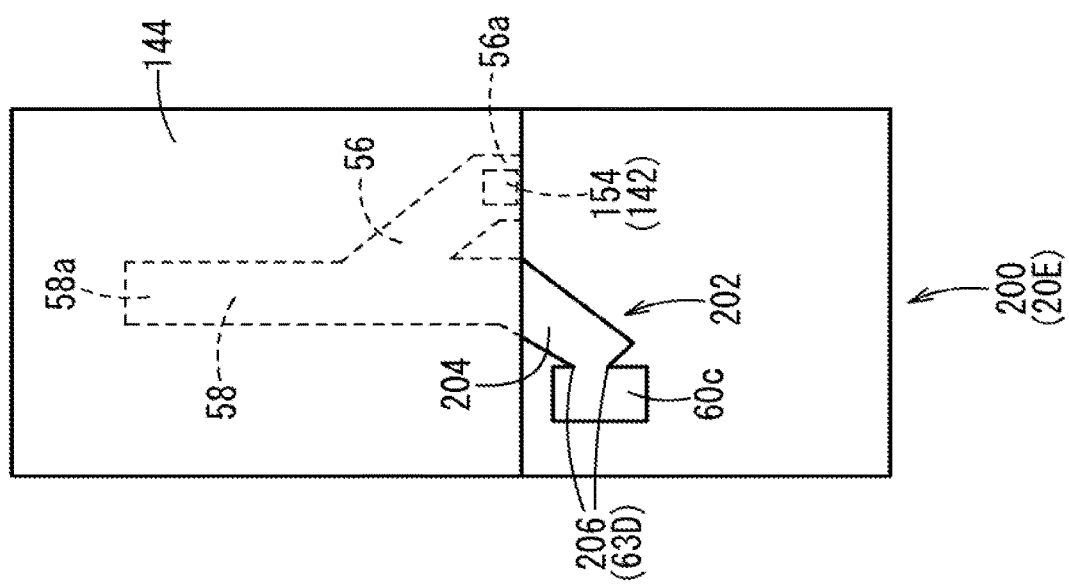

INJECTOR

CROSS-REFERENCE TO RELATED APPLICATIONS

This application is a continuation of U.S. patent application Ser. No. 14/664,205, filed on Mar. 20, 2015, which is a continuation application filed under 35 U.S.C. 111(a) claiming the benefit under 35 U.S.C. §§ 120 and 365(c) of PCT International Application No. PCT/JP2014/059019 filed on Mar. 27, 2014, which is based upon and claims the benefit of priority of Japanese Application No. 2013-168618 filed on Aug. 14, 2013, the entire contents of which are hereby incorporated by reference in their entireties.

BACKGROUND

Technical Field

The present disclosure relates to an injector that injects an injection solution by puncturing a puncture target with a needle.

Related Art

As one type of injectors, prefilled syringes that are provided in a state in which a medication (injection solution) is filled therein in advance are known. Among the prefilled syringes of such a type, prefilled syringes each including a protection device that prevents careless puncturing due to the exposure of a needle before or after the puncturing have been developed.

For example, in JP 2011-513035 W, a configuration has been disclosed in which the whole injector including the needle is covered with an outer housing (outer cylinder: protection device). This injector exposes a needle tip by moving forward the injector with respect to the outer housing based on a predetermined operation in a puncturing process, thereby puncturing a puncture target. After a medicine is injected into the puncture target, the injector automatically retreats with respect to the outer housing so as to be re-housed. As a result, the exposure of the punctured needle is prevented.

Meanwhile, from the viewpoint of handleability (for example, easiness in storage or conveyance, the operability, and the like), it is preferable that the injector is appropriately small. However, for the needle and a filling portion for a medicine, a size corresponding thereto is necessary, and thus, there is a limitation on a decrease in the size. Particularly, as disclosed in JP 2011-513035 W, there is concern that the size of the injector that includes a protection device is large according to the structure thereof.

SUMMARY OF INVENTION

One objective of certain embodiments of the present invention is to provide an injector capable of decreasing the size of the injector as much as possible by employing a simpler configuration of the protection device and improving the handleability together with the safety level.

According to one embodiment, an injector includes: a hollow needle; a main body unit including a needle holding portion that holds the needle; and a protection device configured to cover the needle before and after puncturing a puncture target with the needle. The protection device includes: an inner member attached to the needle holding portion and being freely rotatable around an outer periphery of the needle holding portion; and an outer member configured to (i) cover an outer side of the needle and the inner member before puncturing, (ii) expose the needle by moving toward a proximal end side relative to the main body unit at a time of puncturing, and (iii) cover a distal end of the needle by moving toward a distal end side relative to the main body unit after puncturing. The inner member includes a projection that protrudes toward the outer member. The outer member includes: a guide passage having the projection arranged therein and configured to rotate the inner member by guiding the projection to a predetermined section when the outer member is moved from before the puncturing to after the puncturing; and a restriction portion configured to restrict movement of the outer member toward the proximal end side with respect to the main body unit by being engaged with the inner member when the projection is moved to the predetermined section.

According to the above-described injector, the injector can rotate the inner member by operating the projection arranged in the guide passage when the outer member is moved at the time of puncturing by the needle using the projection arranged in the inner member and the guide passage arranged in the outer member. Accordingly, an arrangement relation for engaging the restriction portion of the outer member and the inner member with each other can be smoothly built, and, in the state in which the needle is housed in the outer member after puncturing, the movement of the outer member toward the proximal end side can be restricted well. Thus, the injector can prevent the exposure of the needle from the outer member after puncturing, and accordingly, the safety level is improved.

In addition, because the inner member can be configured in a short shape (small size) matching the size of the needle holding portion, the size of the entire injector can be decreased. In this way, the storage and the transportation of the injector can be performed in an easy manner, and the operability of the needle is improved according to the distal end portion of the injector that is configured to be short, whereby the puncturing process using the needle can be efficiently performed with high accuracy.

In one aspect, the inner member and the outer member are cylindrical, and an axial length of the inner member is shorter than a length of the guide passage in a direction parallel to an axis of the outer member.

As above, because the axial length of the inner member is shorter than the length of the guide passage, the inner member can be configured to be sufficiently short with respect to the outer member, and accordingly, the injector can be formed in a shape matching the needle holding portion in a simple manner.

In one aspect, the needle holding portion includes a support cylinder portion, and an expanded cylinder portion that is arranged at a distal end of the support cylinder portion and has an outer diameter larger than an outer diameter of the distal end of the support cylinder portion, and the inner member has an attachment portion that is configured to be engaged with a connection portion of the support cylinder portion and the expanded cylinder portion.

In such a case, the inner member attached to the connection portion of the support cylinder portion and the expanded cylinder portion is prevented from being separated from the expanded cylinder portion, and the inner member can be stably rotated around the outer periphery of the needle holding portion.

In one aspect, the main body unit includes a trunk portion that extends from a proximal end of the needle holding portion, and the inner member includes a cylinder portion that has an outer diameter that is equal to or less than an outer diameter of the trunk portion and the projection that protrudes from the cylinder portion toward the outer member.

In such a case, because the cylinder portion of the inner member has an outer diameter to be equal to or less than the outer diameter of the trunk portion, the size of the entire injector can be further decreased.

In one aspect, the main body unit further includes a hanging portion that is formed at a proximal end side of the main body unit and that protrudes in a direction that is substantially perpendicular to the axis of the main body unit, and an outer diameter of the outer member is smaller than a maximum outer diameter of the hanging portion.

As above, in a case where the injector is housed (hung) in the storage packaging due to the outer diameter of the outer member being smaller than the maximum outer diameter of the hanging portion, it can be suppressed that the outer member is caught, and only the hanging portion can be hung in a simple manner.

In one aspect, the guide passage includes: a before-puncturing section at which the projection is arranged before puncturing; a puncturing section to which the projection is movable at the time of puncturing, the puncturing section being located distal of the before-puncturing section; and an after-puncturing section to which the projection is movable after puncturing, the after-puncturing section being located proximal of the puncturing section, and having a phase in a peripheral direction of the outer member deviating with respect to the before-puncturing section, and the after-puncturing section corresponding to the predetermined position. The restriction portion includes a hook portion that restricts movement of the outer member toward the proximal end side by being engaged with the inner member when the projection is moved to the after-puncturing section.

As above, because the hook portion is caught in the inner member at the after-puncturing section, the injector can restrict the backward movement of the outer member using the inner member in a simple manner.

In one aspect, the hook portion includes a convex portion that protrudes to an inner side in a diameter direction of the outer member. The inner member further includes: an engagement portion that is engageable with the convex portion when the projection is located at the after-puncturing section; and a passage allowing portion configured such that the convex portion is passable therethrough from a distal end to a proximal end of the inner member. The engagement portion and the passage allowing portion have phases deviating from each other in the peripheral direction of the inner member.

As above, because the phases of the engagement portion and the passage allowing portion deviate from each other in the peripheral direction of the inner member, the injector can easily change the positional relation between the passage allowing portion and the engagement portion with respect to the convex portion of the outer member according to the rotation of the inner member.

In one aspect, the hook portion includes an elastic piece in which the convex portion is arranged, and the injector is configured such that, when the projection is moved from the puncturing section to the after-puncturing section, the convex portion advances over the engagement portion by elastically deforming the elastic piece to an outer side in a radial direction.

As above, because the convex portion advances over the engagement portion by elastically transforming the elastic piece to the outer side in the diameter direction, the injector can smoothly perform relative movement of the outer member with respect to the inner member.

In one aspect, the hook portion includes a claw portion that protrudes to the inside of the guide passage near a distal end of the after-puncturing section and that is configured to restrict movement of the outer member to the proximal end side by engaging with the projection that is moved to the after-puncturing section.

As above, because the claw portion is caught in the projection, the injector does not need to arrange a structure protruding to the inner side of the outer member, and accordingly, the size of the protection device can be further decreased.

In one aspect, the hook portion includes an elastic piece, in which the claw portion is arranged, adjacent to the guide passage between the puncturing section and the after-puncturing section, and the projection is configured to advance over the claw portion by elastically deforming the elastic piece when the projection is moved from the puncturing section to the after-puncturing section.

As above, because the projection advances over the claw portion by elastically transforming the elastic piece, the injector can smoothly perform relative movement of the outer member with respect to the inner member.

In one aspect, the claw portion includes a V-shaped groove that is open toward the after-puncturing section on a side opposing the after-puncturing section, and the injector is configured such that, when the projection located at the after-puncturing section is moved toward the puncturing section, the projection is led to a bottom portion of the V-shaped groove by being brought into contact with the V-shaped groove.

As above, by leading the projection to the V-shaped groove, the engagement between the projection and the claw portion becomes stronger.

In one aspect, a cover that restricts deformation of the elastic piece to an outer side is arranged on an outer peripheral surface of the outer member.

As above, by arranging the cover on the outer peripheral surface of the outer member, the injector can restrict the deformation of the elastic piece toward the outer side, and it can be prevented that the claw portion is separated from the inner member, and the engagement is released.

In one aspect, a gap is formed between an inner surface of the cover and an outer surface of the claw portion.

As above, when the slight gap is formed between the inner surface of the cover and the outer surface of the claw portion, the inner surface of the cover does not interfere with the outer surface of the claw portion that is elastically transformed, and it becomes easy for the claw portion to be elastically transformed, whereby the projection of the inner member can easily advance over the claw portion.

In one aspect, the injector further comprises a sealing member that has a hollow portion housing the needle and a sealing portion sealing the distal end of the needle on an inside thereof. The outer member has a sealing member holding portion that detachably holds the sealing member, and the sealing member, when held by the sealing member holding portion before puncturing, seals the hollow portion as a proximal end portion of the sealing member is brought into contact with a distal end portion of the needle holding portion.

As above, because the injector has the sealing member, the needle can be formed in a tightly sealed state by using the hollow portion and the sealing portion before puncturing. In addition, the sealing member held by the sealing member holding portion can prevent relative movement of the outer member with respect to the main body unit before puncturing.

In one aspect, the outer member includes a hollow part that houses the needle and the inner member, and a leading groove portion is formed on an inner surface of the outer member, the leading groove portion being configured to lead the projection to the guide passage when the inner member is inserted into the hollow part from the proximal end side.

As above, because the outer member includes the leading groove portion, the injector can smoothly lead the projection of the inner member to the guide passage in the assembly of the protection device, and accordingly, the assembly operation can be efficiently performed. In addition, in the assembly process, damages and the like in the outer member and the inner member can be suppressed.

In one aspect, the leading groove portion includes: a first groove that is formed in a linear shape parallel to an insertion direction of the inner member toward the guide passage near a proximal end of the guide passage; and a second groove that is inclined in a rotation direction of the inner member to the distal end side toward the first groove that is continuous from a proximal end side of the first groove.

As above, by configuring the leading groove portion by using the first groove and the second groove, when the inner member is inserted into the outer member from the proximal end side of the outer member, first, the inner member can be moved to the first groove by guiding the projection along the second groove. Then, the projection that has been moved to the first groove enters the guide passage and is arranged in a simple manner. In addition, when the main body unit holding the needle under the guide of the first groove and the inner member are inserted, the needle can be stuck straight into the sealing member.

In one aspect, the guide passage includes: a before-puncturing section at which the projection is arranged before puncturing; a puncturing section to which the projection is movable at the time of puncturing, the puncturing section being located distal of the before-puncturing section; and an after-puncturing section to which the projection is movable after puncturing, the after-puncturing section being located proximal of the puncturing section and being in a position different from the before-puncturing section in an axial direction of the outer member. A cover is arranged on an outer peripheral surface of the outer member. When the projection is located at one of the before-puncturing section and the after-puncturing section, the cover covers an entirety of the outer peripheral surface of the inner member. When the projection is located at the other of the before-puncturing section and the after-puncturing section, the cover allows at least a part of the inner member to protrude distally or proximally from the cover.

As above, by causing at least a part of the inner member to protrude from the cover toward the further distal end side or the further proximal end side than the cover, the user using the injector can check the non-used state or the use-completed state of the injector by checking the state of the inner member.

In one aspect, a cover having a window portion through which an inside of the outer member is visually perceivable is arranged on an outer peripheral surface of the outer member. An external appearance of the inner member that is visually perceivable through the window portion has a first appearance when the injector is in a state before rotation of the inner member and has a second appearance different from the first appearance in a state after rotation of the inner member.

As above, in a case where the window portion is arranged in the cover, the injector can allow an external appearance that is different between before and after the rotation of the inner member to be visually recognized without employing a configuration for exposing the inner member from the cover, and accordingly, the user can recognize whether the injector is in the non-used state or the use-completed state.

According to embodiments of the present invention, by employing a simpler configuration of a protection device, the size of the injector is decreased as much as possible, and the handleability can be further improved together with the safety level.

BRIEF DESCRIPTION OF DRAWINGS

FIG. 7 is a side cross-sectional view of the storage packaging illustrated in FIG. 6.

FIG. 8A is a first schematic diagram that illustrates the operation of the injector illustrated in FIG. 1 in a puncturing process, FIG. 8B is a second schematic diagram of the injector following FIG. 8A, FIG. 8C is a third schematic diagram of the injector following FIG. 8B, and FIG. 8D is a fourth schematic diagram of the injector following FIG. 8C.

FIG. 12A is a first schematic diagram that illustrates an operation performed when a protection device illustrated in FIG. 10 is assembled, FIG. 12B is a second schematic diagram of the protection device following FIG. 12A, and FIG. 12C is a third schematic diagram of the protection device following FIG. 12B.

FIG. 13A is a first schematic diagram that illustrates the operation of the injector illustrated in FIG. 10 in the puncturing process, FIG. 13B is a second schematic diagram of the injector following FIG. 13A, and FIG. 13C is a cross-sectional perspective view that illustrates a relation between the outer cylinder and the inner cylinder illustrated FIG. 13B.

FIG. 15 is a perspective view that illustrates the whole configuration of an injector according to a fourth embodiment.

FIG. 23A is an enlarged side view that illustrates the operation of a window portion of the injector illustrated in FIG. 19 before the puncturing process, and FIG. 23B is a side view that illustrates a state in which the cover illustrated in FIG. 23A is excluded.

FIG. 24A is an enlarged side view that illustrates the operation of the window portion of the injector illustrated in FIG. 19 after the puncturing process, and FIG. 24B is a side view that illustrates a state in which the cover illustrated in FIG. 24A is excluded.

FIG. 25A is a first schematic diagram that illustrates an outer cylinder and a cover of an injector according to a sixth embodiment, and FIG. 25B is a second schematic diagram that illustrates the operation of a projection according to the outer cylinder illustrated in FIG. 25A.

DETAILED DESCRIPTION

Hereinafter, injectors according to preferred embodiments (first to sixth embodiments) of the present invention will be described in detail with reference to the accompanying drawings.

First, an overview of certain embodiments of an injector according to the present invention will be presented. The injector, as described above, is configured as a prefilled syringe in which a medicine (injection solution) is filled in advance. By providing a protection device covering a needle for this injector, leakage of the medicine is prevented, and the degree of hygiene and the safety level before a puncturing process can be improved.

When the injector is used, the needle is exposed from the protection device by a user, and the injector punctures a patient who is a puncture target with the needle and gives (injects) the medicine to the patient. After the medicine is given, the injector is separated from the patient by the user and automatically rehouses the exposed needle in the protection device. Thus, the safety level of the injector after the puncturing process can be improved as well. Here, the user using the injector is not limited to a medical doctor, a nurse, or the like but includes the patient. In addition, the injector is not limited to the prefilled syringe but may employ a system in which a medicine solution is filled after the product is provided.

First Embodiment

Figure 1:
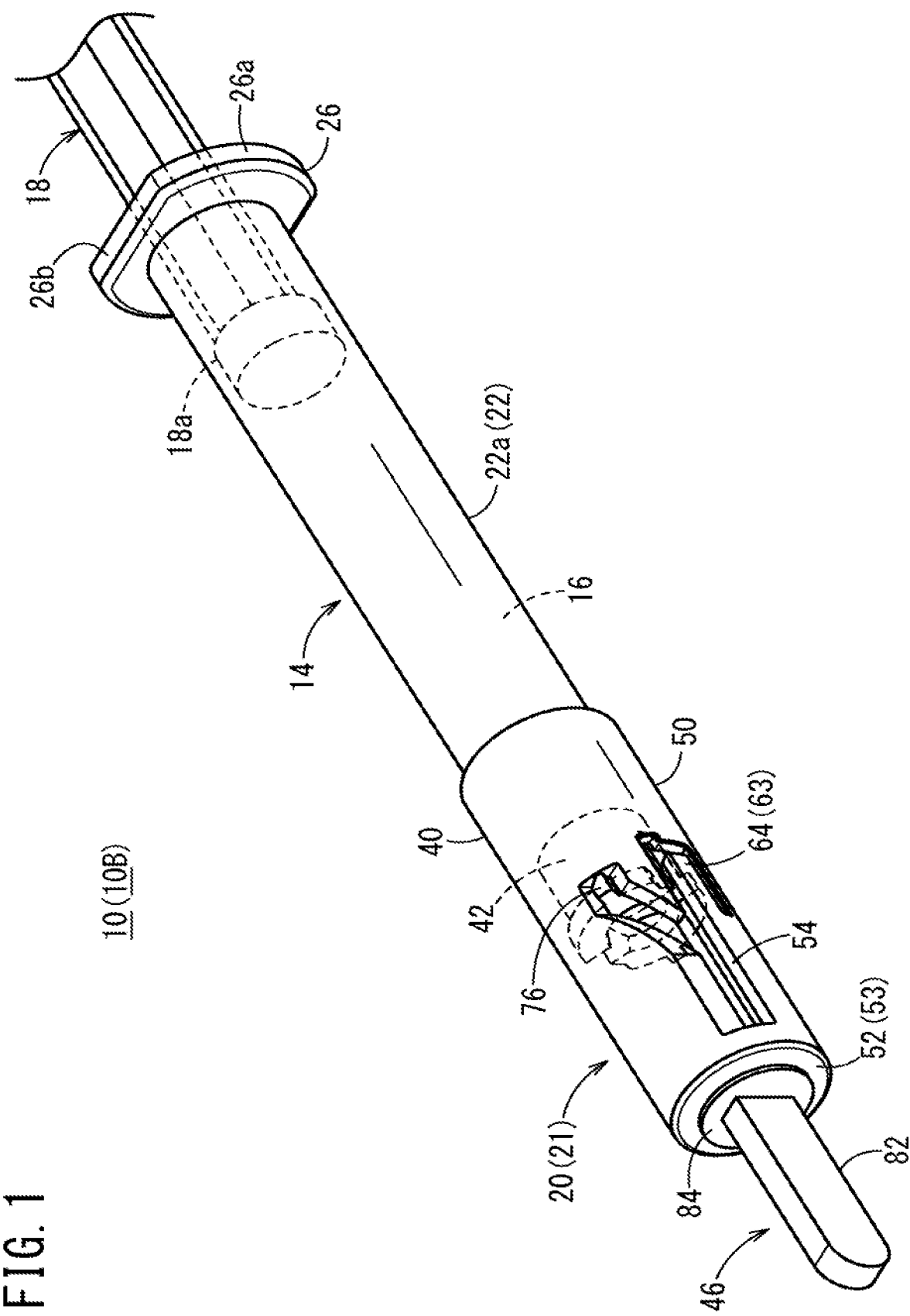
FIG. 1 is a perspective view that illustrates the whole configuration of an injector according to a first embodiment.
Figure 2:
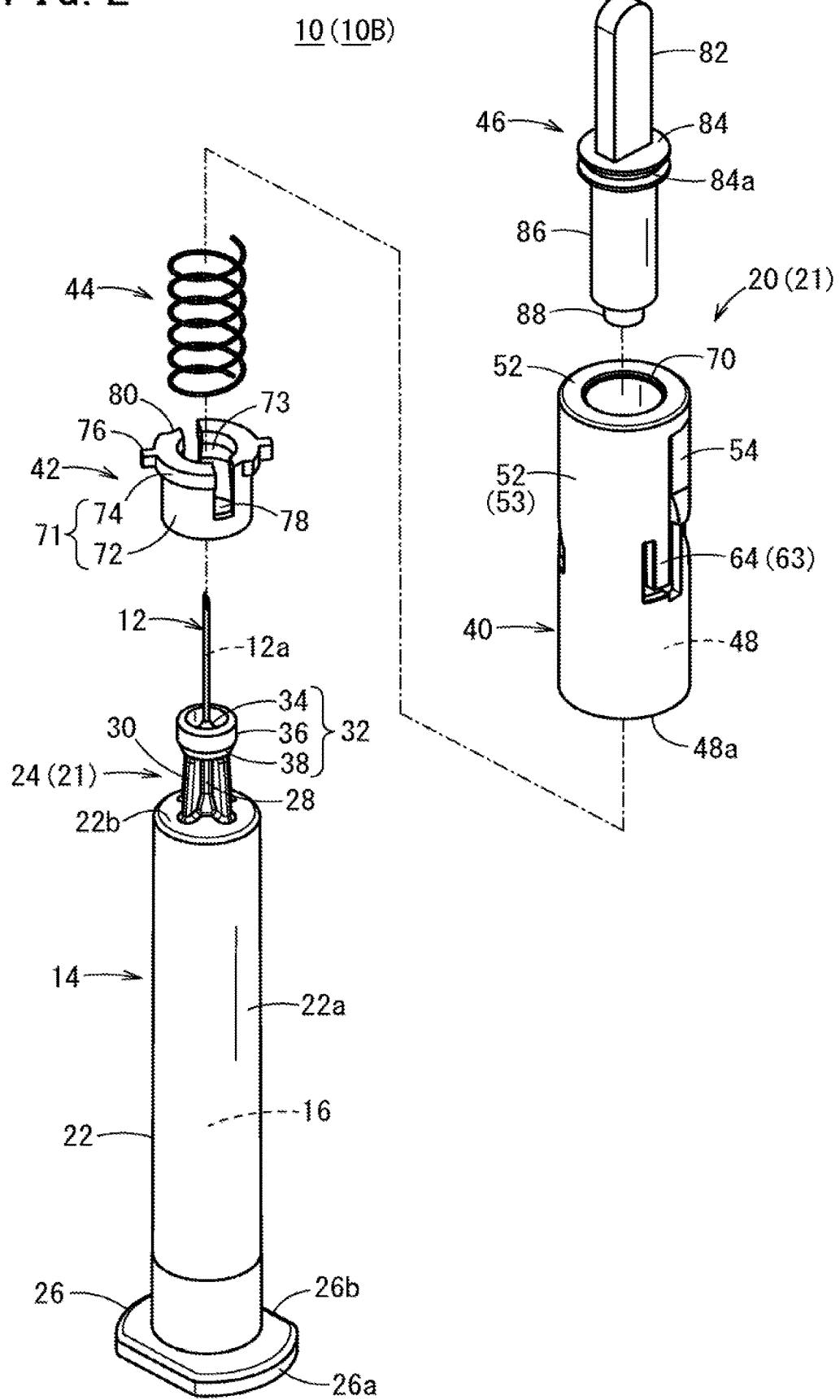
FIG. 2 is an exploded perspective view of the injector illustrated in FIG. 1.

An injector 10 according to the first embodiment, as illustrated in FIGS. 1 and 2, includes: a needle 12 that punctures a patient; a main body unit 14 that has a storage space 16 in which a medicine is stored; and a plunger 18 that is inserted into the storage space 16 and is movable relative to the main body unit 14. In addition, in the injector 10, as described above, a protection device 20 that covers the needle 12 before and after the puncturing process is arranged. Hereinafter, the protection device 20 side will be described as a distal end side of the injector 10, and the plunger 18 side will be described as the proximal end side of the injector 10.

It is preferable that the needle 12 of the injector 10 is configured in a cylindrical shape having a fine diameter for which the patient does not feel much pain, and the distal end portion (needle tip) thereof may be formed to be sharp so as to be easily inserted under the skin. Inside the needle 12, a derivation passage 12a capable of discharging the medicine from the distal end is formed.

The main body unit 14 includes: a trunk portion 22 that has the storage space 16 on the inside thereof; a needle holding portion 24 that is arranged on the distal end side of the trunk portion 22; and a hanging portion 26 that is arranged on the proximal end side of the trunk portion 22. Each portion is integrally molded when the main body unit 14 is manufactured.

The trunk portion 22 exhibits a cylindrical shape and is formed to have a predetermined axial length and a predetermined diameter dimension according to the storage amount of the medicine of the storage space 16. The trunk portion 22 includes a peripheral wall 22a of a cylindrical shape that encloses the side periphery of the storage space 16 and an end wall 22b, which forms a bottom portion of the storage space 16, configured to be continuous from the distal end of the peripheral wall 22a. The hanging portion 26 is formed to extrude from the proximal end side outer peripheral surface of the peripheral wall 22a toward the outer side and is configured to hook a user's finger when the plunger 18 is operated. In addition, the outer edge of the hanging portion 26 is formed by two arc portions 26a facing each other and two linear portions 26b facing each other. The needle holding portion 24 is connected to the end wall 22b.

Figure 3A:
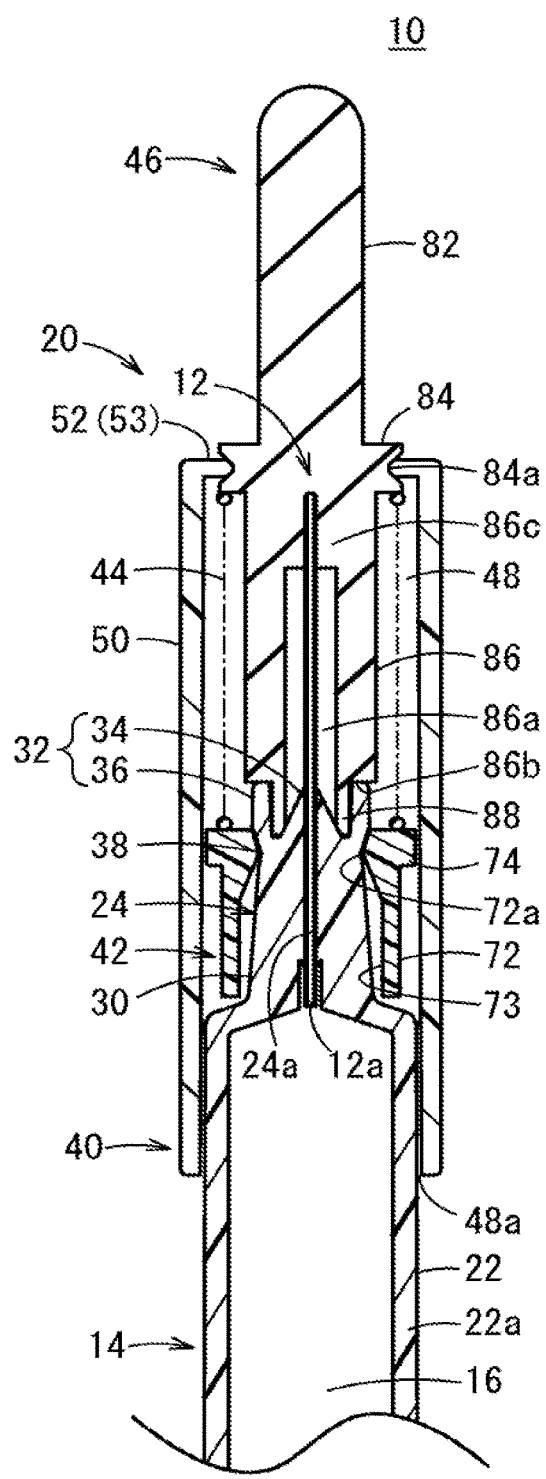
FIG. 3A is a side cross-sectional view that illustrates a distal end portion of the injector illustrated in FIG. 1.

The needle holding portion 24, as illustrated in FIGS. 2 and 3A, is a portion that holds the needle 12 and protrudes toward the distal end side so as to have the same axial center as the axial center of the trunk portion 22. In the axial center portion of the needle holding portion 24, a holding hole 24a is arranged, which has an inner diameter matching the outer diameter of the needle 12 and is formed to pass through from the distal end portion to the storage space 16. The amount of protrusion of the needle holding portion 24 is set such that both a length for reliably holding the needle 12 along the axial direction of the injector 10 and shortening (decrease in size) for improving the handleability of the injector 10 are achieved. For this reason, in order to reliably hold the needle 12 in a relatively short distance, the needle holding portion 24 includes a support cylinder portion 28 on the proximal end side and an expanded cylinder portion 32 on the distal end side. In addition, the axial length of the needle holding portion 24 is shorter than the axial length of a portion of the needle 12 that protrudes to the distal end side more than the needle holding portion 24.

The support cylinder portion 28 is formed to be sufficiently thin relative to the main body unit 14, and the holding hole 24a is arranged along the axial direction on the inside thereof. The needle 12 is fixed to and held by the support cylinder portion 28 by using an appropriate fixing method in a state in which the needle 12 is inserted into the holding hole 24a. As the method of fixing the needle 12, there is insert molding, thermal welding using a high frequency or a laser beam, bonding using an adhesive, or the like.

In addition, the support cylinder portion 28 includes bearing ribs 30 on the periphery thereof. Four bearing ribs 30 are arranged in the peripheral direction of the outer peripheral surface of the support cylinder portion 28 at the interval of 90° and protrude in a direction of the normal line of the support cylinder portion 28. Each bearing rib 30 is formed along the axial direction of the support cylinder portion 28 from the end wall 22b to the expanded cylinder portion 32, and the thickness thereof is set to be thinner than the outer diameter of the support cylinder portion 28. In addition, the protrusion height of each bearing rib 30 from the support cylinder portion 28 toward the outer side of the direction of the normal line is set to be gently lowered from the proximal end toward the distal end, and the lowest distal end is connected to the expanded cylinder portion 32.

The expanded cylinder portion 32 is formed to have a twofold cylindrical structure such that the needle 12 is held, and a cap 46 of the protection device 20 to be described later can be attached thereto. More specifically, the expanded cylinder portion 32 includes: a center support portion 34 that holds the needle 12 in the center portion; an outer surrounding portion 36 that surrounds the side of the center support portion 34; and a constriction portion 38 that is formed in a tapered shape on the proximal end side of the outer surrounding portion 36.

The center support portion 34 is formed in an approximately conical shape and has the holding hole 24a formed to pass through the apex and the axial center portion thereof. The outer surrounding portion 36 is separated from the center support portion 34 such that the cap 46 can be inserted therebetween. The distal end side of the outer surrounding portion 36 expands to the outer side of each bearing rib 30 in the diameter direction. The constriction portion 38 is formed as the proximal end side of the outer surrounding portion 36 becomes narrow toward each bearing rib 30 and is connected to the distal end of each bearing rib 30. The constriction portion 38 formed in a tapered shape in this way has a function of rotating an inner cylinder 42 of the protection device 20 outside the needle holding portion 24. Here, the constriction portion 38 may not be in a tapered shape but may be formed in a stepped manner between the outer surrounding portion 36 (support cylinder portion 28) and each bearing rib 30 (expanded cylinder portion 32).

The protection device 20 attached to the injector 10 configures a safety mechanism 21 preventing careless exposure of the needle 12 together with the needle holding portion 24. This protection device 20 is assembled by including an outer cylinder 40 (outer member) that convers the needle 12 and an inner cylinder 42 (inner member) that is attached to the needle holding portion 24 as its main configuration and further including a spring 44 (biasing member) and the cap 46 (sealing member).

The outer cylinder 40 of the protection device 20, as illustrated in FIGS. 3A, 3B, 4A, and 4B, is formed in an external form having a diameter larger than the trunk portion 22 of the main body unit 14. More specifically, the outer diameter of the outer cylinder 40 is set to be smaller than a maximum outer diameter of the hanging portion 26. Here, the maximum outer diameter of the hanging portion 26 is the outer diameter of a virtual circle having a maximum distance from the axis of the trunk portion 22 to the outer edge of the hanging portion 26 as its radius on a plane perpendicular to the axis of the trunk portion 22 and, in the first embodiment, is an outer diameter of a virtual circle including one pair of the arc portions 26a.

Inside the outer cylinder 40, a hollow part 48 is arranged which can house the needle 12 attached to the needle holding portion 24 and the distal end side of the inner cylinder 42, or the trunk portion 22. The distal end side of the hollow part 48 includes a space receiving the needle holding portion 24 or the inner cylinder 42 in the state before the puncturing process using the needle 12. For this reason, the outer cylinder 40 is movable toward the proximal end side with respect to the needle 12, the main body unit 14, and the inner cylinder 42. In addition, the outer cylinder 40 includes a side wall 50 of a cylinder shape and an upper bottom wall 52 that protrudes to the inner side in the diameter direction at the distal end portion of the side wall 50.

The side wall 50 encloses the side periphery of the hollow part 48 and has an axial length longer than the needle 12. On the proximal end side of the side wall 50, a proximal end opening 48a that communicates with the hollow part 48 is arranged. The inner diameter of the side wall 50 is set to be slightly larger than the outer diameter of the trunk portion 22, and accordingly, the smoothness of the forward/backward movement of the outer cylinder 40 and a decrease in the size of the protection device 20 (outer cylinder 40) are realized. In addition, on the distal end side from an approximately middle portion of the side wall 50, one pair of guide passages 54 is formed.

The guide passages 54 are arranged at opposing positions with the hollow part 48 being interposed therebetween and are formed to be long in the axial direction. Each guide passage 54 enables the hollow part 48 and the outside of the outer cylinder 40 to communicate with each other and has a function of guiding a projection 76 of the inner cylinder 42 to be described later. The guide passage 54 branches on the further proximal end side than an axial-direction middle section 54a and becomes a series of long holes extending in a linear shape on the further distal end side than the axial-direction middle section 54a.

More specifically, the guide passage 54 includes a first passage 56 that obliquely extends from the axial-direction middle section 54a in the peripheral direction toward the proximal end side and extends to some extent from the middle section toward the proximal end side. The proximal end side of the first passage 56 becomes a before-puncturing section 56a at which the projection 76 is arranged before the puncturing process performed by the needle 12. A first lateral side 56*b* configuring the inclined portion of the first passage 56 is notched so as to be open obliquely with respect to the guide passage 54 and is configured to decrease a contact portion (friction) that is in contact with the projection 76.

In addition, the guide passage 54 includes a second passage 58 that is configured to be continuous from the distal end portion (axial-direction middle section 54*a* of the guide passage 54) of the first passage 56 and extends in a linear shape toward the distal end side. The distal end side of the second passage 58 becomes a puncturing section 58*a* to which the projection 76 moves at the time of the puncturing process performed by the needle 12. A first lateral side 58*b* configuring the second passage 58, similar to the first lateral side 56*b* of the first passage 56, is notched to be obliquely open.

Furthermore, the guide passage 54 includes a third passage 60 that is configured to be continuous from the distal end portion (the proximal end portion of the second passage 58: the axial-direction middle section 54*a* of the guide passage 54) of the first passage 56 and extends in a linear shape toward the proximal end side. The proximal end side of the third passage 60 becomes an after-puncturing section 60*a* to which the projection 76 moves after the puncturing process is performed by the needle 12. The first passage 56 and the third passage 60 intersect at a predetermined angle (for example, 45° or less), and an apex 54*b* of the side wall 50 is formed at the intersection.

In addition, from a middle section of the third passage 60 on the proximal end side, a notched groove 62 acquired by notching the side wall 50 in the shape of "L" is configured to be continuous. The notched groove 62 slightly extends in the peripheral direction of the side wall 50 and further extends from the peripheral end thereof toward the distal end side by a predetermined length (to be longer than the extension made in the peripheral direction). According to this notched groove 62, a hook portion 64 (restriction portion 63) that can be elastically displaced is formed on the side wall 50 adjacent to the third passage 60.

The hook portion 64 includes an elastic piece 66 that displaces the proximal end side in the diameter direction by being connected to the side wall 50 at the distal end and a locking convex portion 68 that is formed to protrude on the inner side of the elastic piece 66. The elastic piece 66 has an elastic force that can appropriately displace the proximal end side according to the axial length of the notched groove 62. The locking convex portion 68 includes a locking surface 68*a*, which is disposed on the proximal end side, that is formed in the shape of an approximately rectangle triangle in the side sectional view and protrudes in a direction perpendicular to the inner surface of the elastic piece 66 and an inclined surface 68*b*, which is disposed on the distal end side, inclined from the apex of the locking surface 68*a* toward the elastic piece 66. The locking surface 68*a* has a function of catching the inner cylinder 42. Here, the hook portion 64 may not be arranged at a position adjacent to the guide passage 54 but may be arranged at a position located far from the guide passage 54. For example, the hook portion 64 may be formed by a notched groove (not illustrated) acquired by notching the side wall 50 in the shape of "U" at a position different from that of the guide passage 54 in the peripheral direction.

On the other hand, the upper bottom wall 52 of the outer cylinder 40 forms an opening portion 70 narrower than the inner diameter of the hollow part 48 by forming the distal end inner side of the side wall 50 to protrude along the peripheral direction. This opening portion 70 communicates with the hollow part 48, exposes the needle 12 at the time of performing the puncturing process, and is sealed by the cap 46 before the puncturing process. In other words, the upper bottom wall 52 has a function as a sealing member holding portion 53 for holding the cap 46. In addition, the proximal end surface of the upper bottom wall 52 is formed in a flat shape as a seat for receiving the distal end portion of the spring 44. Here, the sealing member holding portion 53 may be formed inside the outer cylinder 40 disposed on the further proximal end side than the upper bottom wall 52 or the like instead of being arranged on the upper bottom wall 52. In such a case, the forming position of an attachment projection portion 84 of the cap 46 to be described later may be appropriately matched, and the sealing member holding portion 53 may serve also as the seat of the spring 44.

Figure 3B:
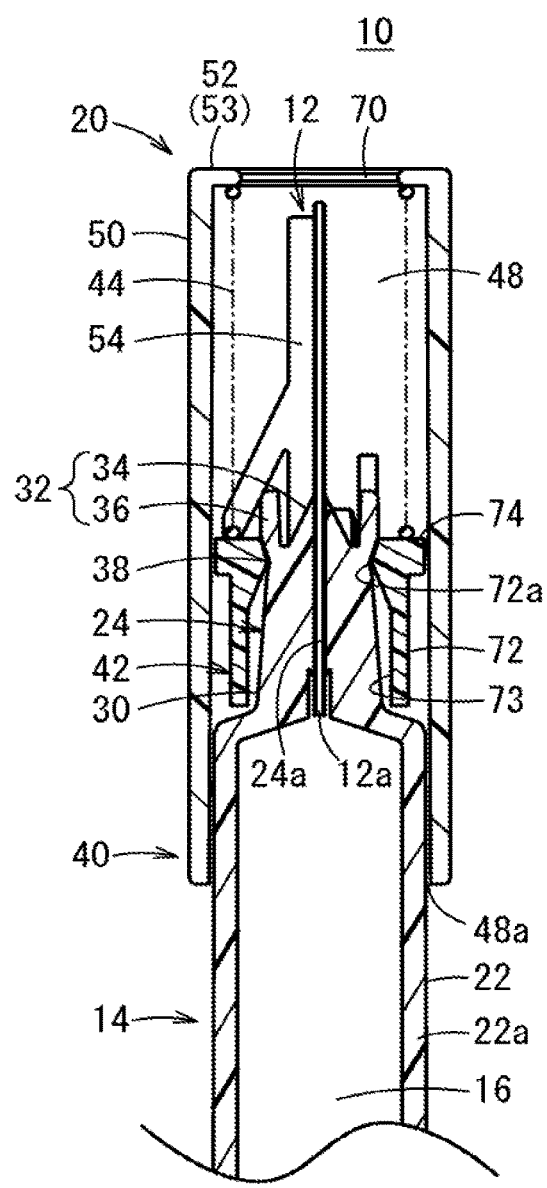
FIG. 3B is a side cross-sectional view that illustrates a detached state of a cap of the injector illustrated in FIG. 3A.
Figure 4A:
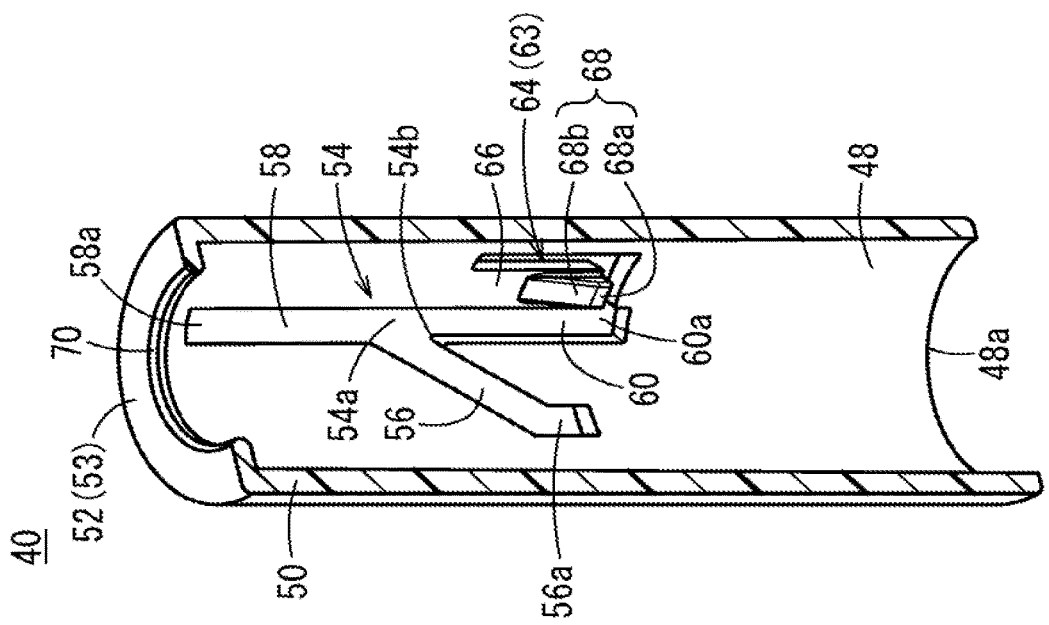
FIG. 4A is a perspective view that illustrates an outer cylinder illustrated in FIG. 1.
Figure 4B:
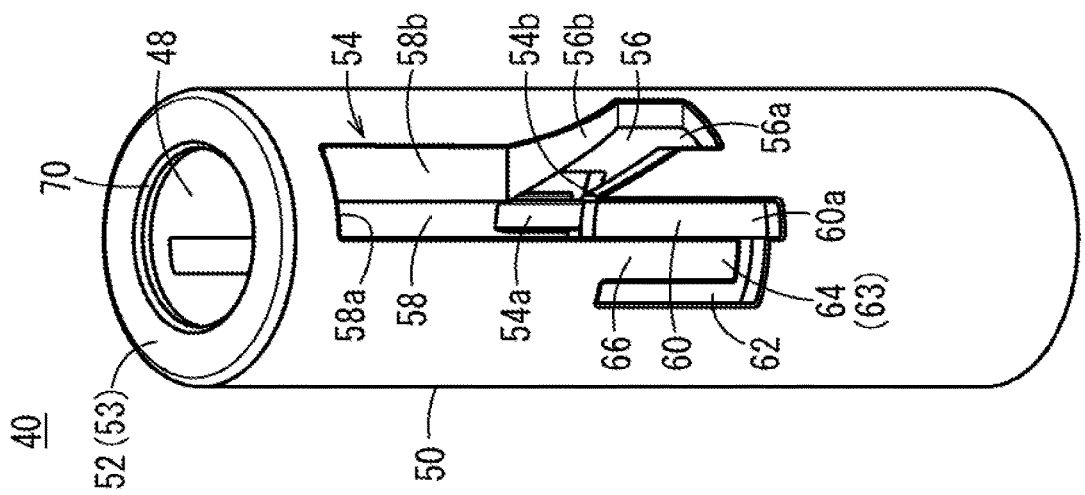
FIG. 4B is a cross-sectional perspective view of the outer cylinder illustrated in FIG. 4A.
Figure 5A:
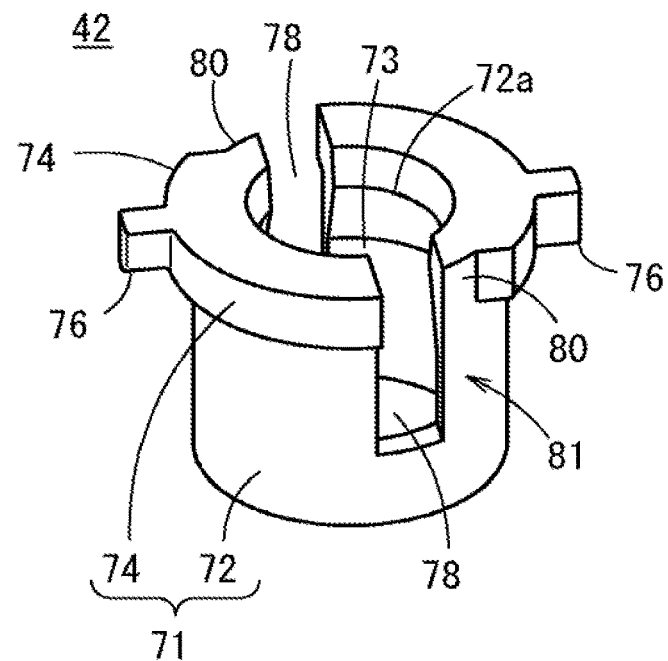
FIG. 5A is a perspective view that illustrates an inner cylinder illustrated in FIG. 1.

The inner cylinder 42 of the protection device 20, as illustrated in FIGS. 3A, 3B, and 5A, includes: an attached cylinder portion 71 that is arranged on the periphery of the needle holding portion 24; and a projection 76 that protrudes from a predetermined position on the cylinder portion 71 to the outer side in the diameter direction. In addition, the cylinder portion 71 includes: a base portion 72 that surrounds the side of the needle holding portion 24; and flange portions 74 (engagement portions) that are formed at the distal end of the base portion 72. The axial length of the inner cylinder 42 is shorter than the length (a length acquired by adding the second passage 58 and the third passage 60) of the guide passage 54 in a direction parallel to the axis of the outer cylinder 40 and is shorter than the axial length of the needle holding portion 24. Accordingly, the axial length of the inner cylinder 42 is shorter than that of a configuration in which a guide passage is arranged in an inner cylinder, and a projection is arranged in an outer cylinder, whereby the whole size of the injector 10 is decreased.

The base portion 72 of the inner cylinder 42 is formed in a cylindrical shape, and, in an axial center portion thereof, an attachment hole 73, into which the needle holding portion 24 is inserted, passing through in the axial direction is arranged. In the inner peripheral surface configuring the attachment hole 73, the proximal end side is formed to have a diameter larger than that of the needle holding portion 24 (expanded cylinder portion 32), and an elevated portion 72*a* (attachment portion) corresponding to the constriction portion 38 is formed on the distal end side. The elevated portion 72*a* gradually decreases the diameter of the attachment hole 73 from an approximately middle portion of the base portion 72 toward the distal end side and gradually increases the diameter toward the distal end side with an apex that approximately matching the outer diameter of the constriction portion 38 being used as a starting point. The inner cylinder 42 is assembled by engaging the elevated portion 72*a* with the constriction portion 38 of the needle holding portion 24. Here, the assembling of the needle holding portion 24 and the inner cylinder 42 is not limited to the above-described configuration, but, for example, it may be configured such that the elevated portion 72*a* is omitted, and the distal end of the inner cylinder 42 is engaged with the constriction portion 38 by configuring the inner diameter of the attachment hole 73 to be smaller than the support cylinder portion 28 (outer surrounding portion 36). In such a case, the constriction portion 38 may be not in a tapered shape but a simple level difference that is formed between the support cylinder portion 28 and the expanded cylinder portion 32.

In addition, on the outer peripheral surface of the base portion 72, one pair of base portion notched portions 78 that are notched by a predetermined depth from the distal end toward the proximal end are formed. The base portion notched portions 78 are arranged at opposing positions with the axial center of the base portion 72 being interposed therebetween. When the inner cylinder 42 is installed to the needle holding portion 24, the base portion notched portion 78 separates the upper portions of the cylinder portion 71 from each other and easily moves the elevated portion 72a to a position opposing the constriction portion 38. Here, the inner cylinder 42 may be formed in a shape (in other words, in the shape of "C" in the cross-section) notched from the distal end to the proximal end by one notched portion. In such a case, when the inner cylinder 42 is installed to the needle holding portion 24, the inner cylinder 42 can be installed not only from the distal end side but also in a direction perpendicular to the axis of the needle holding portion 24.

The flange portions 74 protrude from the distal end of the base portion 72 to the outer side in the diameter direction and are formed in arc shapes along the peripheral direction of the base portion 72. One pair of the flange portions 74 are arranged on both the base portions 72 divided by the base portion notched portion 78. The flange portions 74 protrude to the outermost side of the inner cylinder 42 in the diameter direction. The amount of protrusion of each flange portion 74 is set such that the outer peripheral surface of the flange portion 74 is in proximity with the inner peripheral surface (the side wall 50) of the outer cylinder 40. Accordingly, when the outer cylinder 40 is moved forward or backward, the direction of the forward/backward movement is guided by the flange portion 74 while sliding resistance for the flange portion 74 is sufficiently suppressed. In addition, it is preferable that the outer diameter of the flange portion 74 (the cylinder portion 71) is equal to or less than the outer diameter of the trunk portion 22. In this way, because the shape of the outer cylinder 40 can be set such that the inner peripheral surface of the outer cylinder 40 is in proximity with the outer peripheral surface of the trunk portion 22, an increase in the size of the outer cylinder 40 is suppressed, whereby a decrease in the size of the whole injector 10 is achieved.

At predetermined positions (near the connection to one side of each of the base portion notched portions 78) on the outer peripheral surface of the flange portion 74, one pair of flange notching portions 80 exposing the outer peripheral surface of the base portion 72 by notching the flange portions 74 are formed. These flange notching portions 80 become a passage allowing portion 81 that allows the hook portion 64 to pass when the outer cylinder 40 is moved backward.

Figure 9A:
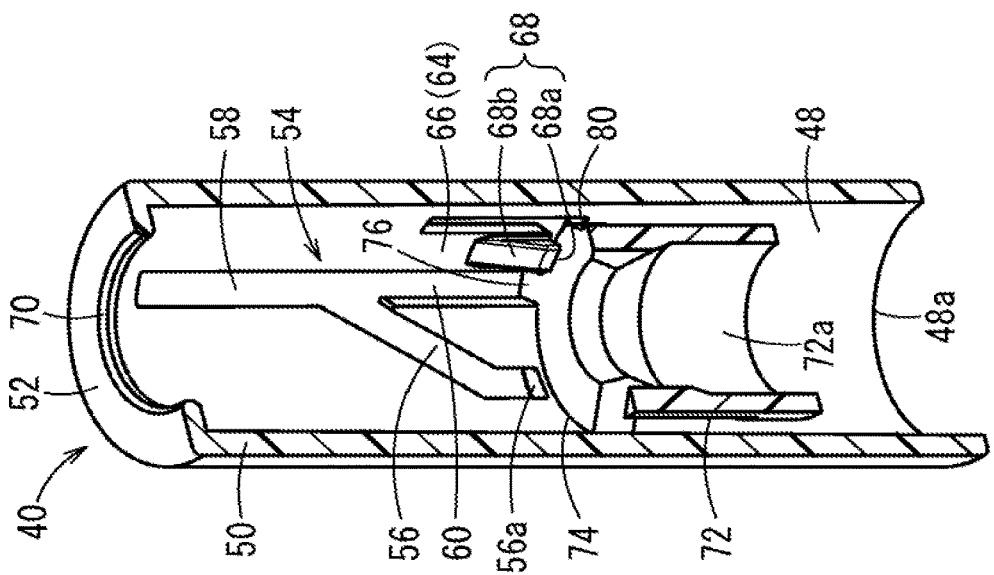
FIG. 9A is a cross-sectional perspective view that illustrates the states of the outer cylinder and the inner cylinder before the puncturing process.
Figure 9B:
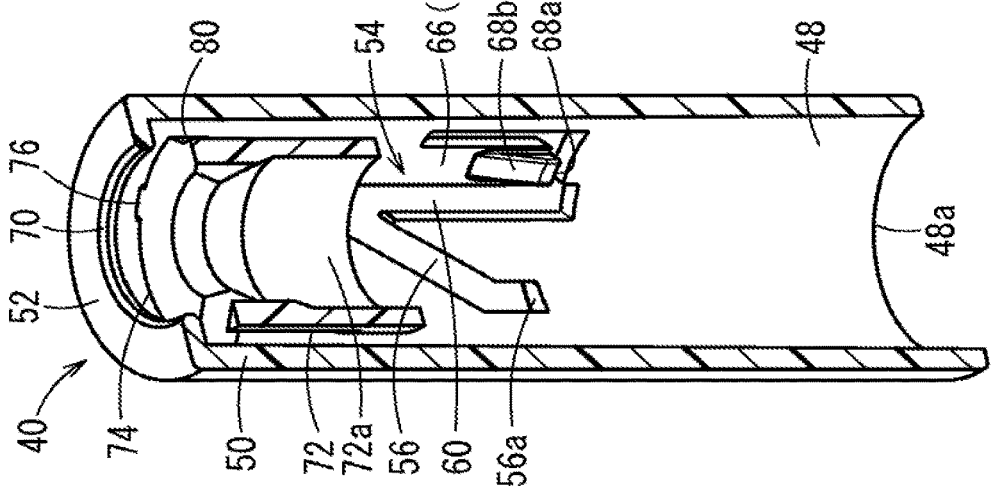
FIG. 9B is a cross-sectional perspective view that illustrates the states of the outer cylinder and the inner cylinder in the puncturing process.
Figure 9C:
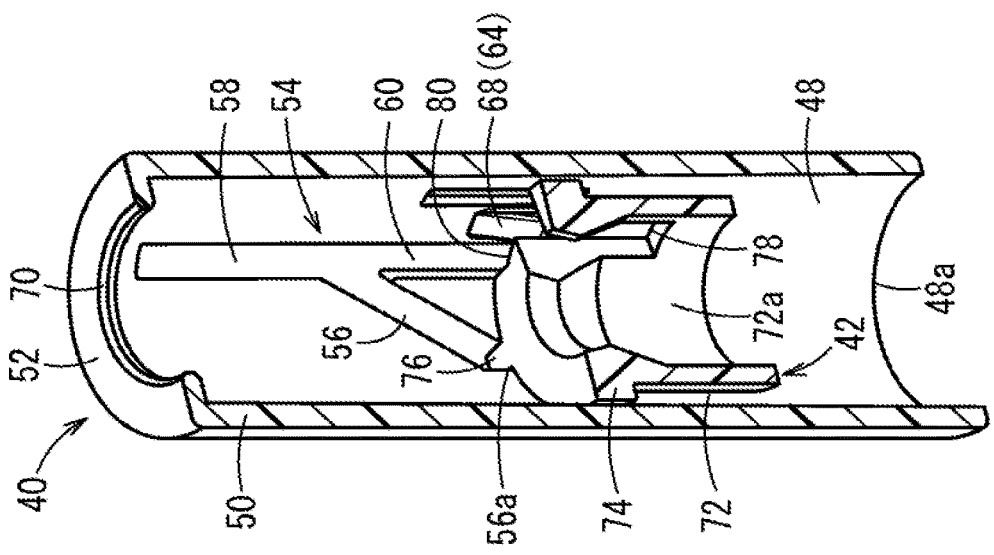
FIG. 9C is a cross-sectional perspective view that illustrates the states of the outer cylinder and the inner cylinder after the puncturing process.

The passage allowing portion 81 is a space of the cylinder portion 71 for preventing the hook portion 64 (the locking convex portion 68) from being caught and includes the outer side of the base portion 72, the base portion notched portion 78, and the flange notching portion 80 (see FIGS. 9A to 9C). Here, the configuration of the passage allowing portion 81 is not limited to the above-described configuration, and, for example, in a case where the locking convex portion 68 of the outer cylinder 40 is located at a position overlapping the base portion notched portion 78 in a state in which the projection 76 is located at the before-puncturing section 56a, the flange notching portion 80 may not be arranged.

Figure 5B:
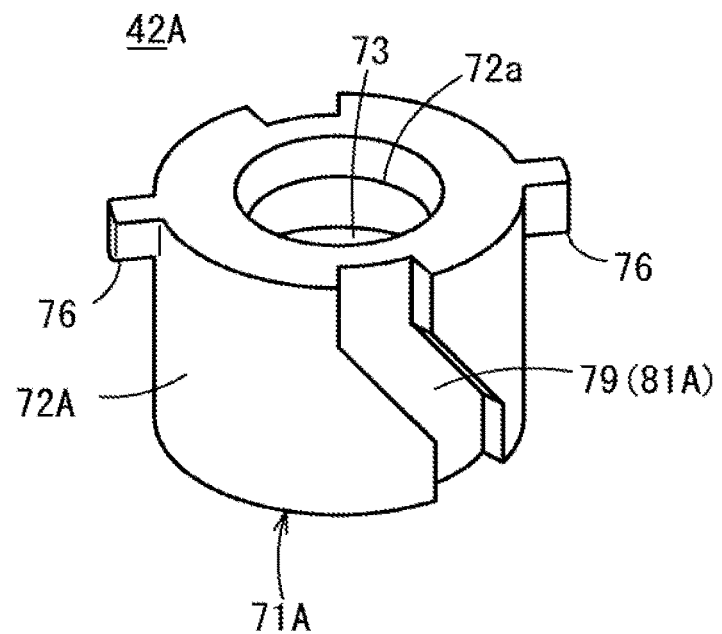
FIG. 5B is a perspective view of the inner cylinder according to a modified example.

In addition, similar to a modified example illustrated in FIG. 5B, it may be configured such that the cylinder portion 71A of the inner cylinder 42A does not include the flange portion 74, but the outer diameter of the base portion 72A itself is set to be at the same level as that of the flange portion 74. In such a case, the passage allowing portion 81A may be formed as a groove portion 79 acquired by notching the outer peripheral surface of the base portion 72A. The shape of the groove portion 79 is appropriately set in accordance with the movement amount of the outer cylinder 40 in the axial direction and the rotation amount of the inner cylinder 42A. In addition, the projection 76 may be configured to protrude from a predetermined position on the outer peripheral surface of the base portion 72A.

Referring back to FIG. 5A, the projections 76 are formed at predetermined positions (positions having a phase difference of 90° in a peripheral direction with respect to the base portion notched portions 78) on the outer peripheral surfaces of the one pair of the flange portions 74. The projections 76 protrude to the outer side of the inner peripheral surface of the outer cylinder 40 in the diameter direction and are inserted into the guide passage 54 of the outer cylinder 40 in the state of being attached to the outer cylinder 40. Each of the projections 76 is formed in a prism shape. In addition, on a side opposite to the rotation direction of the inner cylinder 42 on the proximal end side of the projection 76, an inclined portion 76a (see FIG. 8A) inclining in the rotation direction toward the proximal end side with respect to the axial direction of the inner cylinder 42 is formed.

Here, the shape of the projection 76 is not particularly limited but may be formed in a column shape or the like. In addition, the flange portions 74 and the projections 76 may be appropriately arranged not only on the distal end side of the cylinder portion 71 but also in the cylinder portion 71 according to the shape of the guide passage 54, the position of the hook portion 64 (the locking convex portion 68), and the like. In such a case, the flange portion 74 may be arranged only in a portion that is engaged with the hook portion 64 (the locking convex portion 68).

The distal end surface of the inner cylinder 42 is configured by lining up the base portion 72 and the flange portion 74. This distal end surface is formed in a flat shape and becomes a seat for stably receiving the proximal end portion of the spring 44.

The spring 44 of the protection device 20, as illustrated in FIGS. 2, 3A, and 3B, is arranged between the proximal end surface of the upper bottom wall 52 of the outer cylinder 40 and the distal end surface of the inner cylinder 42. In order not to expose the needle 12 before the puncturing process, the spring 44 has an axial length for separating the upper bottom wall 52 of the outer cylinder 40 from the distal end surface of the inner cylinder 42 by a predetermined distance. This spring 44 is contracted when the outer cylinder 40 is moved backward at the time of performing the puncturing process by biasing the outer cylinder 40 toward the distal end side and forwardly moves the outer cylinder 40 toward the distal end side by elastically returning after the puncturing process.

In addition, the cap 46 of the protection device 20 is formed using a rubber material or the like and is installed in the opening portion 70 of the outer cylinder 40 before the puncturing process. This cap 46 includes a knob portion 82, an attachment projection portion 84, and an extended cylinder portion 86 from the distal end side toward the proximal end side. The knob portion 82 is a portion that is used for user's gripping when the cap 46 is detached from the outer cylinder 40 and has a protrusion amount and a thickness that are appropriate for easy gripping.

The attachment projection portion 84 is formed to protrude to the outer side in the diameter direction so as to be engaged with the upper bottom wall 52 of the outer cylinder 40 at the axial-direction middle section of the cap 46. More specifically, the attachment projection portion 84 is formed in a disk shape having a thickness larger than the upper bottom wall 52, and, on the side peripheral surface, an attachment groove 84a is installed along the peripheral direction. In the state in which the outer cylinder 40 and the cap 46 are attached together, as the upper bottom wall 52 (the opening edge of the opening portion 70) is fitted into the attachment groove 84a, the attachment projection portion 84 seals the opening portion 70 in a liquid-tight manner. The attachment projection portion 84 formed using rubber is relatively easily detached from the outer cylinder 40 when a pulling-out force is received from the knob portion 82.

The extended cylinder portion 86 protrudes from the proximal end surface of the attachment projection portion 84 toward the proximal end side, and, on the inside thereof, a hollow portion 86a having a predetermined depth along the axial direction is formed. In the state in which the outer cylinder 40 and the cap 46 are attached together, the needle 12 arrives at the distal end side of the hollow portion 86a through the hollow portion 86a, and the distal end thereof is inserted into a sealing portion 86c that is a body portion of the extended cylinder portion 86, whereby the distal end of the needle 12 is sealed. In this way, the cap 46 can reliably prevent the exposure of the needle tip and suppress the leakage of the medicine.

In addition, on the proximal end side of the extended cylinder portion 86, in the state in which the outer cylinder 40 and the cap 46 are attached together, a projection portion 88 that is inserted into a gap between the center support portion 34 and the outer surrounding portion 36 is arranged. The outer diameter of the projection portion 88 is formed to be smaller than the outer diameter of the extended cylinder portion 86, and the projection portion 88 is inserted into the gap in a relatively easy manner.

On the proximal end side of the extended cylinder portion 86, an opposing surface 86b opposing the outer surrounding portion 36 is formed by the above-described projection portion 88 having a small diameter. In the state in which the cap 46 is attached, the opposing surface 86b of the extended cylinder portion 86 and the needle holding portion 24 are brought into contact with each other, whereby careless backward movement of the outer cylinder 40 is prevented. In other words, even when it is attempted to move the outer cylinder 40 backward, the opposing surface 86b of the cap 46 attached to the outer cylinder 40 is supported by the needle holding portion 24, and accordingly, the backward movement of both the outer cylinder 40 and the cap 46 is restricted. In addition, the projection portion 88 is fitted into the proximal end (a valley portion of the center support portion 34 and the outer surrounding portion 36) of the outer surrounding portion 36, whereby the cap 46 can restrict the backward movement of the outer cylinder 40 more reliably.

As the opposing surface 86b and the distal end surface of the outer surrounding portion 36 are brought into tight contact with each other, and the outer peripheral surface of the projection portion 88 and the inner peripheral surface of the outer surrounding portion 36 are brought into tight contact with each other, the cap 46 can reliably seal the hollow portion 86a. It is needless to say that the tight contact portion may be only one of the above-described tight contact portions. In addition, as the projection portion 88 is inserted into the inner side of the outer surrounding portion 36, the cap 46 is prevented from deviating from the needle holding portion 24, whereby the tight contact state can be reliably maintained. By detaching the cap 46, the injector 10 is in a puncturing-enabled state.

Referring back to FIG. 1, because the injector 10 is a prefilled syringe, the plunger 18 of the injector 10 may be configured not to be installed before the use. In other words, the injector 10 having the storage space 16 filled with a medicine can be stored at an appropriate place in a state in which the proximal end side of the storage space 16 is sealed only by a gasket 18a.

Figure 6:
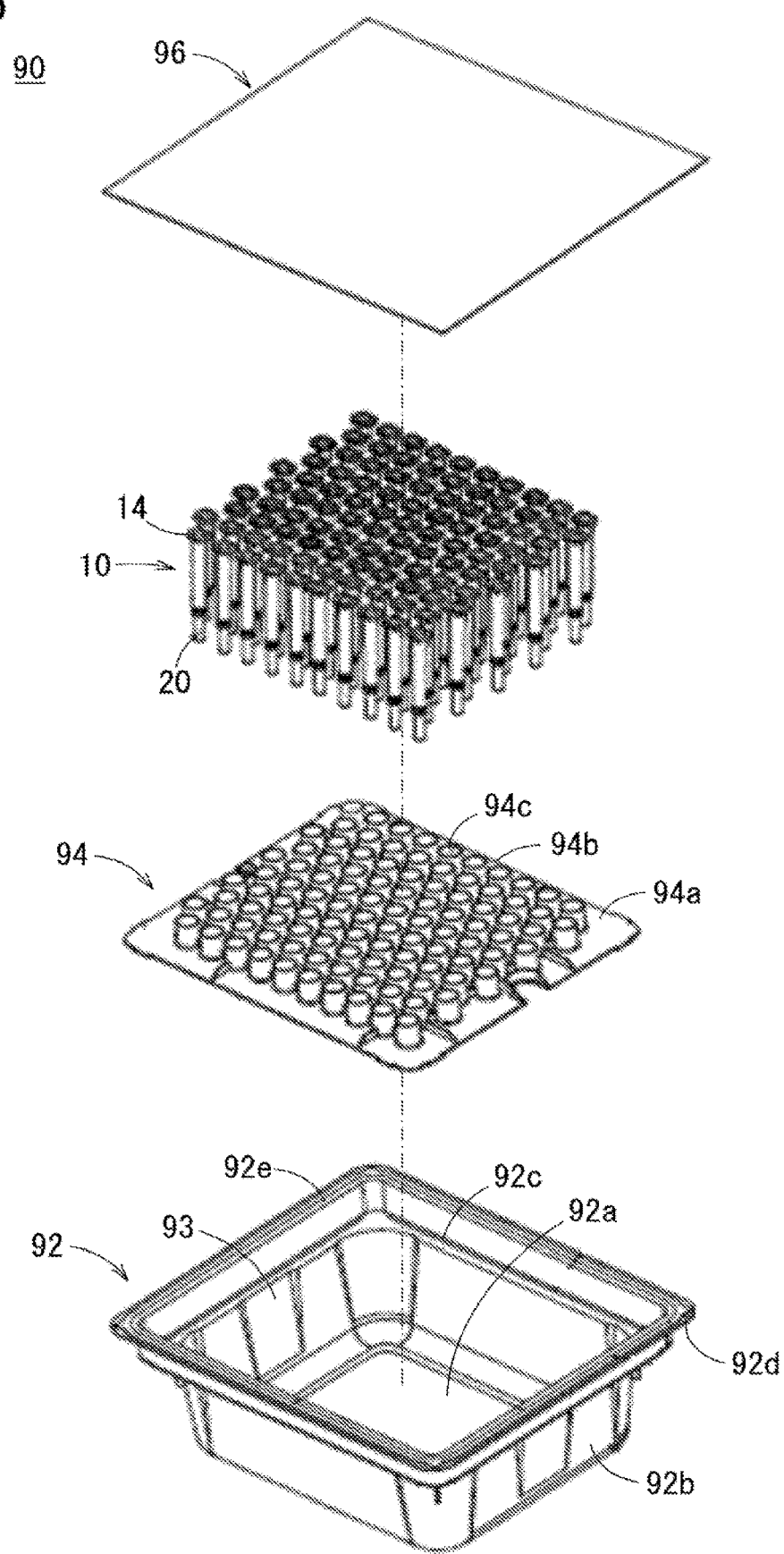
FIG. 6 is an exploded perspective view of a storage packaging that houses the injector illustrated in FIG. 1.

In addition, the injector 10 is transported or stored in a state before a medicine is filled as a prefilled syringe, in other words, in a state in which the gasket 18a and the plunger 18 are not attached. In this case, the injector 10, until the medicine is filled, is stored, for example, in a dedicated storage packaging 90 as illustrated in FIGS. 6 and 7. Hereinafter, the storage of the injector 10 before the medicine is filled as a prefilled syringe will be described more specifically. A plurality of the injectors 10 are arranged and housed in the storage packaging 90 in a sterilizable state or a tellurized state. As a method of sterilizing the injector 10, high-pressure steam sterilization, radiation or electron beam sterilization, or ethylene oxide gas sterilization may be applied.

The storage packaging 90, for example, includes a packaging body 92, a holding member 94, and a lid member 96. The packaging body 92 is formed in the shape of a box having an open upper surface and an internal space 93 enclosed by a bottom wall 92a and a surrounding wall 92b. The internal space 93 exhibits a shape for housing a plurality of the injectors 10 in a hanging state. In other words, the surrounding wall 92b enclosing the internal space 93 is formed to have a vertical length longer than the whole length of the injector 10. In a predetermined portion near the upper portion of the surrounding wall 92b, a level difference 92c expanding to the side (outer side) is arranged. The holding member 94 is placed in this level difference 92c. In addition, in the upper portion of the surrounding wall 92b, a side projection portion 92d protruding to the side is arranged. On the upper surface of the side projection portion 92d, a heat sealing convex portion 92e is arranged, and the lid member 96 is fixed by this heat sealing convex portion 92e.

The holding member 94 is a member that holds a plurality of the injectors 10 at the same height and includes a flat plate portion 94a that is formed in a planar shape corresponding to the level difference 92c of the packaging body 92 and a projection holding portion 94b that is arranged in a matrix shape on the flat plate portion 94a. The projection holding portion 94b protrudes from the upper surface of the flat plate portion 94a to the upper side and includes a hole portion 94c into which the trunk portion 22 of the injector 10 can be inserted. This hole portion 94c is formed to have a diameter that is narrower than the width of the hanging portion 26 (between one pair of the arc portions 26a) of the injector 10, and the projection holding portion 94b is caught in the hanging portion 26 so as to hang the injector 10.

The lid member 96 that covers the packaging body 92 is sealed with heat at the heat sealing convex portion 92e arranged in the side projection portion 92d so as to allow the peripheral edge portion thereof to be peeled off. In order to perform high-pressure steam sterilization or ethylene oxide gas sterilization, it is preferable that fine particles such as a germ and a virus cannot permeate through the lid member 96, and the lid member 96 has sterilization gas distributability for which sterilization gas such as water vapor or ethylene oxide gas can permeate through the lid member 96. As a composition material of the lid member 96, for example, there is a non-woven fabric made of a synthetic resin, a porous membrane made of a synthetic resin, or the like.

The storage packaging 90 configured as above, as illustrated in FIG. 7, stores the injector 10 such that the distal end (the distal end of the cap 46) of the injector 10 is not in contact with the bottom wall 92a of the packaging body 92. Accordingly, the staying of water vapor in the internal space 93 of the storage packaging 90 and the like are suppressed.

The injector 10 according to this embodiment is basically configured as above, and, next, the operations and the advantages thereof will be described.

The injector 10 configured as a prefilled syringe injector, as described above, can be transported and stored in the state of being stored in the storage packaging 90 until a medicine is filled therein. However, because the storage packaging 90 is configured to hang the injector 10 such that the distal end of the injector 10 is not in contact therewith, the size thereof tends to increase. For this reason, according to the injector 10 of the first embodiment, while the protection device 20 is included, the inner cylinder 42 is set to be as short as possible such that the whole length is about the same length as that of an injector in which the protection device 20 is not installed.

Here, a primary factor that increases the axial length of the protection device 20 is based on that the guide passage 54 according to the amount of exposure of the needle 12 that needs to be included. In other words, the protection device 20 includes the guide passage 54 that guides the projection 76 in one of the outer cylinder 40 and the inner cylinder 42. Thus, for example, a configuration may be considered in which the guide passage 54 is arranged in the inner cylinder 42, and the projection 76 is arranged in the outer cylinder 40. However, in a case where the guide passage 54 is arranged in the inner cylinder 42, the axial length of the inner cylinder 42 needs to be lengthened that much. For example, in a case where the inner cylinder 42 is lengthened toward the distal end side, the needle 12 needs to be formed to be lengthened according thereto, and, consequently, the whole length of the injector 10 becomes long. In addition, for example, in a case where the inner cylinder 42 is lengthened toward the proximal end side, the inner cylinder 42 needs to be configured to cover the distal end portion of the trunk portion 22. For this reason, the outer diameter of the inner cylinder 42 becomes larger than the outer diameter of the trunk portion 22, and the outer diameter of the outer cylinder 40, in other words, the outer diameter of the protection device 20, becomes larger in accordance therewith, and the size of the injector 10 is increased. Furthermore, in this case, the outer diameter of the protection device 20 exceeds a maximum outer diameter of the hanging portion 26, and there is concern that the injector 10 cannot be inserted into the hole portion 94c of the holding member 94 of the storage packaging 90.

In the protection device 20 according to the first embodiment, the guide passage 54 is arranged in the outer cylinder 40 that originally requires the length for covering the needle 12. In this way, the inner cylinder 42 can be set to have the axial length smaller than the axial length of the guide passage 54 and have the outer diameter be smaller than the outer diameter of the trunk portion 22. Accordingly, the protection device 20 allows the outer cylinder 40 and the inner cylinder 42 to have lengths and outer diameters that are required minimums; in order words, the size of the protection device 20 can be decreased. In this way, even in a case where the injector 10 includes the protection device 20, the whole length of the injector 10 can be set to have a length of the same level as that of the injector to which the protection device 20 is not installed, and the outer diameter of the protection device 20 is smaller than the maximum outer diameter of the hanging portion 26. Accordingly, the injector 10 can be used with conventional storage packaging as well.

Particularly, the axial length of the inner cylinder 42 may be set to be shorter than the axial length of the needle holding portion 24. The needle holding portion 24 requires a predetermined length so as to hold the needle 12, and the inner cylinder 42 surrounds only the periphery of the needle holding portion 24, whereby a decrease in the size is further promoted. In addition, the reason for the setting of the axial length of the inner cylinder 42 according to the first embodiment to be slightly shorter than the axial length of the needle holding portion 24 is to realize stable rotation of the inner cylinder 42 and stable engagement of the inner cylinder 42 with the outer cylinder 40. The axial length of the inner cylinder 42 may be short and, for example, may be formed in the shape of a ring surrounding the periphery of the constriction portion 38.

The injector 10 for a prefilled syringe that is housed in the storage packaging 90 is provided for a user as a prefilled syringe in which a medicine is filled, and the storage space 16 of the main body unit 14 is sealed by the gasket 18a. In a case where the prefilled syringe is provided in a state in which the plunger 18 is not installed, the user attaches the plunger 18 (see FIG. 1) to the gasket 18a when a patient is injected. Thereafter, the knob portion 82 of the cap 46 is gripped, and the cap 46 is detached from the outer cylinder 40 so as to be in the puncturing-enabled state (see FIG. 8A). Until the cap 46 is detached, the backward movement (the movement toward the proximal end side) of the outer cylinder 40 with respect to the main body unit 14 is restricted by this cap 46. Accordingly, before the cap 46 is detached (for example, when the plunger 18 is attached or the like), the injector 10 reliably prevents the exposure of the needle 12 and blocks the movement of the projection 76 from the before-puncturing section 56a of the guide passage 54. In addition, because the projection 76 is arranged at the before-puncturing section 56a, the edge portion of the guide passage 54 is caught in the projection 76, and accordingly, the outer cylinder 40 is prevented from moving forward with respect to the main body unit 14 and detaching from the main body unit 14. In addition, because the cap 46 is attached until prior to the puncturing process, the sterilization of the needle 12 can be maintained.

After the cap 46 is detached, the user brings the distal end portion of the outer cylinder 40 into contact with a patient's puncturing portion (the arm or the like) so as to be fixed in a simplified manner and moves the main body unit 14 forward with respect to the outer cylinder 40. Relatively, the outer cylinder 40 moves backward with respect to the main body unit 14. In accordance with the forward movement of the main body unit 14, the needle 12 held by the needle holding portion 24, as illustrated in FIG. 8B, is exposed to the distal end side through the opening portion 70 of the outer cylinder 40. At this time, the spring 44 is elastically transformed so as to be contracted in the axial direction.

The projection 76 of the inner cylinder 42 moves to the distal end side along the first passage 56 from the before-puncturing section 56a in accordance with the forward movement of the main body unit 14. For this reason, the inner cylinder 42 that is attached to the needle holding portion 24 to be freely rotatable rotates in the peripheral direction in accordance with the inclination of the first passage 56. Because the inner cylinder 42 is attached to the needle holding portion 24 with a contact area being decreased by the bearing rib 30, the inner cylinder 42 can be smoothly rotated with respect to the bearing rib 30.

In addition, as illustrated in FIG. 9A, in an initial step (a section at which the projection 76 moves only to the distal end side along the first passage 56) in which the projection 76 is moved from the before-puncturing section 56a, the flange notching portion 80 of the inner cylinder 42 opposes the locking convex portion 68 of the outer cylinder 40. Accordingly, the inner cylinder 42 can be easily moved forward without being caught in the locking convex portion 68. Then, when the flange portion 74 exceeds the locking convex portion 68, the inner cylinder 42 is rotated along the inclination of the first passage 56. In a step in which the projection 76 is moved to the axial-direction middle section 54a of the guide passage 54, the flange portion 74 is arranged at a position overlapping the peripheral direction of the locking convex portion 68.

Thereafter, when the projection 76 is moved forward into the second passage 58 through the axial-direction middle section 54a of the guide passage 54, and the main body unit 14 is further moved forward, as illustrated in FIG. 8C, the projection 76 is moved to the puncturing section 58a, which is disposed on the distal end side, along the second passage 58. In the step in which the projection 76 is moved to the puncturing section 58a, most of the needle 12 is exposed from the distal end of the outer cylinder 40, and a state is formed in which the interior of the patient's body is punctured. Here, because the needle holding portion 24 of the injector 10 is relatively short, it is easy to allow the amount of the forward movement of the main body unit 14 and the amount of exposure of the needle 12 to match a user's sense in the puncturing process. Accordingly, the user can perform the puncturing process by appropriately operating the needle 12.

In the step in which the projection 76 is moved from the before-puncturing section 56a to the puncturing section 58a, as illustrated in FIGS. 9A and 9B, on the inner side of the outer cylinder 40, the locking convex portion 68 passes the proximal end from the distal end of the inner cylinder 42. At this time, because the locking convex portion 68 passes through the passage allowing portion 81, the backward movement of the outer cylinder 40 and the rotation of the inner cylinder 42 are smoothly performed.

In the punctured state of the needle 12, the user forwardly moves the plunger 18 inserted on the proximal end side of the main body unit 14, thereby discharging the medicine filled in the storage space 16 of the main body unit 14 from the needle tip. Accordingly, the administration of the medicine for the patient is performed.

After the administration of the medicine, the main body unit 14 is moved backward so as to be separated from the patient. At this time, the outer cylinder 40 receives a pressing force in accordance with elastic returning of the contracted spring 44 and moves forward with respect to the main body unit 14. The projection 76 that is located at the puncturing section 58a is linearly moved in the second passage 58 toward the proximal end side in accordance with the forward movement of the outer cylinder 40 and is guided into the third passage 60. In order for the projection to enter the third passage 60, the inclined portion 76a of the projection 76 may be guided by the apex 54b, and the projection 76 is reliably moved into the third passage 60.

The forward movement of the outer cylinder 40 is continued until the projection 76 is moved to the after-puncturing section 60a disposed on the proximal end side of the third passage 60 in accordance with the elastic returning of the spring 44. In the step in which the projection 76 is moved to the after-puncturing section 60a, the projection 76 is brought into contact with the edge portion disposed on the proximal end side of the third passage 60, whereby the forward movement of the outer cylinder 40 is stopped.

In addition, as illustrated in FIG. 9C, in the process in which the projection 76 is moved to the after-puncturing section 60a, the flange portion 74 is brought into contact with the inclined surface 68b of the locking convex portion 68 and elastically transforms the proximal end side of the hook portion 64 to the outer side in the diameter direction. Accordingly, the flange portion 74 passes to advance over the locking convex portion 68 and is moved to the further proximal end side than the locking convex portion 68. After passing through the flange portion 74, as the hook portion 64 is elastically returned, the locking surface 68a of the locking convex portion 68 is caught in the distal end surface of the inner cylinder 42 (the flange portion 74). In other words, in the state in which the projection 76 is moved to the after-puncturing section 60a, the flange portion 74 of the inner cylinder 42 is engaged with the hook portion 64 of the outer cylinder 40, whereby the backward movement of the outer cylinder 40 with respect to the inner cylinder 42 can be restricted. Accordingly, in the injector 10, the exposure of the needle 12 according to the backward movement of the outer cylinder 40 is prevented, and accordingly, the user can handle the injector 10 in a safe manner in a disposal process or the like.

As above, when the outer cylinder 40 is moved backward in the puncturing process performed by the needle 12 according to the projection 76 arranged in the inner cylinder 42 and the guide passage 54 arranged in the outer cylinder 40, the injector 10 can rotate the inner cylinder 42 by operating the projection 76 arranged in the guide passage 54. For this reason, an arrangement relation for engaging the hook portion 64 of the outer cylinder 40 and the inner cylinder 42 with each other can be built in an easy manner, and the backward movement of the outer cylinder 40 can be restricted in a state in which the needle 12 is housed inside the outer cylinder 40 after the puncturing process. Accordingly, after the puncturing process, the injector 10 can prevent the exposure of the needle 12 from the outer cylinder 40, whereby the safety level is improved.

In this case, in the injector 10, the hook portion 64 of the outer cylinder 40 is caught in the inner cylinder 42 at the after-puncturing section 60a, and accordingly, the backward movement of the outer cylinder 40 can be restricted by the inner cylinder 42 in a simple manner. In addition, because the inner cylinder 42 includes the flange portion 74 and the passage allowing portion 81, in the injector 10, the passage of the locking convex portion 68 of the outer cylinder 40 through the passage allowing portion 81 is allowed in the puncturing process performed by the needle 12, and accordingly, the movement of the outer cylinder 40 can be performed in an easy manner. Then, after the puncturing process, the flange portion 74 is caught in the locking convex portion 68, whereby the backward movement of the outer cylinder 40 can be restricted more reliably.

In addition, because the inner cylinder 42 can be formed in a shape (small size) in which the axial length is shorter than the axial length of the guide passage 54, the size of the whole injector 10 can be decreased. Accordingly, the storage and the transportation of the injector 10 can be performed in an easy manner, and the operability of the needle 12 is improved according to the distal end portion of the injector 10 configured to be short, and the puncturing process can be efficiently performed by the needle 12 with high accuracy. Furthermore, by configuring the axial length of the inner cylinder 42 at a level matching the needle holding portion 24, particularly a change in the shape of the main body unit 14 of the injector 10 is not required. Accordingly, the protection device 20 has versatility enabling it to be easily attached also to a conventional injector.

The injector 10 according to the present invention is not limited to the above-described embodiment but may take various forms. For example, the guide passage 54 arranged in the outer cylinder 40 may be not only formed to communicate with the outside but also formed in a groove shape on the inner surface of the side wall 50. In this way, although the guide passage 54 is included, the side wall 50 exhibits an external appearance of one surface, and accordingly, the influence (interrupt or the like) of the user, external environments, and the like on the projection 76 can be prevented.

Second Embodiment

Next, an injector 10A according to a second embodiment will be described with reference to FIGS. 10 to 13C. In the description presented below, the same reference numeral is assigned to the same configuration as that of the injector 10 according to the first embodiment or a configuration having the same function as that of the injector 10, and detailed description thereof will not be presented.

Figure 10:
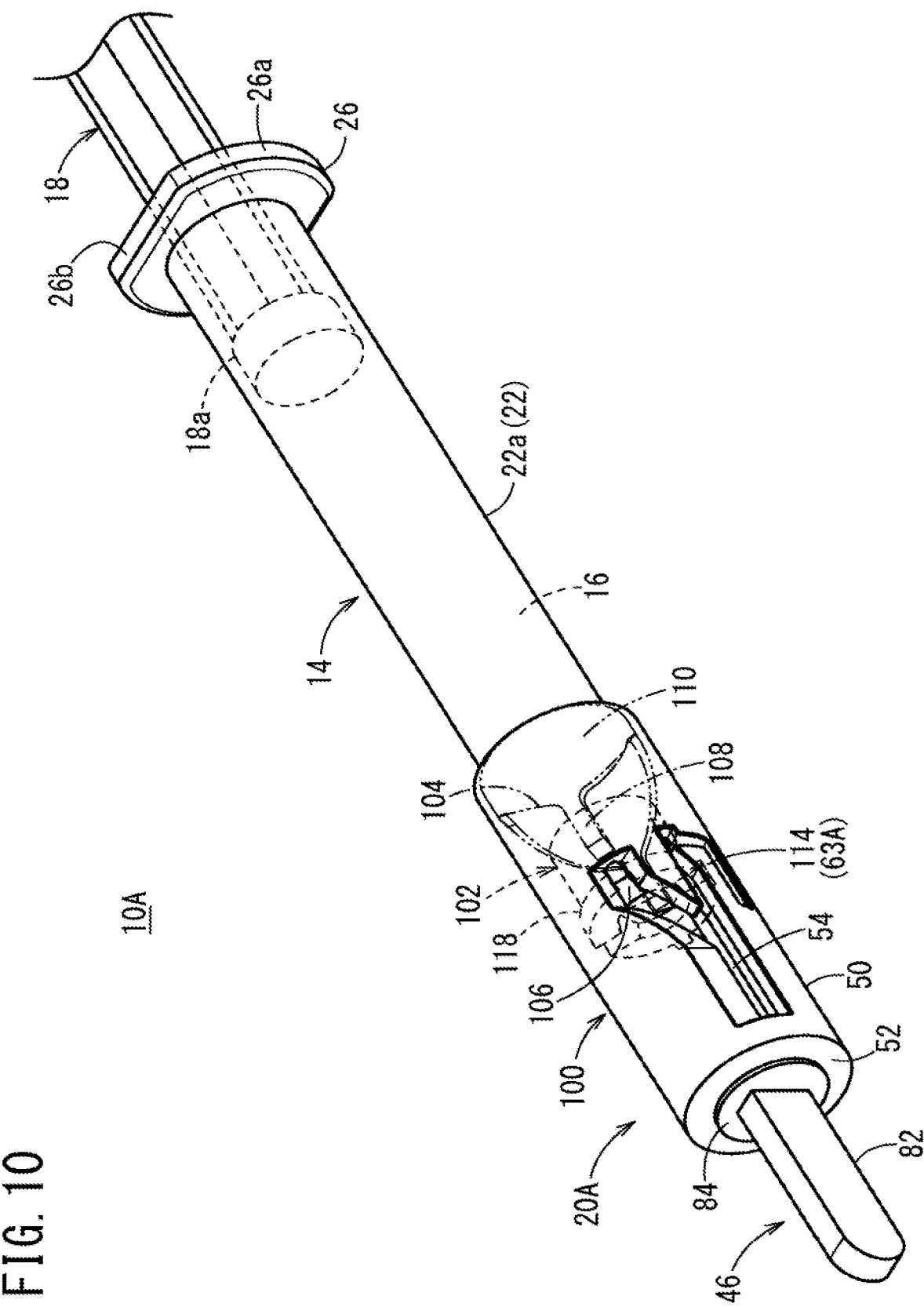
FIG. 10 is a perspective view that illustrates the whole configuration of an injector according to a second embodiment.
Figure 11A:
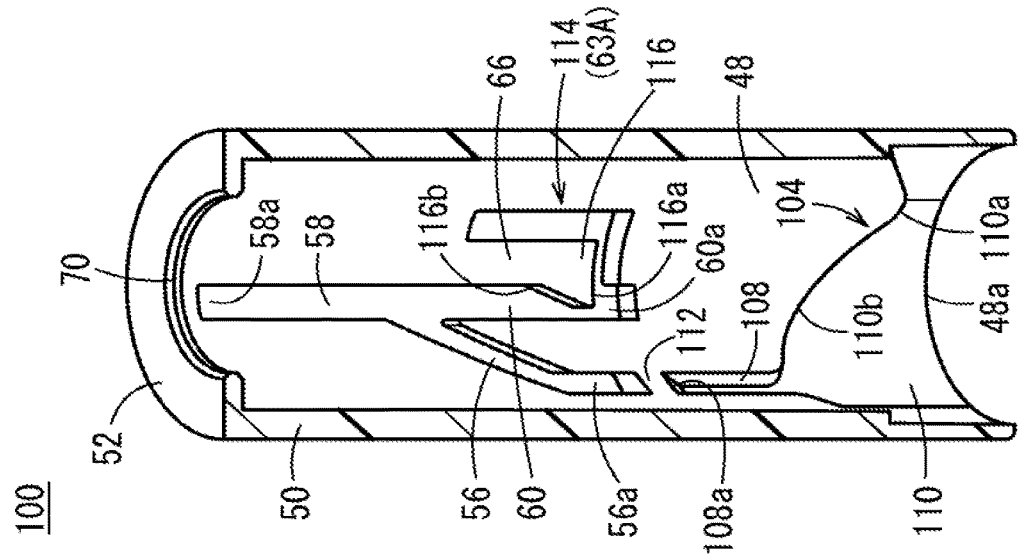
FIG. 11A is a perspective view that illustrates an outer cylinder illustrated in FIG. 10.
Figure 11B:
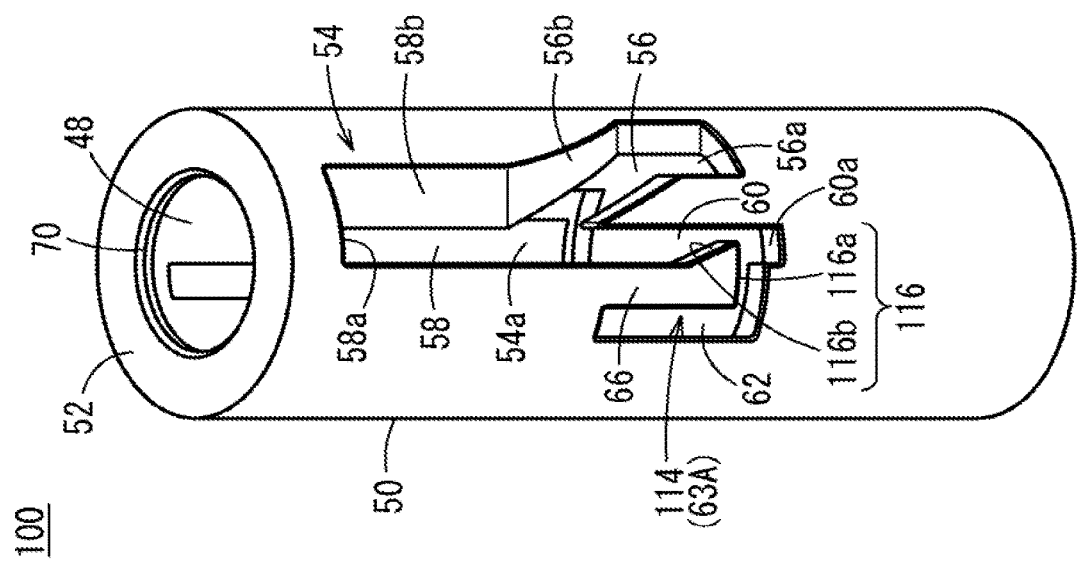
FIG. 11B is a cross-sectional perspective view of the outer cylinder illustrated in FIG. 11A.

In the injector 10A according to the second embodiment, a protection device 20A (an outer cylinder 100 and an inner cylinder 102) is different from the protection device 20 of the injector 10 according to the first embodiment. More specifically, as illustrated in FIGS. 10, 11A, and 11B, the outer cylinder 100 includes a leading groove portion 104 on the inner surface of a side wall 50 that configures a hollow part 48. Meanwhile, the amount of protrusion of a projection 106 of an inner cylinder 102 (see FIG. 10) is set to approximately match the bottom surface of the leading groove portion 104 and protrudes from a flange portion 118 to the side.

The leading groove portion 104 is a passage used for leading the projection 106 of the inner cylinder 102 from the proximal end side of the outer cylinder 100 to a guide passage 54 at the time of assembling the outer cylinder 100 and the inner cylinder 102. This leading groove portion 104 includes: one pair of merged passages 108 (first groove) formed on the proximal end side of a before-puncturing section 56a of the guide passage 54; and an entrance passage 110 (second groove), which is wide in a peripheral direction, connected to the proximal end side of the merged passages 108.

The merged passages 108 are passages used for finally leading the projection 106 of the inner cylinder 102 to the guide passage 54, and the width thereof is set to approximately match the width of the first passage 56 of the guide passage 54. Each merged passage 108 is formed in a linear shape parallel to the insertion direction of the inner cylinder 102. Between the merged passage 108 and the guide passage 54, an inner surface of the side wall 50 is present, and this portion serves as a partition wall 112 that separates the merged passage 108 and the guide passage 54 from each other. The distal end side of the merged passage 108 is formed as a tapered surface 108a inclining toward the partition wall 112, and the projection 106 moved from the proximal end side can be moved to the inside of the guide passage 54 in an easy manner.

The entrance passage 110 includes an undulating groove side 110b that has an entrance of the one pair of merged passages 108 as its distal end apex, in the exploded view of the inner side of the outer cylinder 100, and has portions of which the phases deviate by 9° from that of the distal end apex in the peripheral direction as one pair of proximal end apexes 110a. The groove side 110b of the entrance passage 110 is smoothly inclined from the proximal end apex 110a toward the merged passage 108 in the peripheral direction (rotation direction) of the inner cylinder 102 and toward the distal end side. In addition, the proximal end side of the entrance passage 110 is formed to be continuous from the proximal end opening 48a of the outer cylinder 100.

Hereinafter, the assembling of the outer cylinder 100 and the inner cylinder 102 will be described with reference to FIGS. 12A to 12C. In the assembly of the protection device 20A, the inner cylinder 102 attached to the needle holding portion 24 to be freely rotatable is inserted into the outer cylinder 100 starting from the proximal end opening 48a. At this time the position of the projection 106 of the inner cylinder 102 in the peripheral direction may deviate from the leading groove portion 104 of the outer cylinder 100. For example, as illustrated in FIG. 12A, in a case where the projection 106 opposes the proximal end apex 110a, the projection 106 is brought into contact with the proximal end apex 110a according to the insertion, and the projection 106 is displaced to one of one pair of the groove sides 110b that are continuous from the proximal end apex 110a. In other words, as the inner cylinder 102 is rotated by being guided by the groove side 110b, the projection 106 is moved on the entrance passage 110 along the groove side 110b.

Then, the projection 106 is led to the merged passage 108 that is continuous from the distal end apex of the groove side 110b, is further moved straight inside the merged passage 108, and, as illustrated in FIG. 12B, arrives at the distal end portion of the merged passage 108. Thereafter, the projection 106 gets out from the merged passage 108 by the tapered surface 108a of the merged passage 108 and advances over the partition wall 112. In this way, the projection 106, as illustrated in FIG. 12C, is arranged at the before-puncturing section 56a of the guide passage 54 in an easy manner.

As above, according to the injector 10A, because the outer cylinder 100 includes the leading groove portion 104, the projection 106 of the inner cylinder 102 can be smoothly led to the guide passage 54 in the assembly of the protection device 20A, and accordingly, the assembly operation can be efficiently performed. In addition, in the assembly process, damages and the like in the outer cylinder 100 and the inner cylinder 102 can be suppressed.

In addition, in the assembly of the injector 10A, the inner cylinder 102 attached to the needle holding portion 24 is inserted in the state in which the cap 46 is attached to the outer cylinder 100 in advance. In the injector 10A, by forming the merged passage 108 of the leading groove portion 104 in a linear shape parallel to the insertion direction of the inner cylinder 102, after the projection 106 is inserted into the merged passage 108, the needle tip of the needle 12 is configured to be stuck into the sealing portion 86c (see FIG. 3A) of the cap 46. Accordingly, in the assembly process, the needle tip of the needle 12 can be stuck straight into the sealing portion 86c. In addition, because the rotation of the inner cylinder 102 with respect to the outer cylinder 100 is restricted by the merged passage 108 before the projection 106 advances over the partition wall 112, it is difficult for the inner cylinder 102 to rotate when the projection 106 advances over the partition wall 112, and the projection 106 can be reliably lead to the guide passage 54.

Referring back to FIGS. 11A and 11B, in the injector 10A, a hook portion 114 (restriction portion 63A) formed in the outer cylinder 100 is different from the hook portion 64 of the injector 10 according to the first embodiment. This hook portion 114 includes an elastic piece 66 that does not have the locking convex portion 68 arranged on the inside thereof and a claw portion 116 that is formed in a regular triangle shape on the proximal end side of the elastic piece 66, protrudes in the peripheral direction (the guide passage 54 side), and is directly caught in the projection 106. In addition, the claw portion 116 includes a locking side 116a, which is arranged on the proximal end side, that protrudes to the inside of the guide passage 54 near the distal end of the after-puncturing section 60a and is parallel to the peripheral direction of the outer cylinder 100 and an inclined side 116b, which is arranged on the distal end side, inclined with respect to the axial direction of the outer cylinder 100. As the projection 106 is engaged with the locking side 116a, the inner cylinder 102 restricts the backward movement of the outer cylinder 100.

Meanwhile, as illustrated in FIGS. 12A and 12B, the inner cylinder 102 is configured not to include the passage allowing portion 81 that is arranged in the flange portion 74 so as to pass the locking convex portion 68 according to the first embodiment. In other words, in the inner cylinder 102, the base portion notched portion 78 is arranged so as to be installed to the needle holding portion 24 by opening the upper portion of the cylinder portion 71. For this reason, the flange portion 118 does not include the flange notching portion 80 (see FIG. 5A) but is formed to protrude along the peripheral direction of the distal end side of the base portion 72. In addition, as long as the inner cylinder 102 includes the projection 106, the shape thereof is not particularly limited but, for example, may be a cylindrical shape having no flange portion 118 or a ring shape.

Hereinafter, the operation of the injector 10A according to the second embodiment after the puncturing process is performed for a patient using the needle 12 will be described with reference to FIGS. 13A to 13C. In a step in which the needle 12 is exposed in the puncturing process, as illustrated in FIG. 13A, the projection 106 is arranged at the puncturing section 58a of the guide passage 54. In this state, when the main body unit 14 is separated so as to draw out the needle 12 from the patient, the outer cylinder 100 is moved forward relative to the main body unit 14 based on the elastic return of the spring 44. The projection 106 located at the puncturing section 58a is linearly moved in the second passage 58 to the proximal end side according to the forward movement of the outer cylinder 100 and, as illustrated in FIG. 13B, is moved up to the after-puncturing section 60a disposed on the proximal end side of the third passage 60.

In the process in which the projection 106 is moved to the after-puncturing section 60a, the projection 106 is brought into contact with the inclined side 116b of the hook portion 114 (the claw portion 116), and, by elastically transforming the hook portion 114, the projection 106 advances over the claw portion 116. As a result, the projection 106 is moved to the further proximal end side than the claw portion 116, and the locking side 116a of the claw portion 116 is caught in the projection 106. In other words, in the state in which the projection 106 is moved to the after-puncturing section 60a, the projection 106 of the inner cylinder 102 is engaged with the claw portion 116 of the outer cylinder 100, whereby the backward movement of the outer cylinder 100 with respect to the inner cylinder 102 can be restricted.

As above, as the hook portion 114 (the claw portion 116) is directly caught in the projection 106, according to the injector 10A, advantages similar to those of the injector 10 according to the first embodiment can be acquired. In addition, because the passage allowing portion 81 is not arranged in the inner cylinder 102 in the injector 10A, the protection device 20A can employ a simpler configuration.

Third Embodiment

Figure 14A:
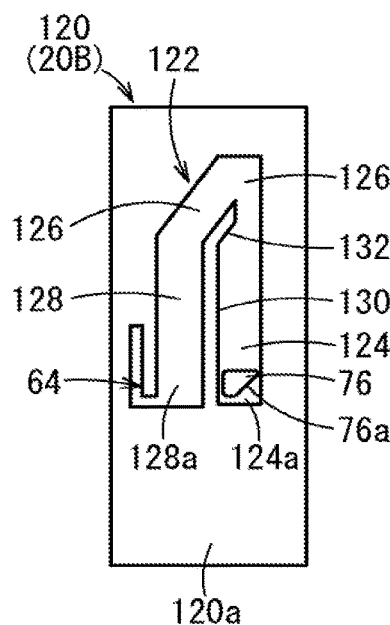
FIG. 14A is a first schematic diagram that illustrates an outer cylinder of an injector according to a third embodiment.

In an injector 10B according to a third embodiment, as illustrated in FIG. 14A, the configuration of a guide passage 122 arranged in the outer cylinder 120 (the protection device 20B) is different from those of the injectors 10 and 10A according to the first and second embodiments. The configuration other than the outer cylinder 120 is basically the same as that of the injector 10, and FIGS. 1 and 2 may be referred to.

The guide passage 122 of the outer cylinder 120 is formed as a long hole in which a first passage 124, a second passage 126, and a third passage 128 are sequentially lined up as the movement passage of the projection 76 of the inner cylinder 42 when the outer cylinder 120 is moved forward/backward.

The first passage 124 has a before-puncturing section 124a at which the projection 76 is arranged before the puncturing process performed by the needle 12 (see FIG. 2) on the proximal end portion side and extends in a linear shape toward the distal end side of the outer cylinder 120. The second passage 126 is configured to be continuous from the distal end portion of the first passage 124 and obliquely extends in the peripheral direction of the outer cylinder 120 toward the proximal end side. In this case, a connection portion between the first passage 124 and the second passage 126 becomes the puncturing section 126a. The third passage 128 is configured to be continuous from the proximal end portion of the second passage 126 and extends in a linear shape at a position deviating from the first passage 124 in the peripheral direction toward the proximal end side of the outer cylinder 120. The proximal end portion of the third passage 128 becomes an after-puncturing section 128a at which the projection 76 is arranged after the puncturing process of needle 12.

Between the first passage 124 and the third passage 128, a division wall 130 is formed by a side wall 120a that configures the outer cylinder 120. This division wall 130 includes a bending piece 132 that extends toward the distal end side of the outer cylinder 120, bends at the connection portion of the third passage 128 and the second passage 126 along the inclination of the second passage 126, and protrudes by a predetermined amount. The first passage 124 and the second passage 126 are partly partitioned by the bending piece 132. The bending piece 132 allows movement from the first passage 124 to the second passage 126 and restricts returning from the second passage 126 to the first passage 124, thereby having a function of guiding the movement along the second passage 126.

The injector 10B according to the third embodiment is basically configured as above, and, hereinafter, the operations of the outer cylinder 120 and the inner cylinder 42 (the projection 76) in the puncturing process performed by the needle 12 will be described. Before the puncturing process performed by the needle 12, a state is formed in which the outer cylinder 120 covers the needle 12 and the inner cylinder 42, and the projection 76, as illustrated in FIG. 14A, is arranged at the before-puncturing section 124a of the first passage 124.

Figure 14B:
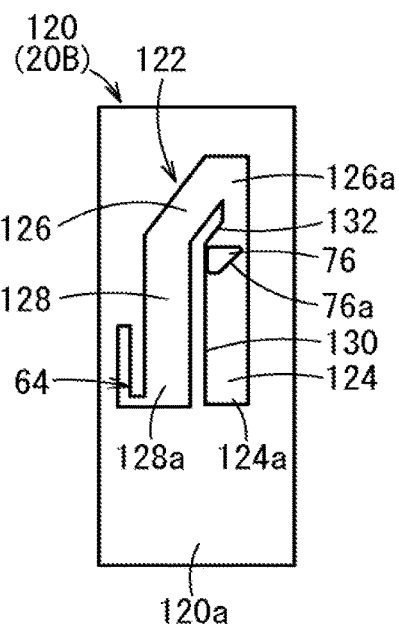
FIG. 14B is a second schematic diagram that illustrates the operation of a projection according to the outer cylinder illustrated in FIG. 14A.
Figure 14C:
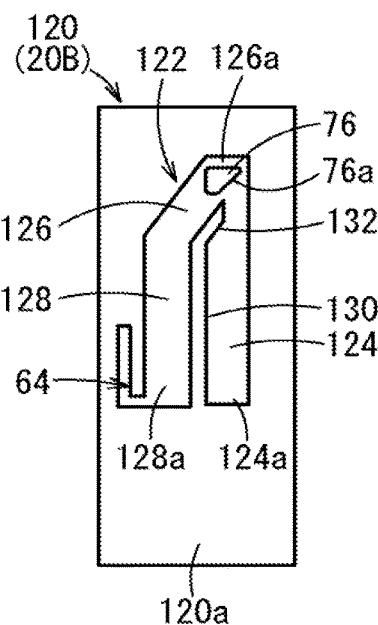
FIG. 14C is a third schematic diagram that illustrates the operation of the projection following FIG. 14B.

In the puncturing process performed by the needle 12, the main body unit 14 is moved forward, the outer cylinder 120 is moved backward relative to the inner cylinder 42, and accordingly, the projection 76 is moved straight inside the first passage 124 and, as illustrated in FIG. 14B, is brought into contact with the bending piece 132. In addition, when the main body unit 14 is moved forward, the projection 76 advances over the bending piece 132 by elastically transforming the bending piece 132 and, as illustrated in FIG. 14C, arrives at the puncturing section 126a. Because a sound or resistance is transmitted to the user according to the advancing-over of the projection 76, the user can recognize the puncturing process performed by the needle 12 and can start administering a medicine well.

Figure 14D:
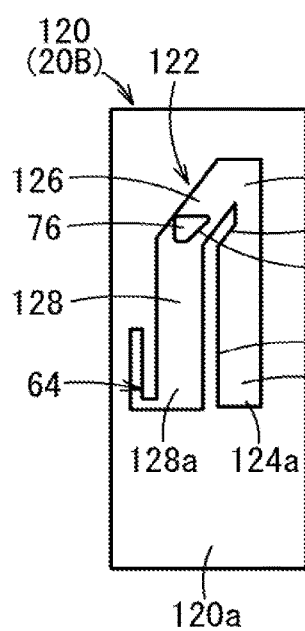
FIG. 14D is a fourth schematic diagram that illustrates the operation of the projection following FIG. 14C.
Figure 14E:
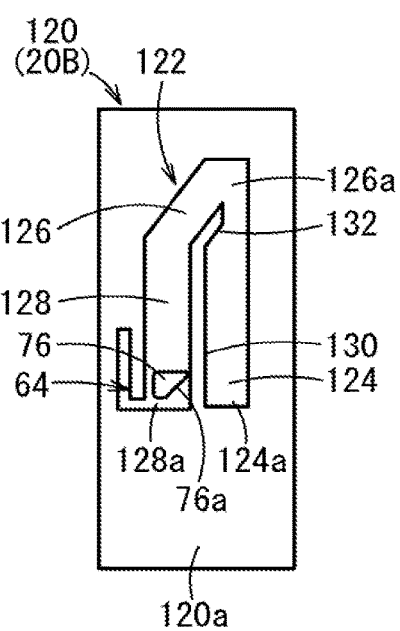
FIG. 14E is a fifth schematic diagram that illustrates the operation of the projection following FIG. 14D.

When the main body unit 14 is moved backward after the administration of the medicine, the outer cylinder 120 is moved forward relative to the inner cylinder 42 depending on the spring 44. At this time, the projection 76 is brought into contact with the bending piece 132 and, as illustrated in FIG. 14D, is moved along the second passage 126. Particularly, the inclined portion 76a arranged in the projection 76 is actively guided by the bending piece 132 and is prevented from being returned to the first passage 124. In addition, when the outer cylinder 120 is moved forward, the projection 76 is moved from the second passage 126 to the third passage 128 and is moved straight along the third passage 128. Then, as illustrated in FIG. 14E, when the projection 76 is moved to the after-puncturing section 128a, the inner cylinder 42 is caught in the locking convex portion 68 (see FIG. 9C) formed in the hook portion 64 (the restriction portion 63) that is the same as that of the first embodiment, and the outer cylinder 120 and the inner cylinder 42 are engaged with each other. In this way, the backward movement of the outer cylinder 120 with respect to the inner cylinder 42 is restricted, and the needle 12 can be prevented from being exposed.

In other words, according to the injector 10B of the third embodiment, advantages similar to those of the injector 10 according to the first embodiment can be acquired. In conclusion, in each of the injectors 10, 10A, and 10B, the shape of the guide passage 54 or 122 is not particularly limited, but various configurations may be applied which can realize the engagement between the outer cylinder and the inner cylinder by rotating the inner cylinder 42 or 102 according to the forward/backward movement of the outer cylinder 40, 100, or 120.

Fourth Embodiment

Figure 16:
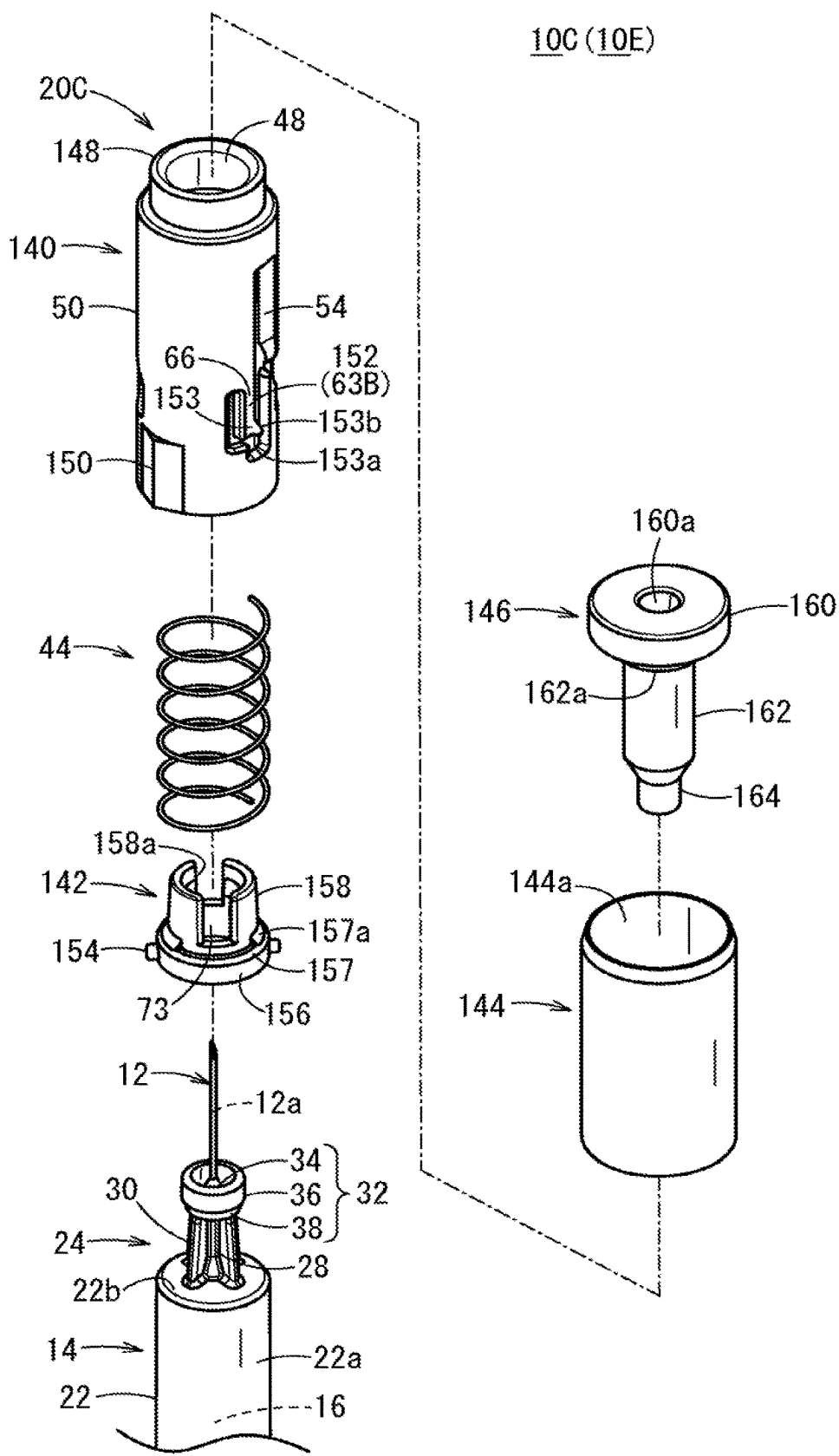
FIG. 16 is an exploded perspective view that illustrates a protection device of the injector illustrated in FIG. 15 in an exploded manner.

Next, an injector 10C according to a fourth embodiment will be described with reference to FIGS. 15 to 18. The injector 10C (a protection device 20C), as illustrated in FIG. 15, includes a cover 144 that covers the outer peripheral surface of the outer cylinder 140, which is different from the injectors 10, 10A, and 10B according to the first to third embodiments. In addition, as illustrated in FIG. 16, in the protection device 20C, in addition to the cover 144, the configurations of the outer cylinder 140, the inner cylinder 142, and a cap 146 are different from those of the protection devices 20, 20A, and 20B to some extent.

More specifically, the outer cylinder 140 includes: a side wall 50 that surrounds the periphery of the hollow part 48; and a protruded wall 148 of a cylindrical shape that is configured to be continuous from the distal end portion of the side wall 50 and is formed to have a diameter smaller than the side wall 50. On the side wall 50, one pair of guide passages 54 is arranged, and one pair of stopper portions 150 is molded integrally with the proximal end side.

Figure 17A:
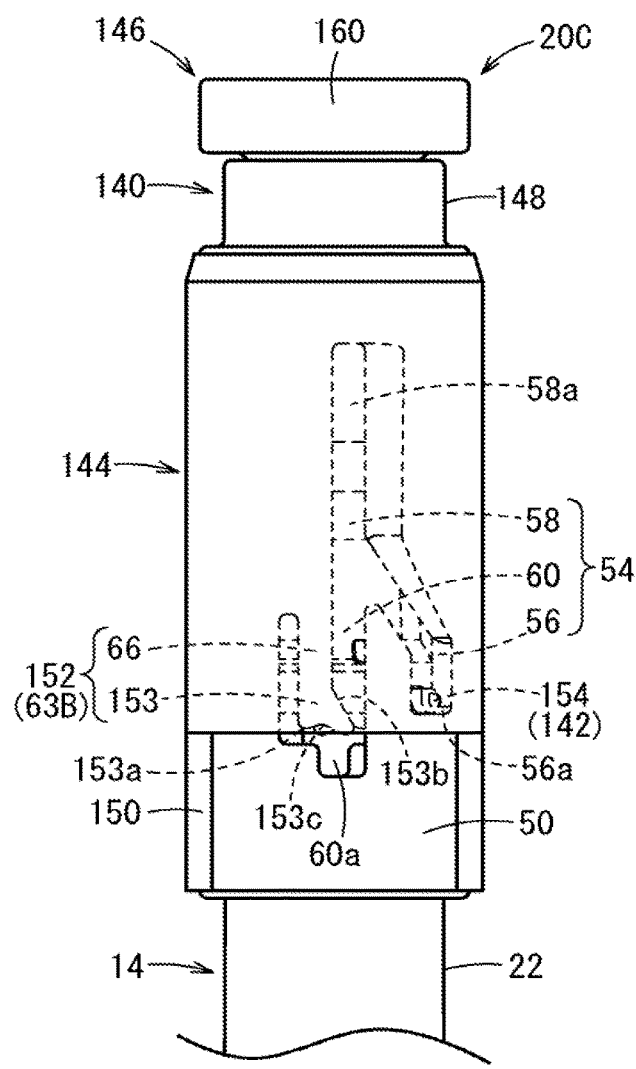
FIG. 17A is a side view that illustrates a distal end portion of the injector illustrated in FIG. 15.

The guide passage 54 is formed to be basically the same as that of the second embodiment. However, the shape of a hook portion 152 (a restriction portion 63B) arranged in the guide passage 54 is different from that of the second embodiment to some extent. More specifically, the hook portion 152 includes an elastic piece 66 and a claw portion 153 that is arranged on the proximal end side of the elastic piece 66. The claw portion 153 protrudes in the peripheral direction (the guide passage 54 side) more than the claw portion 116 according to the second embodiment. A locking side 153a of the claw portion 153, as illustrated in FIG. 17A, includes a V-shaped groove 153c opening toward the after-puncturing section 60a in which the center portion is slightly depressed toward the distal end side with respect to both edge portions. In a case where the outer cylinder 140 is moved forward, and the inner cylinder 142 is moved to the after-puncturing section 60a, the locking side 153a can guide the projection 154 of the inner cylinder 142 to the V-shaped groove 153c even when the outer cylinder 140 operates to be moved backward again. An inclined side 153b is formed similarly to the inclined side 116b.

In addition, the after-puncturing section 60a arranged in the guide passage 54 (the third passage 60) is formed to have a slightly large width (for example, larger than the width of the second passage 58 to some extent) along the peripheral direction. Furthermore, the after-puncturing section 60a is located on the further proximal end side than the before-puncturing section 56a.

The stopper portions 150 are formed at positions with phases deviating by about 90° in the peripheral direction with respect to the corresponding guide passage 54 on the proximal end side of the one pair of the guide passages 54. The stopper portion 150 protrudes by a height approximately matching the thickness of the cover 144 from the peripheral surface of the side wall 50, thereby determining the installation position of the cover 144. The stopper portion 150, from the proximal end of the outer cylinder 140 toward the distal end side, passes the proximal end portion (the after-puncturing section 60a) of the guide passage 54 and extends up to the proximal end section of the claw portion 153.

Figure 17B:
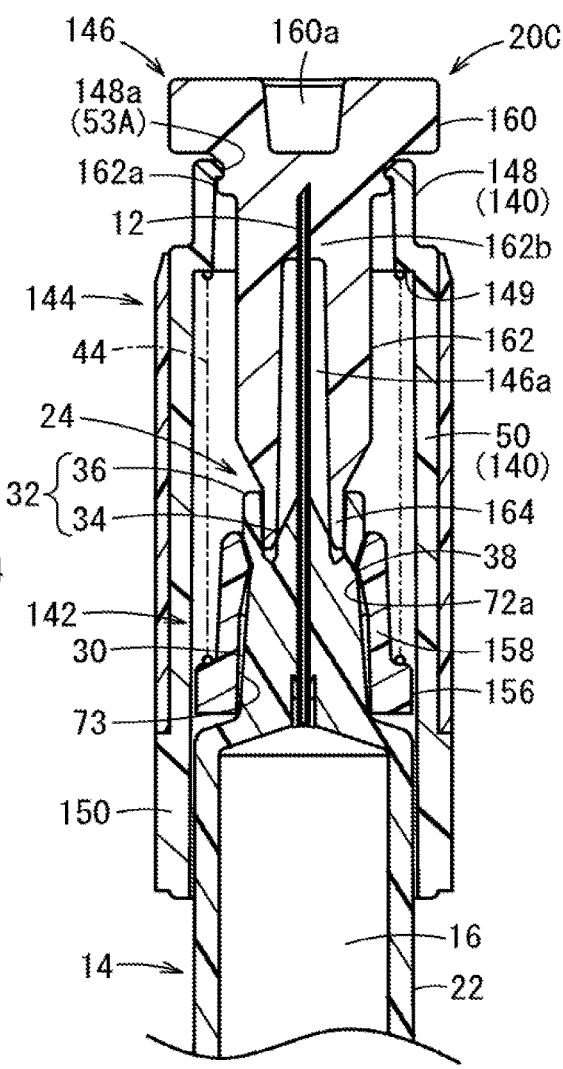
FIG. 17B is a side cross-sectional view that illustrates the distal end portion of the injector illustrated in FIG. 15.

Meanwhile, the protruded wall 148 has an outer diameter smaller than that side wall 50 and, as illustrated in FIG. 17B, narrows the hollow part 48 arranged on the inner side. Thus, a level difference 149 is formed between the inner peripheral surface of the side wall 50 and the inner peripheral surface of the protruded wall 148, and this level difference 149 becomes a seat for receiving the distal end portion of the spring 44. In addition, on the inner peripheral surface of the upper end portion of the protruded wall 148, a locking claw 148a (a sealing member holding portion 53A) protruding to the inner side in the diameter direction is arranged. The locking claw 148a circles in a circular shape along the inner surface of the protruded wall 148.

It is preferable that the outer cylinder 140 is configured to be transparent or semi-transparent. In a case where the outer cylinder 140 is transparent, for example, even when an opaque cover 144 is installed, the proximal end portion of the inner cylinder 142 is seen through the outer cylinder 140 when the inner cylinder 142 is moved to the after-puncturing section 60a. Accordingly, the state of the inner cylinder 142 can be easily checked, and it can be easily checked whether the injector 10C is before use or not. In addition, the distal end portion of the needle 12 before the puncturing process can be easily recognized.

Referring back to FIG. 16, in the inner cylinder 142 housed inside the outer cylinder 140, one pair of projections 154 is arranged on the proximal end side. In addition, the inner cylinder 142 includes a proximal end circular portion 156 that has one pair of projections 154 on the outer peripheral surface thereof and distal end cylindrical portions 158 that are configured to be continuous from the distal end side of the proximal end circular portion 156. The proximal end circular portion 156 is formed to have an outer diameter that approximately matches the outer diameter of the trunk portion 22 of the main body unit 14 and has the same function as that of the flange portion 74 described above.

The distal end cylindrical portions 158 are formed to have a diameter smaller than the proximal end circular portion 156 and protrude by a dimension shorter than the axial length of the needle holding portion 24 from the proximal end circular portion 156 toward the distal end side. In the distal end cylindrical portion 158, one pair of cylindrical portion notching portions 158a having a relatively large width is arranged from an approximately middle portion of the inner cylinder 142 over the distal end thereof. Accordingly, the distal end portion sides of the distal end cylindrical portions 158 divided by the one pair of cylindrical portion notching portions 158a can be elastically transformed to be separated from each other, and the elevated portion 72a arranged on the inner side can be easily attached to the constriction portion 38 of the needle holding portion 24.

In addition, the proximal end circular portion 156 includes a level difference 157 that protrudes to the further outer side than the distal end cylindrical portion 158 and receives the proximal end portion of the spring 44 on the distal end surface. In other words, the spring 44 is supported between the level difference 149 and the level difference 157. At predetermined positions (positions of which the phases in the peripheral direction match that of the projection 154) on the level difference 157, one pair of spring support portions 157a is arranged. The one pair of spring support portions 157a prevents a discrepancy between the axis of the spring 44 and the axis of the inner cylinder 142 and reduce a chance for the spring 44 to be in contact with the side wall 50 of the outer cylinder 140. Accordingly, the spring 44 is smoothly expanded or contracted, and generation of a foreign body due to a contact can be avoided. In addition, it can be prevented that the proximal end of the spring 44 is fitted between the outer cylinder 140 deviating from the level difference 157 and the inner cylinder 142.

The cover 144 of the protection device 20C exhibits a cylindrical shape thicker than the side wall 50 of the outer cylinder 140, and, on the inside thereof, an installation hole 144a, which is a through hole, is formed along the axial direction. In a state in which the outer cylinder 140 is installed, the cover 144 covers the claw portion 153, thereby regulating elastic deformation of the claw portion 153 to the outer side in the diameter direction.

The axial length of the cover 144 is set to be a dimension according to the axial length of the side wall 50, for example, over the upper end of the stopper portion 150 from the distal end of the side wall 50. In addition, the cover 144 according to this embodiment is configured to be opaque. Accordingly, when the projection 154 of the inner cylinder 142 is located at the before-puncturing section 56a, the cover 144 covers the entire inner cylinder 142. On the other hand, when the projection 154 is located at the after-puncturing section 60a, the cover 144 allows the proximal end circular portion 156 of the inner cylinder 142 to protrude to the further proximal end side than the cover 144. Here, the installation position and the axial length of the cover 144 are not particularly limited, and the cover 144 may be installed to a part of the outer cylinder 140 such that the deformation of the hook portion 152 toward the outer side can be suppressed. Contrary to this, the cover 144 may be configured to cover all the outer peripheral surface of the outer cylinder 140.

The cap 146 includes a knob portion 160, an extended cylinder portion 162, and a fitting portion 164 from the distal end side toward the proximal end side. The knob portion 160 is formed to have an outer diameter that approximately matches the outer diameter of the side wall 50 of the outer cylinder 140, in other words, a diameter larger than the outer diameter of the distal end cylindrical portion 158. In addition, the knob portion 160 is formed to have a sufficient thickness and includes a concave portion 160a that is depressed toward the proximal end side at the center portion. The concave portion 160a is formed as a clearance for a gate at the time of performing injection molding of the cap 146.

The extended cylinder portion 162 extends by a predetermined length from the proximal end surface of the knob portion 160 toward the proximal end side. In addition, the extended cylinder portion 162 is formed to have an outer diameter that is smaller than the inner diameter of the inner peripheral surface of the protruded wall 148 that configures the hollow part 48. On an outer peripheral surface of a portion of the extended cylinder portion 162 that is connected to the knob portion 160, a circular projection 162a that can be caught in the locking claw 148a of the outer cylinder 140 is formed. In addition, on the distal end side of the extended cylinder portion 162, a sealing portion 162b (body portion) punctured by the needle 12 is arranged.

The fitting portion 164 is formed to have a diameter smaller than the extended cylinder portion 162 and can enter between the center support portion 34 of the needle holding portion 24 and the outer surrounding portion 36. The extended cylinder portion 162 and the fitting portion 164 have a hollow portion 146a in the axial center portion and can lead the needle 12 to the sealing portion 162b through the hollow portion 146a. The cap 146 configured as above is short on the distal end side in the assembled state of the protection device 20C, and accordingly, the size of the injector 10C can be further decreased, and the transportation, the storage, and the like of the injector can be performed in an easier manner.

The injector 10C basically performs the same operation as that of the injector 10 at the time of use. In other words, the cap 146 is detached from the distal end portion of the outer cylinder 140 so as to allow the needle 12 to be in the puncturing-enabled state. The knob portion 160 has an outer diameter larger than the protruded wall 148, and the proximal end surface forms a level difference for the protruded wall 148 in the installed state of the cap 146. For this reason, the user can easily detach the cap 146 by a finger being caught in the proximal end surface of the knob portion 160.

In the puncturing-enabled state, the user brings the distal end portion of the outer cylinder 140 into contact with a patient, whereby the needle 12, the main body unit 14, the inner cylinder 142, and the like are moved forward relative to the outer cylinder 140. At this time, in the injector 10C, the guide passage 54 and the projection 154 of the inner cylinder 142 are covered with the cover 144, and accordingly, the user's finger or the like can be prevented from being in contact (interrupt) with the guide passage 54 and the projection 154. In accordance with this forward movement, the projection 154 of the inner cylinder 142 is moved from the before-puncturing section 56a to the puncturing section 58a of the guide passage 54. In the step in which the projection 154 is located at the puncturing section 58a, the needle 12 is exposed from the distal end of the outer cylinder 140 so as to puncture the patient, and a medicine is administered.

After the administration of the medicine, the injector 10C is pulled from the patient, whereby the outer cylinder 140 is moved forward to the distal end side under the action of the spring 44 and covers the needle 12. At this time, the projection 154 of the inner cylinder 142 advances over the claw portion 153 from the puncturing section 58a and is moved to the after-puncturing section 60a.

In the state in which the projection 154 is moved to the after-puncturing section 60a, when the outer cylinder 140 is moved backward, and the projection 154 is brought into contact with the locking side 153a of the claw portion 153, the projection 154 is led to the bottom portion of the V-shaped groove 153c. In this way, it is difficult for the projection 154 to deviate from the claw portion 153, and the inner cylinder 142 strongly restricts the backward movement of the outer cylinder 140, whereby the exposure of the needle 12 can be prevented. Even when a strong weight is applied from the projection 154 to the claw portion 153 according to the forward movement action of the main body unit 14, the cover 144 prevents the claw portion 153 from being deformed to the outer side, and the forward movement (in other words, the exposure of the needle 12) of the projection 154 can be prevented. Furthermore, the cover 144 blocks the interrupt from the outer side to the claw portion 153, and the engagement of the projection 154 using the claw portion 153 can be made more reliably.

Figure 18:
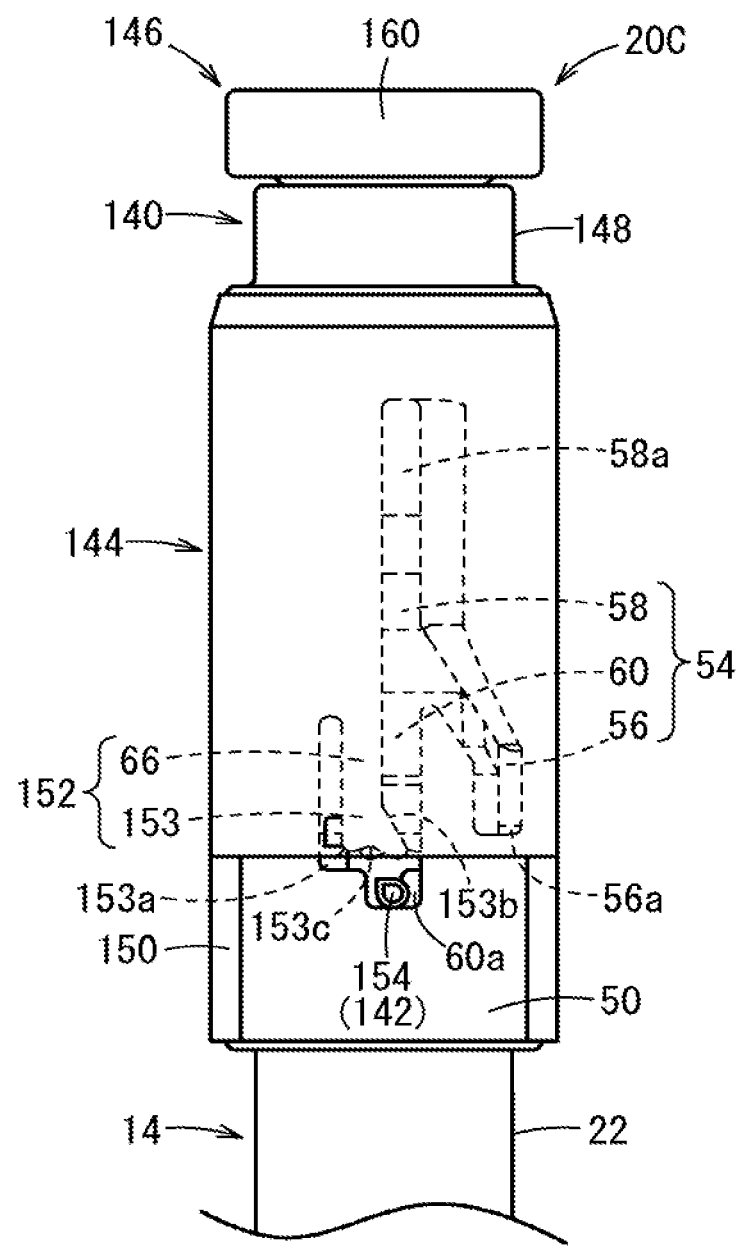
FIG. 18 is a side view that illustrates the distal end portion in a state after the puncturing process of the injector illustrated in FIG. 15.

In addition, as illustrated in FIG. 17A, in the puncturing-enabled state, the outer peripheral surface of the inner cylinder 142 is covered with the opaque cover 144, and the outer peripheral surface of the inner cylinder 142 cannot be visually recognized. Then, as illustrated in FIG. 18, in the state in which the projection 154 of the inner cylinder 142 is moved to the after-puncturing section 60a, the after-puncturing section 60a is located on the further proximal end side than the before-puncturing section 56a, and accordingly, the proximal end portion of the inner cylinder 142 protrudes to the further proximal end side than the cover 144. Accordingly, the outer peripheral surface of the proximal end portion of the inner cylinder 142 can be visually recognized through the outer cylinder 140 that is transparent or semi-transparent. For this reason, the user can recognize in a simple manner whether the injector 10C is in the non-used state or the use-completed state by visually recognizing the outer peripheral surface of the inner cylinder 142. Particularly, when the projection 154 is located at the after-puncturing section 60a, the outer peripheral surface of the proximal end portion of the inner cylinder 142 can be visually recognized over the peripheral direction, and accordingly, the user can recognize whether the injector 10C is in the non-used state or the use-completed state in a simpler manner. Here, the outer cylinder 140 may be configured to be opaque. In such a case, when the projection 154 is at the puncturing section 58a, the projection 154 is covered with the opaque cover 144 and is not visually recognized. On the other hand, in a case where the projection 154 is located at the after-puncturing section 60a, the projection 154 is exposed from the cover 144. Accordingly, the user can recognize whether the injector 10C is in the non-used state or in the use-completed state in a simple manner by checking the exposure (the rotation state of the inner cylinder 142) of the projection 154.

The injector 10D according to the fourth embodiment is not limited to the configuration described above, but various configurations may be employed. For example, in the fourth embodiment, while the cover 144 is configured using a relatively hard resin material similar to the outer cylinder 140, the inner cylinder 142, and the like, the outer cylinder 140 may be covered with a plastic film or the like.

In addition, between the outer surface of the claw portion 153 and the inner surface of the cover 144, a slight gap may be arranged. More specifically, it is preferable that the outer surface of the claw portion 153 is slightly sunk to the further inner side than the outer surface of the other portion of the outer cylinder 140 or that the inner surface of the cover 144 of the portion covering the outer surface of the claw portion 153 is slightly sunk to the further outer side than the inner surface of the cover 144 of the periphery. In such a case, the inner surface of the cover 144 is not in contact with the outer surface of the claw portion 153, and the claw portion 153 can be elastically deformed in the peripheral direction smoothly. For this reason, when the projection 154 of the inner cylinder 142 is moved from the puncturing section 58a to the after-puncturing section 60a, the claw portion 153 is elastically deformed in the peripheral direction smoothly, and the projection 154 can easily advance over the claw portion 153.

Fifth Embodiment

Figure 19:
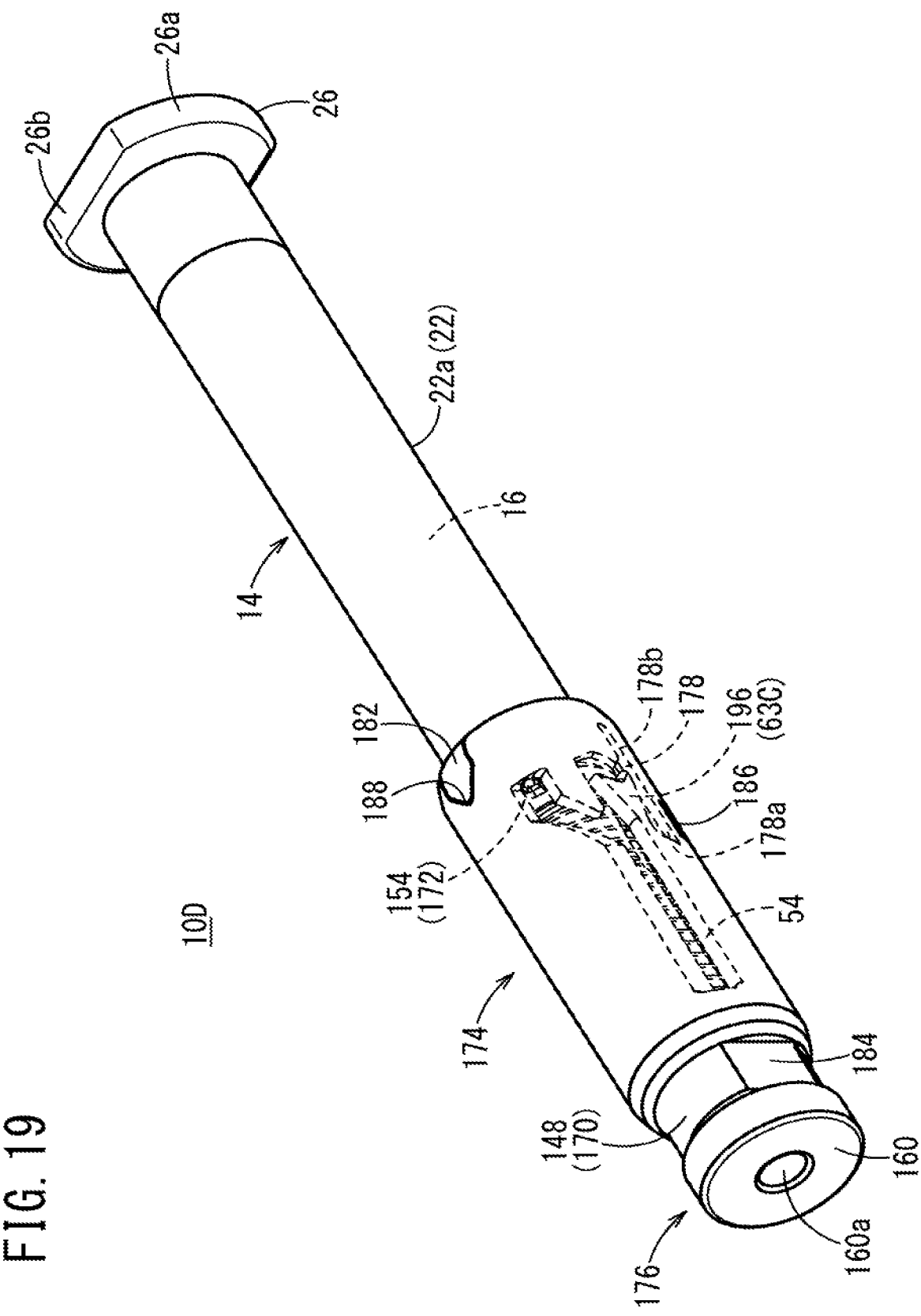
FIG. 19 is a perspective view that illustrates the whole configuration of an injector according to a fifth embodiment.
Figure 20:
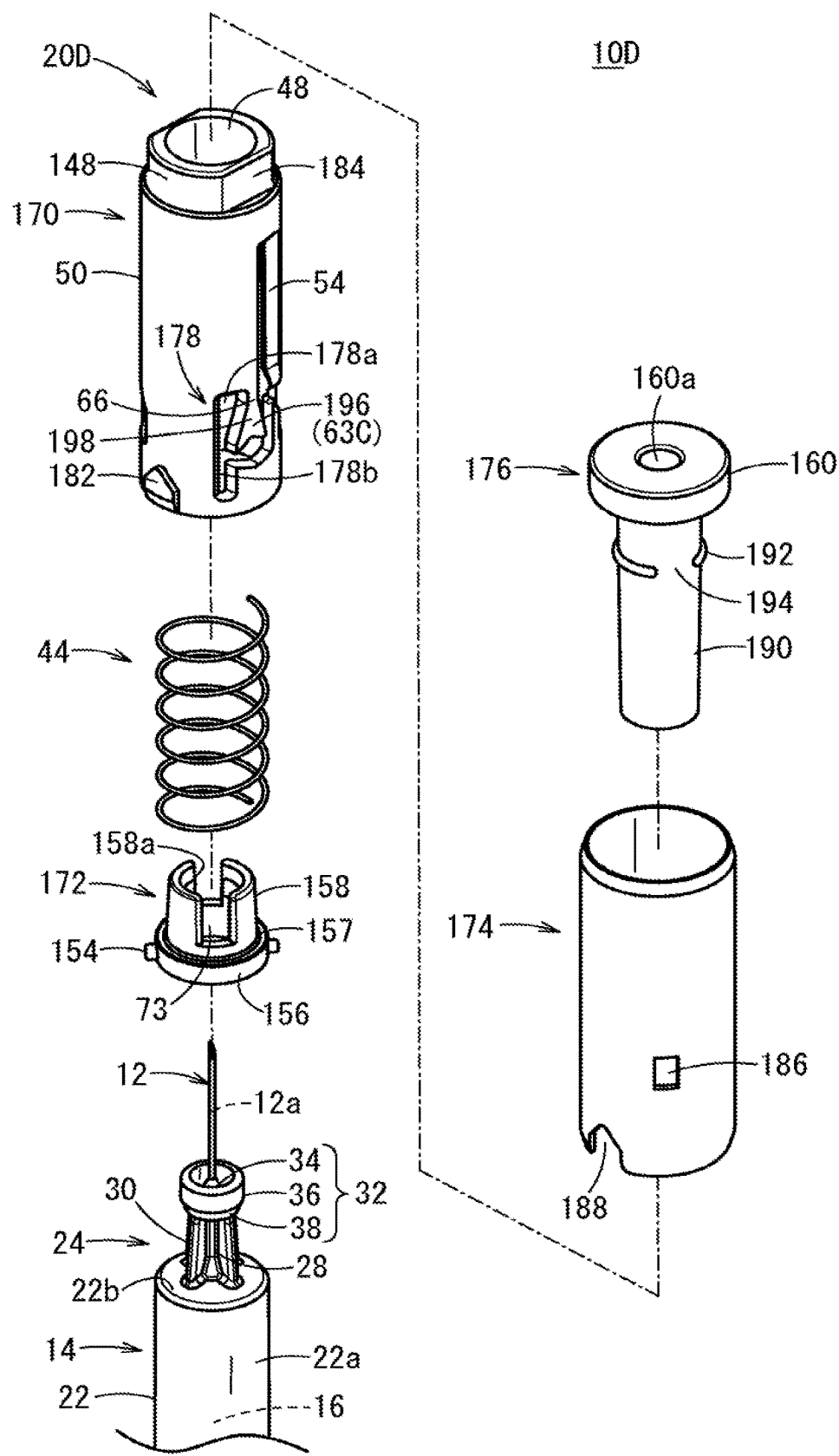
FIG. 20 is an exploded perspective view that illustrates a protection device of the injector illustrated in FIG. 19.

Next, an injector 10D according to a fifth embodiment will be described with reference to FIGS. 19 to 24B. The injector 10D (protection device 20D), as illustrated in FIG. 19, a cover 174 installed to an outer cylinder 170 is configured to cover the approximately entire outer peripheral surface of the side wall 50 of the outer cylinder 170, which is different from the injector 10C according to the fourth embodiment. In addition, as illustrated in FIG. 20, in the protection device 20D, the configurations of the outer cylinder 170, the inner cylinder 172, and the cap 176 are different from those of the protection device 20C to some extent.

While the outer cylinder 170, similar to the outer cylinder 140, includes the side wall 50 and the protruded wall 148, the shapes of a hook portion 196 (restriction portion 63C), a notched groove 178 that is configured to be continuous from the guide passage 54 of the side wall 50, and an after-puncturing section 60b are slightly different from those of the outer cylinder 140. More specifically, the hook portion 196 includes an elastic piece 66 and a claw portion 198 having a width that is gradually broadened to both sides in the peripheral direction toward the proximal end side facing the after-puncturing section 60b that is configured to be continuous from the proximal end side of the elastic piece 66. The claw portion 198 includes a V-shaped groove 198c on a locking side 198a facing the after-puncturing section 60b and includes an inclined side 198b in a protruded portion arranged on the third passage 60 side.

By forming the notched groove 178 so as to be continuous in the peripheral direction from the proximal end side of the third passage 60 in accordance with the shape of the hook portion 196, the after-puncturing section 60b exhibits a wide space. In other words, at the proximal end of the after-puncturing section 60b, a proximal end side 199 facing the locking side 198a is arranged. On the proximal end side 199, a V-shaped groove 199a having a bottom portion of which the phase of the peripheral direction approximately matches that of the bottom portion of the V-shaped groove 198c of the claw portion 198 is formed.

In addition, the notched groove 178 includes a distal end large-width groove 178a having a large width in the peripheral direction on the distal end side. Furthermore, the notched groove 178 includes a proximal end extended groove 178b that extends on the opposite side of the distal end large-width groove 178a toward the further proximal end side than the after-puncturing section 60b and notches the side wall 50 up to a position near the proximal end of the outer cylinder 170. This proximal end extended groove 178b has a function of promoting the elastic deformation of the outer cylinder 170 when the inner cylinder 172 is led to the guide passage 54 in the assembly of the protection device 20D.

Figure 21A:
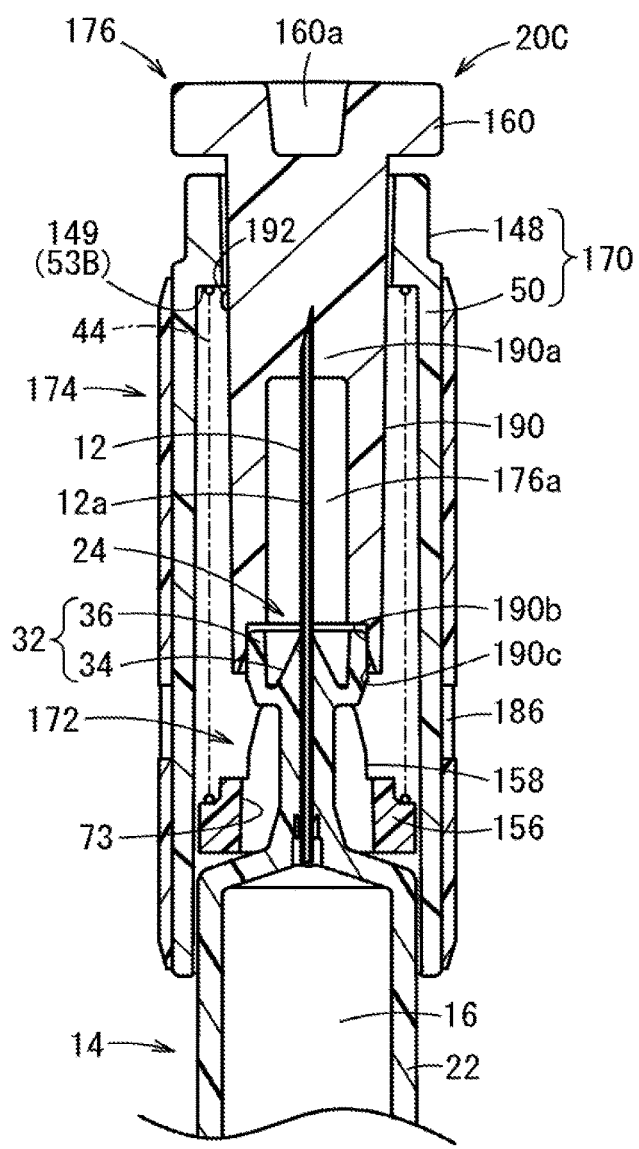
FIG. 21A is a side cross-sectional view that illustrates a distal end portion of the injector illustrated in FIG. 19.

Furthermore, as illustrated in FIG. 21A, on the inner peripheral surface of the side wall 50, similar to the outer cylinder 100 according to the second embodiment, one pair of leading groove portions 180 is arranged. The leading groove portion 180 is formed to arrive at the proximal end of the side wall 50 extending in a linear shape on the proximal end side of the first passage 56 of the guide passage 54. Between the leading groove portion 180 and the guide passage 54, a partition wall 181 is arranged, and the upper end side of the leading groove portion 180 is formed in a tapered surface 180a so as to be easily advanced by the projection 154 of the inner cylinder 172.

When the outer cylinder 170 and the inner cylinder 172 are assembled, the peripheral-direction positions are matched such that the projection 154 is inserted into the leading groove portion 180. Then, by inserting the inner cylinder 172 to the inner side along the leading groove portion 180, the projection 154 is arranged in the guide passage 54. When the projection 154 advances over the partition wall 181, the proximal end extended groove 178b arranged at a position of which the phase in the peripheral direction deviates from that of the partition wall 181 allows the side wall 50 of the peripheral portion of the partition wall 181 to be elastically deformed to the outer side in an easy manner. Accordingly, the projection 154 smoothly advances over the partition wall 181 and is moved into the guide passage 54.

As illustrated in FIGS. 19 and 20, the side wall 50 includes one pair of positioning convex portions 182 that position the outer cylinder 170 and the cover 174 in the peripheral direction and prevents positional deviations of the cover 174 on the proximal end side. The one pair of positioning convex portions 182 is arranged on the proximal end of the side wall 50 and protrudes by a height that approximately matching the thickness of the cover 174.

Figure 21B:
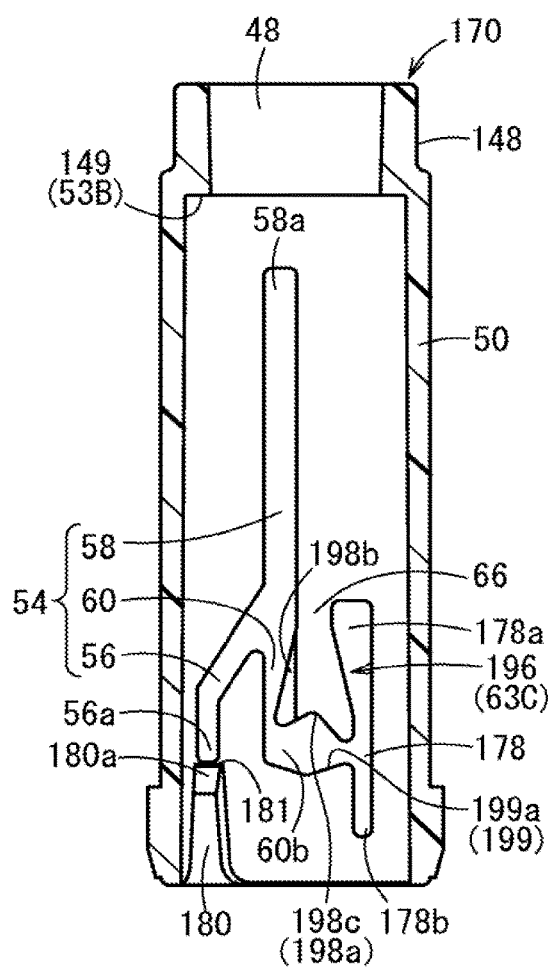
FIG. 21B is a side cross-sectional view that illustrates an outer cylinder of the injector illustrated in FIG. 19.

In addition, the protruded wall 148 of the outer cylinder 170 is formed to have a diameter slightly smaller than the side wall 50, and, as illustrated in FIG. 21B, a level difference 149 is formed on the inner side of the protruded wall 148. On the outer peripheral surface of the protruded wall 148, one pair of notched surfaces 184 is formed to be parallel with each other with the axial center of the protruded wall 148 being interposed therebetween. When the cap 176 is detached from the outer cylinder 170, the one pair of notched surfaces 184 enables the user's finger to be caught in the cap 176 more easily. In addition, one (notched edge portion) of ridgelines of both ends of the notched surfaces 184 may be arranged so as to match the phase of the leading groove portion 180 in the peripheral direction. In such a case, when the inner cylinder 172 is inserted into the outer cylinder 170, by matching the phase of the projection 154 to the ridgeline of the notched surface 184 in the peripheral direction, the projection 154 can be easily inserted into the leading groove portion 180.

Referring back to FIG. 20, the inner cylinder 172 housed inside the outer cylinder 170, similar to the inner cylinder 142 according to the fourth embodiment, includes a projection 154, a proximal end circular portion 156, and a distal end cylindrical portion 158 (including a cylindrical portion notching portion 158a). However, the inner cylinder 172 is colored with a color (for example, the needle holding portion 24 is transparent, and the inner cylinder 172 is colored in red) that is different from that of the needle holding portion 24.

Meanwhile, the cover 174 that covers the outer peripheral surface of the outer cylinder 170, as illustrated in FIGS. 19 and 20, includes one pair of window portions 186 at predetermined positions on the wall surface that configures the cover 174. Each of the window portions 186 is arranged to approximately overlap the distal end large-width groove 178a of the notched groove 178 that is formed to have a relatively large width in the state in which the cover 174 is installed to the outer cylinder 170. Accordingly, the needle holding portion 24 or the inner cylinder 172 that is present on the further inner side than the outer cylinder 170 can be visually recognized by the window portions 186.

In addition, at the proximal end of the cover 174, one pair of positioning concave portions 188 is formed. Each of the positioning concave portions 188 is formed in a shape matching the positioning convex portion 182 of the outer cylinder 170, and the positioning convex portion 182 is inserted in a state in which the outer cylinder 170 and the cover 174 are installed. Accordingly, the outer cylinder 170 and the cover 174 are integrated so as not to be rotatable, and the phases of the window portion 186 and the distal end large-width groove 178a in the peripheral direction can match each other constantly.

In addition, the cap 176 includes a knob portion 160 that is similar to that of the fourth embodiment and an extended cylinder portion 190 that is different from the extended cylinder portion 162 according to the fourth embodiment. As illustrated in FIG. 21A, the outer peripheral surface of the extended cylinder portion 190 is formed in a tapered shape having a diameter gently decreasing from the knob portion 160 toward the proximal end side, and thus, the extended cylinder portion 190 can be easily inserted into the inside of the outer cylinder 170.

On the outer peripheral surface of the extended cylinder portion 190, one pair of engagement projections 192 that can be caught in the level difference 149 (the sealing member holding portion 53B) of the outer cylinder 170 is arranged. The one pair of engagement projections 192 extends by a predetermined length in the peripheral direction on the outer peripheral surface of the extended cylinder portion 190 at the same positions of the extended cylinder portion 190 in the axial direction. One pair of gaps 194 is interposed between the engagement projections 192 according to no arrangement of the engagement projection 192. In addition, at least one engagement projection 192 and at least one gap 194 may be arranged at the same position of the extended cylinder portion 190 in the axial direction.

In addition, inside the extended cylinder portion 190, a hollow portion 176a into which the needle 12 is inserted is formed, and a sealing portion 190a is formed in the distal end portion of the hollow portion 176a. The proximal end portion of the extended cylinder portion 190 includes a proximal end opening portion 190b that is formed in an external shape having a diameter larger than that of the expanded cylinder portion 32 of the needle holding portion 24 and communicates with the hollow portion 176a. The inner diameter of the proximal end opening portion 190b is formed to be slightly smaller than the outer diameter of the expanded cylinder portion 32, and the inner surface of the extended cylinder portion 190 configuring the proximal end opening portion 190b is formed in a tapered portion 190c having a diameter increasing toward the proximal end side.

When the cap 176 formed as above is inserted into the hollow part 48 from the distal end portion of the outer cylinder 170, the proximal end portion of the extended cylinder portion 190 is covered with the expanded cylinder portion 32 of the needle holding portion 24. In other words, in accordance with the insertion of the extended cylinder portion 190 toward the proximal end side, the tapered portion 190c is brought into contact with the distal end portion of the expanded cylinder portion 32, and the proximal end portion of the extended cylinder portion 190 is extended to the outer side in the diameter direction while the expanded cylinder portion 32 is led to the inside of the proximal end opening portion 190b. Accordingly, the proximal end portion of the extended cylinder portion 190 and the needle holding portion 24 are brought into close contact with each other, and the hollow portion 176a (in other words, the needle 12) can be sufficiently sealed.

In addition, the cap 176 is inserted until the one pair of engagement projections 192 is located on the further proximal end side than the level difference 149 of the outer cylinder 170 and is in the state of being assembled to the outer cylinder 170. In this state, there is a space (margin) to some extent between the inner peripheral surface of the protruded wall 148 and the outer peripheral surface of the extended cylinder portion 190, and it is easy to allow the sterilization gas or the like to flow into the inside of the hollow part 48 of the outer cylinder 170. Particularly, because the gaps 194 are formed between the engagement projections 192, it is easier to allow the sterilization gas to flow therein. In addition, as the one pair of the engagement projections 192 is caught in the level difference 149, the movement of the cap 176 toward the distal end side is restricted. Accordingly, a tight contact between the proximal end portion of the extended cylinder portion 190 of the cap 176 and the needle holding portion 24 is maintained.

Figure 22A:
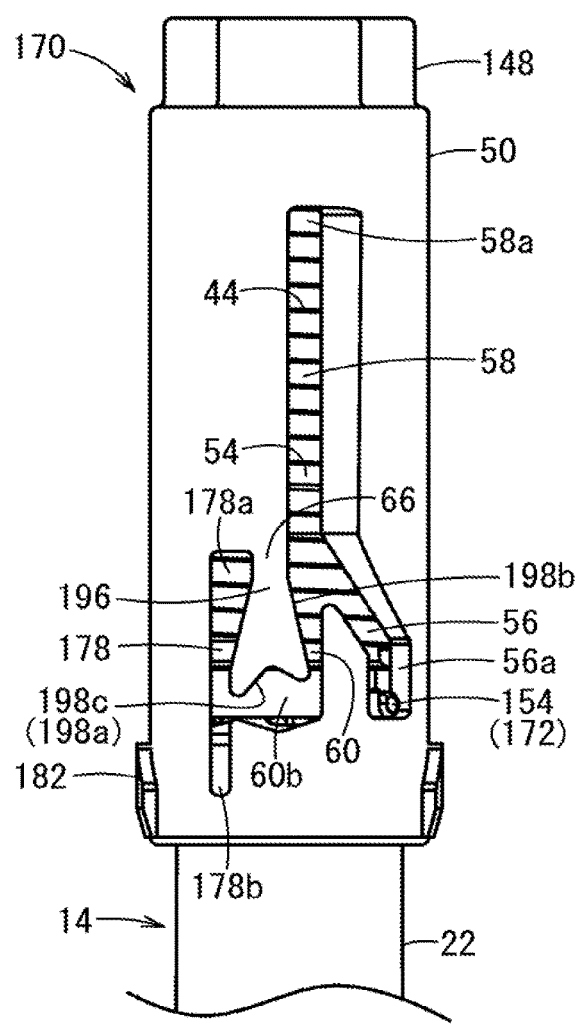
FIG. 22A is a side view that illustrates the arrangement of a projection of the injector illustrated in FIG. 19 before the puncturing process in a state in which a cover is excluded.
Figure 22B:
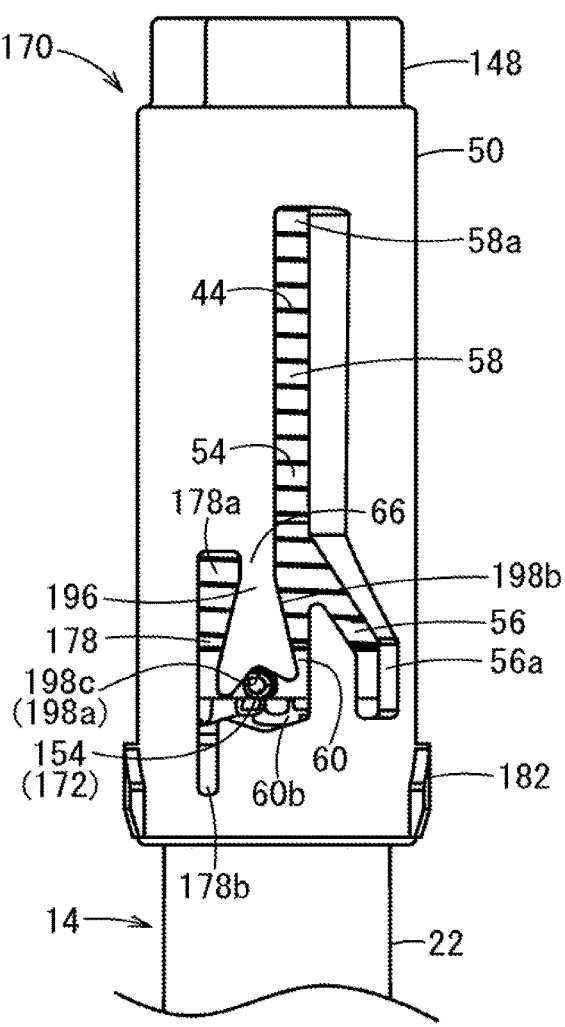
FIG. 22B is a side view that illustrates the projection state of the injector illustrated in FIG. 19 after the puncturing process in a state in which the cover is excluded.

The injector 10D according to the fifth embodiment performs the puncturing process using the needle 12 and the administration of the medicine based on the same operation as that of the injector 10. In other words, by moving the needle 12, the main body unit 14, the inner cylinder 172, and the like forward relative to the outer cylinder 170, the projection 154 of the inner cylinder 172 is moved along the guide passage 54 from the before-puncturing section 56a (see FIG. 22A) to the puncturing section 58a. After the movement to the puncturing section 58a, the outer cylinder 170 is moved forward with respect to the inner cylinder 172 in accordance with the elastic return of the contracted spring 44, whereby the projection 154 is moved to the after-puncturing section 60b (see FIG. 22B). In FIGS. 22A and 22B, in order to allow the position of the projection 154 to be easily understood, the cover 174 is not illustrated.

In the state in which the projection 154 is moved to the after-puncturing section 60b, when the outer cylinder 170 is attempted to be moved backward, the projection 154 restricts the backward movement by being strongly engaged with the locking side 198a of the claw portion 198, and accordingly, the exposure of the needle 12 can be prevented. Particularly, the claw portion 198 is formed in a relatively large size expanding in the peripheral direction, and the V-shaped groove 198c is arranged on the locking side 198a arranged on the proximal end side, whereby the positions of the bottom portion of the V-shaped groove 198c and the base of the elastic piece 66 match each other. Accordingly, when the projection 154 is led to the base portion of the V-shaped groove 198c, it is difficult for the elastic piece 66 to be transformed in the peripheral direction, and thus, the engaged state can be maintained well.

In addition, the V-shaped groove 199a arranged on the proximal end side 199 leads the projection 154 to the center portion of the after-puncturing section 60b in the widthwise direction. Accordingly, when the outer cylinder 170 is attempted to be moved backward toward the proximal end side, the projection 154 is brought into contact with a section near the bottom portion of the V-shaped groove 198c of the claw portion 198, and the engagement between the projection 154 and the claw portion 198 can be formed to be further strong. In addition, by preventing the deformation (separation from the inner cylinder 172) of the hook portion 196 to the outer side, the cover 174 can configure the engagement between the claw portion 153 and the projection 154 to be more reliable.

Furthermore, according to the injector 10D, by including the window portions 186 in the cover 174, the external appearance of the inner cylinder 172 can be visually recognized, and it can be checked whether the injector 10D is in the non-used state or in the use-completed state. In other words, before the injector 10D illustrated in FIGS. 23A and 23B is used (not used), the projection 154 of the inner cylinder 172 is located at the before-puncturing section 56a in the guide passage 54. At this time, on the window portion 186, the needle holding portion 24 is seen through the notched groove 178 (the distal end large-width groove 178a) of the outer cylinder 170. The reason for this is that the cylindrical portion notching portion 158a of the inner cylinder 172 overlaps the distal end large-width groove 178a. In other words, the external appearance of the inner cylinder 172 includes the notched groove 178 as well, and the user can recognize the non-used state of the injector 10D by visually recognizing the needle holding portion 24 through the notched groove 178.

On the other hand, after the injector 10D illustrated in FIGS. 24A and 24B is used, the projection 154 of the inner cylinder 172 is located at the after-puncturing section 60a in the guide passage 54. At this time, on the window portion 186, the distal end cylindrical portion 158 of the inner cylinder 172 is seen through the distal end large-width groove 178a. The reason for this is that, by rotating the inner cylinder 172 in the peripheral direction according to the movement of the projection 154, the distal end cylindrical portion 158 overlaps the distal end large-width groove 178a. As described above, because the inner cylinder 172 is colored with a color (red) different from that of the needle holding portion 24, the user can recognize the use-completed state (dangerousness) of the injector 10D by visually recognizing the inner cylinder 172.

Here, the formation position of the window portion 186 of the cover 174 is not limited to the position overlapping the notched groove 178 described above but may be freely designed. For example, the window portion 186 may be formed at a position overlapping the before-puncturing section 56a in the guide passage 54 of the outer cylinder 170. In other words, before the injector 10D is used, the non-used state can be recognized according to the exposure of the projection 154, and, after the injector 10D is used, the use-completed state can be recognized according to the exposure of the proximal end circular portion 156. In such a case, in the molding process, by changing the color of the projection 154 with respect to the color of the proximal end circular portion 156, the rotation state of the inner cylinder 172 can be acquired in an easier manner.

Sixth Embodiment

In an injector 10E according to a sixth embodiment, as illustrated in FIG. 25A, the configuration of a guide passage 202 arranged in an outer cylinder 200 (a protection device 20E) is different from those of the injectors 10 and 10A to 10D according to the first to fifth embodiments. The configuration other than the outer cylinder 200 is basically the same as that of the injector 10C, and FIGS. 15 to 18 may be referred to.

While a guide passage 202 of the outer cylinder 200 includes the first passage 56 and the second passage 58 of the guide passage 54 described above, the shape of a third passage 204 is different from that of the third passage 60 of the guide passage 54. While the distal end side portion of the third passage 204 that is continuous from the second passage 58 is formed in a straight line that is continuous from the second passage 58, the third passage 204 is obliquely bent (or curved) from a middle section and extends toward the oblique proximal end side. Accordingly, an after-puncturing section 60c is formed to deviate in the peripheral direction to a side opposite to the before-puncturing section 56a with respect to the puncturing section 58a and to be located on the further proximal end side then the before-puncturing section 56a. In addition, on the outer peripheral surface of the outer cylinder 200, while the cover 144 is installed, the proximal end side (including the after-puncturing section 60c) of the third passage 204 is exposed from the cover 144.

In addition, near the entrance of the after-puncturing section 60c, two claw portions 206 are arranged to face each other. The claw portions 206 protrude toward the inner side of the third passage 204, have the apexes thereof approaching each other, and are formed to have sides that are orthogonal to the space of the after-puncturing section 60c. This one pair of claw portions 206 serves as a restriction portion 63D that is engaged with the projection 154 when the projection 154 of the inner cylinder 142 is moved to the after-puncturing section 60c. Here, the restriction portion 63D is not limited to the one pair of claw portions 206 but may be configured by only one claw portion.

The injector 10E according to the sixth embodiment is basically configured as above. When the puncturing process using the needle 12 is performed, in accordance with the forward/backward movement of the outer cylinder 200, the projection 154 of the inner cylinder 142 is moved in order of the before-puncturing section 56a (see FIG. 25A), the puncturing section 58a, and the after-puncturing section 60c (see FIG. 25B). When the projection 154 is moved to the after-puncturing section 60c, the projection 154 advances over the one pair of claw portions 206. Then, when the outer cylinder 200 is attempted to be moved backward with respect to the inner cylinder 142, the projection 154 located at the after-puncturing section 60c is engaged with the one pair of claw portions 206, whereby the backward movement of the outer cylinder 200 that is made again is restricted. In addition, because the projection 154 is configured to be exposed from the cover 144, it can be checked whether the injector 10E is in the before-use state or the use-completed state by visually recognizing the projection 154.

In addition, the shape of the third passage 204 is not particularly limited, and, for example, the third passage 204 may be formed on the further proximal end side than the puncturing section 56a and formed to deviate in the same peripheral direction as that of the before-puncturing section 56a with respect to the puncturing section 58a.

While the preferred embodiments of the present invention have been described, the present invention is not limited to the embodiments described above, but various changes may be made therein in a range not departing from the concept of the present invention. In addition, the embodiments may be appropriately combined such as addition of the leading groove portion 104 according to the second embodiment to the outer cylinder 40 according to the first embodiment or replacement the hook portion 64 according to the first embodiment with the hook portion 114 according to the second embodiment.

What is claimed is:

1. An injector comprising:
a hollow needle;
a main body unit including a needle holding portion that holds the needle; and
a protection device configured to cover the needle before and after puncturing a puncture target with the needle,
wherein the protection device includes:
an inner member attached to the needle holding portion and being freely rotatable around an outer periphery of the needle holding portion; and
an outer member configured to (i) cover an outer side of the needle and the inner member before puncturing, (ii) expose the needle by moving toward a proximal end side relative to the main body unit at a time of puncturing, and (iii) cover a distal end of the needle by moving toward a distal end side relative to the main body unit after puncturing,
wherein the inner member includes a cylinder portion and a projection that protrudes outward from the cylinder portion,
wherein the outer member includes:
a guide passage having the projection arranged therein and configured to rotate the inner member by guiding the projection to a predetermined section when the outer member is moved from before the puncturing to after the puncturing; and
a restriction portion configured to restrict movement of the outer member toward the proximal end side with respect to the main body unit by being engaged with the cylinder portion of the inner member when the projection is moved to the predetermined section.

2. The injector according to claim 1,
wherein the inner member and the outer member are cylindrical, and
wherein an axial length of the inner member is shorter than a length of the guide passage in a direction parallel to an axis of the outer member.

3. The injector according to claim 2,
wherein the needle holding portion includes a support cylinder portion, and an expanded cylinder portion that is arranged at a distal end of the support cylinder portion and has an outer diameter larger than an outer diameter of the distal end of the support cylinder portion, and
wherein the inner member has an attachment portion that is configured to be engaged with a connection portion of the support cylinder portion and the expanded cylinder portion.

4. The injector according to claim 2,
wherein the main body unit includes a trunk portion that extends from a proximal end of the needle holding portion, and
wherein an outer diameter of the cylinder portion is equal to or less than an outer diameter of the trunk portion and the projection that protrudes from the cylinder portion toward the outer member.

5. The injector according to claim 2,
wherein the main body unit further includes a hanging portion that is formed at a proximal end side of the main body unit and that protrudes in a direction that is substantially perpendicular to the axis of the main body unit, and wherein an outer diameter of the outer member is smaller than a maximum outer diameter of the hanging portion.

6. The injector according to claim 1,
wherein the guide passage includes:
a before-puncturing section at which the projection is arranged before puncturing;
a puncturing section to which the projection is movable at the time of puncturing, the puncturing section being located distal of the before-puncturing section; and
an after-puncturing section to which the projection is movable after puncturing, the after-puncturing section being located proximal of the puncturing section, and having a phase in a peripheral direction of the outer member deviating with respect to the before-puncturing section, and the after-puncturing section corresponding to the predetermined position, and
wherein the restriction portion includes a hook portion that restricts movement of the outer member toward the proximal end side by being engaged with the inner member when the projection is moved to the after-puncturing section.

7. The injector according to claim 6,
wherein the hook portion includes a convex portion that protrudes to an inner side in a diameter direction of the outer member,
wherein the inner member further includes:
an engagement portion that is engageable with the convex portion when the projection is located at the after-puncturing section; and
a passage allowing portion configured such that the convex portion is passable therethrough from a distal end to a proximal end of the inner member, and
wherein the engagement portion and the passage allowing portion have phases deviating from each other in the peripheral direction of the inner member.

8. The injector according to claim 7,
wherein the hook portion includes an elastic piece in which the convex portion is arranged, and
wherein the injector is configured such that, when the projection is moved from the puncturing section to the after-puncturing section, the convex portion advances over the engagement portion by elastically deforming the elastic piece to an outer side in a radial direction.

9. The injector according to claim 6, wherein the hook portion includes a claw portion that protrudes to the inside of the guide passage near a distal end of the after-puncturing section and that is configured to restrict movement of the outer member to the proximal end side by engaging with the projection that is moved to the after-puncturing section.

10. The injector according to claim 9,
wherein the hook portion includes an elastic piece, in which the claw portion is arranged, adjacent to the guide passage between the puncturing section and the after-puncturing section, and
wherein the projection is configured to advance over the claw portion by elastically deforming the elastic piece when the projection is moved from the puncturing section to the after-puncturing section.

11. The injector according to claim 10,
wherein the claw portion includes a V-shaped groove that is open toward the after-puncturing section on a side opposing the after-puncturing section, and
wherein the injector is configured such that, when the projection located at the after-puncturing section is moved toward the puncturing section, the projection is led to a bottom portion of the V-shaped groove by being brought into contact with the V-shaped groove.

12. The injector according to claim 10, wherein a cover that restricts deformation of the elastic piece to an outer side is arranged on an outer peripheral surface of the outer member.

13. The injector according to claim 12, wherein a gap is formed between an inner surface of the cover and an outer surface of the claw portion.

14. The injector according to claim 1,
wherein the injector further comprises a sealing member that has a hollow portion housing the needle and a sealing portion sealing the distal end of the needle on an inside thereof,
wherein the outer member has a sealing member holding portion that detachably holds the sealing member, and
wherein the sealing member, when held by the sealing member holding portion before puncturing, seals the hollow portion as a proximal end portion of the sealing member is brought into contact with a distal end portion of the needle holding portion.

15. The injector according to claim 1,
wherein the outer member includes a hollow part that houses the needle and the inner member, and
wherein a leading groove portion is formed on an inner surface of the outer member, the leading groove portion being configured to lead the projection to the guide passage when the inner member is inserted into the hollow part from the proximal end side.

16. The injector according to claim 15, wherein the leading groove portion includes:
a first groove that is formed in a linear shape parallel to an insertion direction of the inner member toward the guide passage near a proximal end of the guide passage; and
a second groove that is inclined in a rotation direction of the inner member to the distal end side toward the first groove that is continuous from a proximal end side of the first groove.

17. The injector according to claim 1,
wherein the guide passage includes:
a before-puncturing section at which the projection is arranged before puncturing;
a puncturing section to which the projection is movable at the time of puncturing, the puncturing section being located distal of the before-puncturing section; and
an after-puncturing section to which the projection is movable after puncturing, the after-puncturing section being located proximal of the puncturing section and being in a position different from the before-puncturing section in an axial direction of the outer member,
wherein a cover is arranged on an outer peripheral surface of the outer member, and
wherein, when the projection is located at one of the before-puncturing section and the after-puncturing section, the cover covers an entirety of the outer peripheral surface of the inner member, and
wherein, when the projection is located at the other of the before-puncturing section and the after-puncturing section, the cover allows at least a part of the inner member to protrude distally or proximally from the cover.

18. The injector according to claim 1,
wherein a cover having a window portion through which an inside of the outer member is visually perceivable is arranged on an outer peripheral surface of the outer member, and
wherein an external appearance of the inner member that is visually perceivable through the window portion has a first appearance when the injector is in a state before rotation of the inner member and has a second appearance different from the first appearance in a state after rotation of the inner member.

* * * * *